US008999896B2

(12) United States Patent
Hwang et al.

(10) Patent No.: US 8,999,896 B2
(45) Date of Patent: Apr. 7, 2015

(54) DISCOVERY AND APPLICATIONS OF THE PROTEOLYTIC FUNCTION OF N-TERMINAL ACETYLATION OF CELLULAR PROTEINS

(75) Inventors: Cheol-Sang Hwang, Arcadia, CA (US); Anna Shemorry, Pasadena, CA (US); Alexander Varshavsky, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 789 days.

(21) Appl. No.: 13/007,546

(22) Filed: Jan. 14, 2011

(65) Prior Publication Data

US 2011/0230370 A1     Sep. 22, 2011

Related U.S. Application Data

(60) Provisional application No. 61/295,639, filed on Jan. 15, 2010.

(51) Int. Cl.
| | | |
|---|---|---|
| *C40B 30/08* | (2006.01) | |
| *A61K 38/00* | (2006.01) | |
| *C07K 2/00* | (2006.01) | |
| *C07K 4/00* | (2006.01) | |
| *C07K 5/00* | (2006.01) | |
| *C07K 7/00* | (2006.01) | |
| *C07K 14/00* | (2006.01) | |
| *C07K 16/00* | (2006.01) | |
| *C07K 17/00* | (2006.01) | |
| *C12Q 1/66* | (2006.01) | |
| *C12Q 1/48* | (2006.01) | |

(52) U.S. Cl.
CPC ........ *C12Q 1/48* (2013.01); *G01N 2333/91045* (2013.01); *G01N 2500/02* (2013.01); *G01N 2500/10* (2013.01)

(58) Field of Classification Search
CPC . C12Q 1/48; G01N 2500/02; G01N 2500/10; G01N 2333/91045
See application file for complete search history.

(56) References Cited

U.S. PATENT DOCUMENTS

| | | | |
|---|---|---|---|
| 5,206,347 A | 4/1993 | Ruoslahti et al. | |
| 5,264,563 A | 11/1993 | Huse | |
| 5,571,698 A | 11/1996 | Ladner | |
| 5,622,699 A | 4/1997 | Ruoslahti et al. | |
| 5,766,927 A | 6/1998 | Baker et al. | |
| 2002/0086388 A1 | 7/2002 | Cahoon et al. | |
| 2004/0146987 A1 | 7/2004 | Zdanovsky et al. | |
| 2006/0234313 A1 | 10/2006 | Kwon et al. | |

FOREIGN PATENT DOCUMENTS

WO     WO 2007/148106     12/2007

OTHER PUBLICATIONS

Arnesen, T. et al., "A Novel Human Nata Nα-Terminal Acetyltransferase Complex: hNaa16p-hNaa10p (hNat2-hArd1)," *BMC Biochemistry*, May 29, 2009, pp. 1-17, vol. 10, No. 15.

Blondelle, S. E. et al., "Soluble Combinatorial Libraries of Organic, Peptidomimetic and Peptide Diversities," *Trends in Analytical Chemistry*, 1995, pp. 83 92, vol. 14.

Borrabeck, C. A., "Antibody Engineering, 2nd Editon," Oxford University Press, 1995.

De Groot, R. J. et al., "Sindbis Virus RNA Polymerase is Degraded by the N-End Rule Pathway," *Proceedings of the National Academy of Sciences of the United States of America*, Oct. 1991, pp. 8967-8971, vol. 88.

De Kruif, J. et al., "Biosynthetically Lipid-Modified Human scFv Fragments from Phage Display Libraries as Targeting Molecules for Immunoliposomes," *Federation of European Biochemical Societies Letters*, 1996, pp. 232-236, vol. 399.

Ding, Y. et al., "Synthesis and Biological Activity of Oligosaccharide Libraries," *Advances in Experimental Medicine and Biology*, 1995, pp. 261-269, vol. 376.

Dive, V. et al., "Phosphinic Peptide Inhibitors as Tools in the Study of the Function of Zinc Metallopeptidases," *Biochemical Society Transactions*, 2000, pp. 455-460, vol. 28, No. 4.

Ecker, D. J. et al., "Combinatorial Drug Discovery: Which Methods Will Produce the Greatest Value?", *Nature Biotechnology*, vol. 13, pp. 351-360, 1995.

Gold, L. et al., Diversity of Oligonucleotide Functions: *Annual Review of Biochemistry*, Jul. 1995, pp. 763-797, vol. 64.

Gonda, D. K. et al., "Universality and Structure of the N-end Rule," *The Journal of Biological Chemistry*, Oct. 5, 1989, pp. 16700-16712, vol. 264.

Gordon, E. M. et al., "Applications of Combinatorial Technologies to Drug Discovery. 2. Combinatorial Organic Synthesis, Library Screening Strategies, and Future Directions," *The Journal of Medicinal Chemistry*, May 13, 1994, pp. 1385-1401, vol. 37, No. 10.

Harlow, E. et al., "Antibodies: A Laboratory Manual," Cold Spring Harbor Laboratory Press, 1999.

Hershko, A. et al., "The Ubiquitin System," *Annual Review of Biochemistry*, Jul. 1998, pp. 425-479, vol. 67.

Hilyard, K. L. et al., "Protein Engineering of Antibody Combining Sites" Chapter in *Protein Engineering: A Practical Approach*, (Rees, et al., eds.) 1992, pp. 253-275, IRL Press at Oxford University Press, New York.

Hochstrasser, M., "Ubiquitin-Dependent Protein Degradation," *Annual Review of Genetics*, Dec. 1996, pp. 405-439, vol. 30.

(Continued)

*Primary Examiner* — James H Alstrum Acevedo
*Assistant Examiner* — Zachary J Miknis
(74) *Attorney, Agent, or Firm* — DLA Piper LLP (US)

(57) ABSTRACT

Screening assays that allow for the identification of agents that modulate the activity of N-terminal acetylation of a polypeptide and the Doa10 branch of the N-end rule pathway are provided. Also provided are methods of using an agent that modulates the activity of N-terminal acetylation of a polypeptide and the Doa10 branch of the N-end rule pathway to increase or decrease protein degradation in a cell, and to modulate physiologic and pathologic associated with N-terminal acetylation of a polypeptide and the Doa10 branch of the N-end rule pathway.

19 Claims, 13 Drawing Sheets

(56) References Cited

OTHER PUBLICATIONS

Huse, W. D. et al., "Generation of a Large Combinatorial Library of the Immunoglobulin Repertoire in Phage Lambda," *Science*, Dec. 8, 1989, pp. 1275-1281, vol. 246.

Hwang, W. W. et al., "A Conserved Ring Finger Protein Required for Histone H2B Monoubiquitination and Cell Size Control," *Molecular Cell*, Jan. 1, 2003, pp. 261-266, vol. 11, Issue 1.

Jellinek, D. et al., "Potent 2'-Amino-'-deoxypyrimidine RNA Inhibitors of Basic Fibroblast Growth Factor," *Biochemistry*, Sep. 12, 1995, pp. 11363-11372, vol. 34.

Karaoglu, D. et al., "Functional Characterization of Ost3p. Loss of the 34-kD Subunit of the *Saccharomyces cerevisiae* Olidosaccharyltransferase Results in Biased Underglycosylation of Acceptor Substrates," *The Journal of Cell Biology*, Aug. 1, 1995, pp. 567 577, vol. 130, No. 3.

Kwon, Y. T. et al., "An Essential Role of N-Terminal Arginylation in Cardiovascular Development," *Science*, Jul. 5, 2002, pp. 96-99, vol. 297.

Lecker, S. H. et al., "Ubiquitin Conjugation by the N-End Rule Pathway and mRNAs for Its Components Increase in Muscles of Diabetic Rats," *The Journal of Clinical Investigation*, Nov. 15, 1999, pp. 1411-1420, vol. 104, Issue 10.

Liang, R. et al., "Parallel Synthesis and Screening of a Solid Phase Carbohydrate Library," *Science*, Nov. 29, 1996, pp. 1520-1522, vol. 274.

Lin, Y. et al., "Modified RNA Sequence Pools for in vitro Selection," *Nucleic Acids Research*, Dec. 11, 1994, pp. 5220-5234, vol. 22, No. 24.

Markland, W. et al., "Design, Construction and Function of a Multicopy Display Vector Using Fusions to the Major Coat Protein of Bacteriophage M13," *Gene*, Dec. 20, 1991, pp. 13-19, vol. 109, Issue 1.

O'Connell, D. et al., "Calcium-Dependent Oligonucleotide Antagonists Specific for L-Selectin," *Proceedings of the National Academy of Sciences of the United States of America*, Jun. 11, 1996, pp. 5883-5887, vol. 93, No. 12.

Pagratis, N. C. et al., "Potent 2'-amino-, and 2'-fluoro-2'—deoxyribonucleotide RNA Inhibitors of Keratinocyte Growth Factor," *Nature Biotechnology*, Jan. 1997, pp. 68-73, vol. 15, No. 1.

Rao, H. et al., "Degradation of a Cohesin Subunit by the N-End Rule Pathway is Essential for Chromosome Stability," *Nature*, Apr. 19, 2001, pp. 955-959, vol. 410.

Scott, J. K. et al., "Searching for Peptide Ligands with an Epitope Library," *Science*, Jul. 27, 1990, pp. 386-390, vol. 249.

Solomon, V. et al., "Rates of Ubiquitin Conjugation Increase when Muscles Atrophy, Largely through Activation of the N-End Rule Pathway," *Proceedings of the National Academy of Sciences of the United States of America*, Oct. 13, 1998, pp. 12602-12607, vol. 95, No. 21.

Tam, R. C. et al., "Biological Availability and Nuclease Resistance Extend the in vitro Activity of a Phosphorothioate-3'hydroxypropylamine Oligonucleotide," *Nucleic Acids Research*, Mar. 25, 1994, pp. 977-986, vol. 22, No. 6.

Tuerk, C. et al., "Systematic Evolution of Ligands by Exponential Enrichment: RNA Ligands to Bacteriophage T4 DNA Polymerase," *Science*, Aug. 3, 1990, pp. 505-510, vol. 249.

Turner, G. C. et al., "Peptides Accelerate their Uptake by Activating a Ubiquitin-Dependent Proteolytic Pathway," *Nature*, Jun. 1, 2000, pp. 579-583, vol. 405.

Varshavsky, A., "The N-end Rule: Functions, Mysteries, Uses," *Proceedings of the National Academy of Sciences of the United States of America*, Oct. 29, 1996, pp. 12142-12149, vol. 93, No. 22.

Varshavsky, A., "The N-End Rule Pathway of Protein Degradation," *Genes to Cells*, Jan. 1997, pp. 13-28, vol. 2, No. 1.

Varshavsky, A., "The Ubiquitin System," *Trends in Biochemical Sciences*, Oct. 1997, pp. 383-387, vol. 22, Issue 10.

Ward, E. S. et al., "Binding Activities of a Repertoire of Single Immunoglobulin Variable Domains Secreted from *Escherichia coil*," *Nature*, Oct. 12, 1989, pp. 544-546, vol. 341.

Winter, G. et al., "Humanized Antibodies," *Immunology Today*, Jun. 1993, pp. 243-246, vol. 14, Issue 6.

Ye, Y. et al., "Convenient Conversion of Amino Acids to Their N-Hydroxylated Derivatives on a Solid Support: Synthesis of Hydroxamate-Based Pseudo-Peptides," *Peptides: The Wave of the Future*, Proceedings of the Second International and the Seventeenth American Peptide Symposium Jun. 9-14, 2001, (Lebl and Houghten, ed.), 2001, pp. 589-590, American Peptide Society.

Ye, Y. et al., "Peptide Bond Modification for Metal Coordination: 1. Metal-Binding Properties of Hydroxamate-Based Pseudo-Peptides," *Peptides: The Wave of the Future*, Proceedings of the Second International and the Seventeenth American Peptide Symposium Jun. 9-14, 2001, (Lebl and Houghten, ed.), 2001, pp. 591-592, American Peptide Society.

Ye, Y. et al., "Peptide Bond Modification for Metal Coordination: 3. Metal-Binding Properties of Phosphorus-Based Pseudo-peptides," *Peptides: The Wave of the Future*, Proceedings of the Second International and the Seventeenth American Peptide Symposium Jun. 9-14, 2001, (Lebl and Houghten, ed.), 2001, pp. 595-596, American Peptide Society York, W. S. et al., "The Structures of Arabinoxyloglucans Produced by Solanaceous Plants," *Carbohydrate Research*, May 14, 1996, pp. 99-128, vol. 285.

International Search Report in connection with International Application No. PCT/US2011/021432 dated Sep. 20, 2011.

US 8,999,896 B2

DISCOVERY AND APPLICATIONS OF THE PROTEOLYTIC FUNCTION OF N-TERMINAL ACETYLATION OF CELLULAR PROTEINS

CROSS REFERENCE TO RELATED APPLICATIONS

This application claims the benefit of priority under 35 U.S.C. §119(e) of U.S. provisional application Ser. No. 61/295,639, filed Jan. 15, 2010, the entire content of which is hereby incorporated by reference in its entirety for all purposes.

GRANT INFORMATION

The invention was made with government support under Grant Nos. DK39520 and GM31530 awarded by the National Institutes of Health. The United States government has certain rights in this invention.

FIELD OF THE DISCLOSURE

The disclosure relates generally to the field of intracellular metabolism and catabolism, and more specifically to N-terminal acetylation of cellular proteins as a modification that creates previously unknown, specific degradation signals (degrons) that are targeted by a branch of the ubiquitin-dependent N-end rule pathway; methods of modulating protein degradation in a cell via the N-terminal acetylation of cellular proteins that are targeted by this pathway; and to methods of ameliorating physiological and/or pathological conditions associated with the N-terminal acetylation of cellular proteins that are also targeted by this pathway.

BACKGROUND OF THE DISCLOSURE

The ability to degrade proteins is an essential function of all eukaryotic cells. The ubiquitin-proteasome system has evolved to play an active role in cellular quality control by selective degradation of normal or damaged proteins. The ubiquitin-proteasome system is fundamental to cell cycle control, transcriptional regulation, stress response, immune and inflammatory responses and other vital processes. (For a review of the ubiquitin-proteasome system, see Hershko and Ciechanover, 1998, Annu. Rev. Biochem, 67:425-479; Varshaysky, 1997, Trends Biochem. Sci., 22: 383-387; and Hochstrasser, 1996, Annu. Rev. Genet, 30: 405-439.)

Ubiquitin (Ub) is a highly conserved 76-amino acid protein. Protein degradation via the ubiquitin-proteasome pathway generally involves covalent attachment of multiple molecules of ubiquitin to the protein substrate. The protein substrate is subsequently degraded by the 26S proteasome complex, and the free ubiquitin is recycled. There are also examples of proteins whose functions appear to be regulated by ubiquitylation, although ubiquitylation does not appear to target them for degradation (Hwang et al., 2003, Mol. Cell, 11: 261-266).

The attachment of ubiquitin to many known substrate proteins is believed to occur in a series of enzymatic reactions carried out sequentially by three classes of proteins: an ubiquitin-activating enzyme (E1) activates ubiquitin in an ATP-dependent manner to form a thioester bond between the carboxy-terminal Gly of Ub and a Cys residue of E1; activated Ub is then transferred to an ubiquitin-conjugating enzyme (E2 or UBC) to form another thioester bond; and a ubiquitin ligase (E3) catalyzes or promotes, in a substrate specific manner, the transfer of Ub from the E2 to a Lys residue of the substrate protein to form an isopeptide bond. An internal Lys residue of Ub can also form an isopeptide bond with the C-terminus of another Ub to create a multi-Ub chain that serves as a targeting signal for proteasome.

One specific example of an important ubiquitylation pathway is N-end rule ubiquitylation, and especially N-end rule ubiquitylation where ubiquitylation is preceded by N-terminal segment cleavage, where the N-terminal segment comprises one or more amino acid residues. The proteolysis exposes an N-degron, which comprises a destabilizing N-terminal residue plus an internal Lys residue where a multi-Ub chain is later attached. The N-terminal segment is cleaved to form an activated substrate of the ubiquitin-dependent N-end rule pathway (activated fragment), which is recognized through the exposed destabilizing N-terminal residue.

Prior to the discovery of the new N-terminal acetylation (Nt-acetylation) branch of the N-end rule pathway has been the subject of several review articles (Varshaysky, 1996, Proc. Natl. Acad. Sci. U.S.A., 93: 12142). The ubiquitin ligase UBR1, an E3 ligase, has been shown to ubiquitylate N-end rule substrates and has two binding sites for primary destabilizing N-terminal residues. The type I site is specific for basic N-terminal residues Arg, Lys, His. The type II site is specific for bulky hydrophobic residues Phe, Leu, Trp, Tyr, and Ile. Dipeptides carrying type I or type II N-terminal residues can serve as inhibitors of ubiquitylation of the corresponding type I or type II N-end rule substrates (Gonda et al., 1989, J. Biol. Chem., 264: 16700-16712). UBR1 from yeast contains yet another substrate-binding site, which recognizes proteins for ubiquitylation through an internal recognition site on substrates; this process can be enhanced by the presence of type I and type II dipeptides (Turner et al., 2000, Nature, 405: 579-583).

The degradation signal for ubiquitylation via the N-end rule pathways is termed an "N-degron" and comprises the primary destabilizing N-terminal residue and an internal lysine which is the site of ubiqutylation. Destabilizing N-terminal residues can be generated through proteolytic cleavages of specific proteins and other N-terminal modifications which reveal destabilizing residues at the new N-terminus. The residues that are exposed or modified to reveal an N-degron have been termed a "pre-N-degron" or "pro-N-degron." For example, Sindbis virus RNA polymerase is produced during viral infection through site-specific cleavage of the viral polyprotein precursor and carries an N-terminal Tyr that has been shown in rabbit reticulocyte lysates to target the protein for ubiquitylation via the N-end rule pathway (de-Groot et al., 1991, Proc. Natl. Acad. Sci. U.S.A., 88: 8967-8971). Another example is RGS4, whose N-terminal degradation signal is generated through a series of N-terminal modifications including (i) removal of N-terminal Met and exposure of Cys-2 at the N-terminus, (ii) oxidation of Cys-2 into cysteic acid, and (iii) conjugation of Arg to the N-terminus of the protein (Kwon et al., 2002, Science, 297: 96-99).

Relatively few physiological N-end rule substrates have been characterized to date. However, recently discovered N-end rule substrates linked to disease or pathology demonstrate the biological importance of N-end rule ubiquitylation pathway. For example, a carboxy-terminal fragment of cohesin in *Saccharomyces cerevisiae* is a physiological substrate for the ubiquitin/proteasome-dependent N-end rule pathway. Overexpression of this fragment is lethal and, in cells that lack an N-end rule ubiquitylation pathway, a highly increased frequency of chromosome loss is detected (Rao et al., 2001, Nature, 410: 955-959). Recent studies also indicate that enhanced protein breakdown in skeletal muscle leading to muscle wasting in patients with acute diabetes results from an accelerated Ub conjugation and protein degradation via the N-end rule pathway. The same pathway is activated in cancer cachexia, sepsis and hyperthyroidism (Lecher et al., 1999, J. Clin. Invest., 104: 1411-1420; and Solomon et al., 1998, Proc. Natl. Acad. Sci. USA, 95: 12602-12607).

SUMMARY OF THE DISCLOSURE

Many eukaryotic proteins are acetylated at the α-amino group of their N-terminal residues (FIG. 5A). Previous studies of $N^\alpha$-terminal acetylation (Nt-acetylation) characterized Nt-acetylated proteins and $N^\alpha$-terminal acetyltransferases (Nt-acetylases) that catalyze this cotranslational modification. Owing to the design of the genetic code, nascent proteins contain N-terminal Met. A retained N-terminal Met that is followed by "acetylation-permissive" residues is usually Nt-acetylated (FIG. 5A). Met-aminopeptidases cleave off the N-terminal Met if the residue at position 2 has a small enough side chain, resulting in N-terminal Ala, Val, Ser, Thr, Cys, Gly or Pro (FIG. 5B). With the near-exception of Gly and Pro, these N-terminal residues are often Nt-acetylated, similarly to N-terminal Met. In cell extracts, some Nt-acetylated proteins can be degraded by the ubiquitin (Ub) system. However, no cognate Ub ligases have been identified, and it has been assumed that the relevant degradation signals were internal (not N-terminal). Currently, the prevalent view of Nt-acetylation is that this modification protects proteins from degradation. Surprisingly, it has been found that Nt-acetylation creates specific degradation signals (degrons) that are targeted by a novel branch of the ubiquitin-dependent N-end rule pathway.

Thus, the present disclosure is based, in part, on the discovery that N-terminal acetylation by a $N^\alpha$-terminal acetyl transferase, of a polypeptide having an amino terminal (N-terminal) Met, Ala, Val, Ser, Thr, Cys, Gly, or Pro residue, creates specific degradation signals (N-degrons) that are targeted by Doa10 E3 Ub ligase, a branch of the ubiquitin-dependent N-end rule pathway, (N-recognins), which allows for the degradation of the polypeptide substrate. This discovery is unprecedented, and is contrary to the prevalent view that N-terminal acetylation protects proteins from degradation. The present disclosure is further based, in part, on the discovery that N-terminal acetylation of polypeptides and the Doa10 branch of the N-end rule pathway are involved in various physiological and pathological conditions, including, for example, conditions as diverse as angiogenesis and other aspects of cardiovascular health in mammals. Accordingly, the present disclosure, through the discovery that N-terminal acetylation of Met, Ala, Val, Ser, Thr, Cys, Gly, or Pro residue of a polypeptide, provides a new approach to ameliorating diseases, and provides screening assays for identifying agents that modulate the N-terminal acetylation of a polypeptide; agents identified by such methods; methods of modulating protein degradation by N-terminal acetylation of a polypeptide and the Doa10 branch of the N-end rule pathway; and methods of ameliorating physiological and/or pathological conditions associated with N-terminal acetylation of a polypeptide and the Doa10 branch of the N-end rule pathway.

In one embodiment, the disclosure provides methods for identifying an agent that modulates $N^\alpha$-terminal acetyl transferase-mediated N-end rule pathway-mediated acetylation of an amino terminal (N-terminal) Met, Ala, Val, Ser, Thr, Cys, Gly, or Pro residue of a peptide, by: a) contacting at least one sample comprising a peptide having an N-terminal Met, Ala, Val, Ser, Thr, Cys, Gly, or Pro residue of the peptide, with at least one test agent, under conditions suitable for the N-terminal Met, Ala, Val, Ser, Thr, Cys, Gly, or Pro residue of the peptide to act as a substrate for an N-end rule pathway reaction; b) detecting a change in the N-end rule pathway substrate activity of the N-terminal Met, Ala, Val, Ser, Thr, Cys, Gly, or Pro residue of the peptide in the presence of the test agent as compared to the activity in the absence of the test agent; and c) correlating the change in the N-end rule pathway substrate activity with a modulation of the N-end rule pathway substrate activity, thereby identifying the test agent as an agent that modulates $N^\alpha$-terminal acetyl transferase-mediated N-end rule pathway-mediated acetylation of an amino terminal (N-terminal) Met, Ala, Val, Ser, Thr, Cys, Gly, or Pro residue of the peptide.

In another embodiment, the disclosure provides methods for modulating degradation of a protein by the N-end rule pathway in a cell, including contacting the cell with an agent that that modulates the N'-terminal acetyl transferase-mediated N-end rule pathway-mediated acetylation of an amino terminal (N-terminal) Met, Ala, Val, Ser, Thr, Cys, Gly, or Pro residue of a protein or a proteolytic cleavage product of a protein, wherein the agent alters the $N^\alpha$-terminal acetyl transferase activity in the cell, thereby modulating degradation of the protein.

In another embodiment, the disclosure provides methods for modulating N-terminal acetylation of a peptide having an amino terminal (N-terminal) Met, Ala, Val, Ser, Thr, Cys, Gly, or Pro residue by the N-end rule pathway in an organism, including administering to the organism an agent that that modulates N-end rule pathway-mediated N-terminal acetylation of an N-terminal Met, Ala, Val, Ser, Thr, Cys, Gly, or Pro residue of a peptide, whereby the agent alters N-end rule pathway activity, thereby modulating N-terminal acetylation of a peptide by the N-end rule pathway in the organism.

In another embodiment, the disclosure provides methods for modulating angiogenesis in a subject, including administering to the subject an agent that modulates N-end rule pathway-mediated acetylation of an amino terminal (N-terminal) Met, Ala, Val, Ser, Thr, Cys, Gly, or Pro residue of a peptide, thereby modulating angiogenesis in the subject.

In another embodiment, the disclosure provides methods for modulating susceptibility of a plant to infection by a pathogen, including contacting the plant with an agent that modulates N-end rule pathway-mediated acetylation of an amino terminal (N-terminal) Met, Ala, Val, Ser, Thr, Cys, or Pro residue of a peptide, whereby the agent alters protein degradation in cells of the plant, thereby modulating susceptibility of the plant to infection by the pathogen.

In another embodiment, the disclosure provides methods for ameliorating a disorder associated with protein degradation due to N-end rule pathway activity in a subject, including administering to the subject an agent that modulates the N-end rule pathway-mediated N-terminal acetylation of an amino terminal (N-terminal) Met, Ala, Val, Ser, Thr, Cys, Gly, or Pro residue of a peptide, whereby protein degradation is altered, thereby ameliorating the disorder in the subject.

In another embodiment, the disclosure provides methods for identifying an agent that modulates N-terminal acetylation activity by the N-end rule pathway, including: a) contacting at least one test agent with at least a first cell that expresses a reporter protein including an amino terminal (N-terminal) Met, Ala, Val, Ser, Thr, Cys, Gly, or Pro residue, wherein the half-life of the reporter protein is affected by acetylation of the N-terminal residue of the protein; and b) measuring the level of the reporter protein expressed in the presence as compared to the absence of the test agent, wherein a change in the level of reporter protein expressed is indicative of modulation of N-terminal acetylation activity, thereby identifying an agent that modulates N-terminal acetylation activity by the N-end rule pathway.

DETAILED DESCRIPTION OF THE DISCLOSURE

Figure 1:
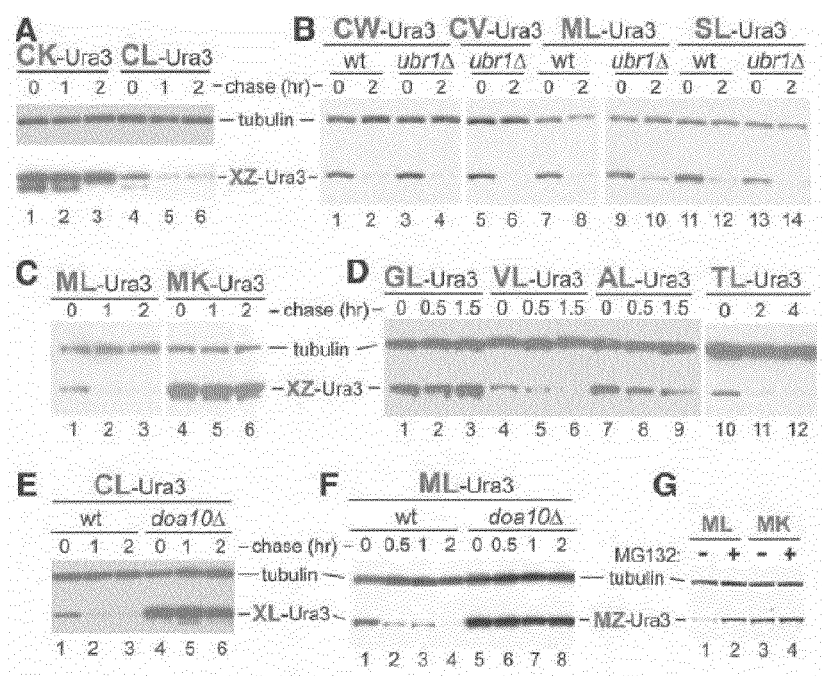
FIG. 1 illustrates the destabilizing N-terminal residues. (A) Cycloheximide (CHX)-chases, for 0, 1 and 2 hr, in wild-type *S. cerevisiae* expressing CK-e$^K$-Ura3 (lanes 1-3) or CL-e$^K$-Ura3 (lanes 4-6). Cell extracts were fractionated by SDS-PAGE, followed by immunoblotting with anti-ha and anti-tubulin antibodies, the latter a loading control. (B) As in A but chases for 0 and 2 hr with XZ-e$^K$-Ura3 (X=Cys, Met, Ser; Z=Trp, Val, Leu) in wild-type versus ubrJΔ cells. (C) As in A but with MZ-e$^K$-Ura3 (Z=Leu, Lys) in wild-type cells. (D) As in A but chases for 0, 0.5 and 1.5 hr with XL-e$^K$-Ura3 (X=Gly, Val, Ala, Thr) in wild-type cells. (E) As in A but with CL-e$^K$-Ura3 in wild-type (lanes 1-3) versus doa10Δ cells (lanes 4-6). (F) As in E but chases for 0, 0.5, 1 and 2 hr with ML-e$^K$-Ura3. (G) Lanes 1 and 2, short-lived ML-e$^K$-Ura in the MG132-sensitive pdr5Δ *S. cerevisiae*, in the absence and presence of MG132, respectively. Lanes 3, 4, same as lanes 1, 2 but with long-lived MK-e$^K$-Ura3.

The present disclosure is based, in part, on the discovery that N-terminal acetylation by a N$^α$-terminal acetyl transferase, of a polypeptide having an amino terminal (N-terminal) Met, Ala, Val, Ser, Thr, Cys, Gly, or Pro residue, creates specific degradation signals (N-degrons) that are targeted by Doa10 E3 Ub ligase, a branch of the ubiquitin-dependent N-end rule pathway (N-recognins), which allows for the degradation of the polypeptide substrate. This discovery is unprecedented, and is contrary to the prevalent view that N-terminal acetylation protects proteins from degradation. The present disclosure is further based, in part, on the discovery that N-terminal acetylation of a polypeptide and the Doa10 branch of the N-end rule pathway are involved in various physiological and pathological conditions, including, for example, conditions as diverse as angiogenesis and other aspects of cardiovascular health in mammals. Accordingly, the present disclosure provides a new approach to ameliorating diseases, and provides screening assays for identifying agents that modulate N-terminal acetylation of a polypeptide and the Doa10 branch of the N-end rule pathway; agents identified by such methods; methods of modulating protein degradation by N-terminal acetylation of a polypeptide and the Doa10 branch of the N-end rule pathway; and methods of ameliorating physiological and/or pathological conditions associated with N-terminal acetylation of a polypeptide and the Doa10 branch of the N-end rule pathway.

In one embodiment, the disclosure provides methods for identifying an agent that modulates N$^α$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, by: a) contacting at least one sample comprising a peptide having an N-terminal Met, Ala, Val, Ser, Thr, Cys, Gly, or Pro residue of the peptide, with at least one test agent, under conditions suitable for the N-terminal Met, Ala, Val, Ser, Thr, Cys, Gly, or Pro residue of the peptide to act as a substrate for an ubiquitin-dependent N-end rule pathway reaction; b) detecting a change in the ubiquitin-dependent N-end rule pathway substrate activity of the N-terminal Met, Ala, Val, Ser, Thr, Cys, Gly, or Pro residue of the peptide in the presence of the test agent as compared to the activity in the absence of the test agent; and c) correlating the change in the ubiquitin-dependent N-end rule pathway substrate activity with a modulation of the ubiquitin-dependent N-end rule pathway substrate activity, thereby identifying the test agent as an agent that modulates N$^α$-terminal acetyl transferase-mediated ubiquitin-dependent N-end rule pathway-mediated acetylation of an amino terminal (N-terminal) Met, Ala, Val, Ser, Thr, Cys, Gly, or Pro residue of the peptide.

In another aspect, the disclosure provides methods for identifying an agent that modulates N$^α$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the peptide comprises a regulator of G protein signaling (RGS) protein.

In another aspect, the disclosure provides methods for identifying an agent that modulates N$^α$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the peptide comprises a synthetic peptide.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the peptide comprises an N-terminal portion of a fusion protein.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the peptide comprises an N-terminal portion of a fusion protein, and wherein the fusion protein comprises a reporter polypeptide C-terminal to the peptide.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the peptide comprises an N-terminal portion of a fusion protein, wherein the fusion protein comprises a reporter polypeptide C-terminal to the peptide, and wherein the reporter polypeptide comprises a selectable marker protein or a detectable label.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the peptide comprises an N-terminal portion of a fusion protein, wherein the fusion protein comprises a reporter polypeptide C-terminal to the peptide, wherein the reporter polypeptide comprises a selectable marker protein or a detectable label, and wherein the selectable marker protein is an antibiotic resistance protein.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the peptide comprises an N-terminal portion of a fusion protein, wherein the fusion protein comprises a reporter polypeptide C-terminal to the peptide, wherein the reporter polypeptide comprises a selectable marker protein or a detectable label, and wherein the detectable label comprises a fluorescent protein, a luminescence generating protein, or an enzyme.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the peptide comprises an N-terminal portion of a fusion protein, wherein the fusion protein comprises a reporter polypeptide C-terminal to the peptide, wherein the reporter polypeptide comprises a selectable marker protein or a detectable label, wherein the detectable label comprises a fluorescent protein, a luminescence generating protein, or an enzyme, and wherein the fluorescent protein is Aequorea green fluorescent protein, the luminescence generating protein is luciferase, or the enzyme is β-galactosidase.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the peptide comprises an N-terminal portion of a fusion protein, and wherein the fusion protein is inducible.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the peptide having Met, Ala, Val, Ser, Thr, Cys, Gly, or Pro residue comprises an internal portion of a protein, and wherein the method further includes contacting the protein with a protease that cleaves the protein to generate the amino terminal (N-terminal) Met, Ala, Val, Ser, Thr, Cys, Gly, or Pro residue of the peptide.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the test agent alters N-terminal acetylation of the amino terminal (N-terminal) Met, Ala, Val, Ser, Thr, Cys, Gly, or Pro residue of the peptide.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the test agent alters N-terminal acetylation of the amino terminal (N-terminal) Met, Ala, Val, Ser, Thr, Cys, Gly, or Pro residue of the peptide, and wherein the test agent reduces or inhibits N-terminal acetylation of the amino terminal (N-terminal) Met, Ala, Val, Ser, Thr, Cys, Gly, or Pro residue of the peptide.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the test agent alters the N-terminal acetylation of the amino terminal (N-terminal) Met, Ala, Val, Ser, Thr, Cys, Gly, or Pro residue of the peptide by an $N^\alpha$-terminal acetyl transferase.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the test agent alters the N-terminal acetylation of the amino terminal (N-terminal) Met, Ala, Val, Ser, Thr, Cys, Gly, or Pro residue of the peptide by an $N^\alpha$-terminal acetyl transferase, and wherein the $N^\alpha$-terminal acetyl transferase includes a mammalian $N^\alpha$-terminal acetyl transferase.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the sample includes a cell-free sample.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the sample includes a cell, or an extract of a cell.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the sample includes a cell, or an extract of a cell, wherein the cell is a cell of a plant or a cell of an animal.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the sample includes a cell, or an extract of a cell, wherein the cell expresses an $N^\alpha$-terminal acetyl transferase.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the sample includes a cell, or an extract of a cell, wherein the cell expresses an $N^\alpha$-terminal acetyl transferase, wherein the $N^\alpha$-terminal acetyl transferase is endogenous to the cell.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein detecting a change in the ubiquitin-dependent N-end rule pathway substrate activity of the amino terminal (N-terminal) Met, Ala, Val, Ser, Thr, Cys, Gly, or Pro residues of the peptide includes measuring the N-terminal acetylation of the amino terminal (N-terminal) Met, Ala, Val, Ser, Thr, Cys, Gly, or Pro residues of the peptide.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein detecting a change in the ubiquitin-dependent N-end rule pathway substrate activity of the N-terminal Met, Ala, Val, Ser, Thr, Cys, Gly, or Pro residues of the peptide is performed using mass spectroscopy or capillary electrophoresis.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, which is performed in a high throughput format.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, which is performed in a high throughput format, including contacting each of a plurality of samples with at least one test agent.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, which is performed in a high throughput format, including contacting each of a plurality of samples with at least one test agent, wherein samples of the plurality of samples are different.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, which is performed in a high throughput format, including contacting each of a plurality of samples with at least one test agent, wherein samples of the plurality are the same, the method including the samples with different test agents.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, which is performed in a high throughput format, including contacting each of a plurality of samples with at least one test agent, wherein samples of the plurality are the same, the method including the samples with different test agents, wherein the different test agents include agents of a library of test agents.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, which is performed in a high throughput format, including contacting each of a plurality of samples with at least one test agent, wherein samples of the plurality are the same, the method including the samples with different test agents, wherein the different test agents include agents of a library of test agents, wherein the library of test agents includes a combinatorial library of test agents.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, which is performed in a high throughput format, including contacting each of a plurality of samples with at least one test agent, wherein samples of the plurality are the same, the method including the samples with different test agents, wherein the different test agents include agents of a library of test agents, wherein the combinatorial library includes a random library, a biased library, or a variegated library of test agents.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the sample includes a cell, or an extract of a cell, wherein the cell is a cell of a plant or a cell of an animal, wherein the plant is infected with a pathogen.

In another aspect, the disclosure provides methods for identifying an agent that modulates $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide, wherein the sample includes a cell, or an extract of a cell, wherein the cell is a cell of a plant or a cell of an animal, wherein the animal has a disorder associated with abnormal protein degradation.

In another aspect, the disclosure provides an agent identified by modulating $N^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a peptide.

In another embodiment, the disclosure provides methods for modulating degradation of a protein by the ubiquitin-dependent N-end rule pathway in a cell, including contacting the cell with an agent that that modulates the N$^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a protein or a proteolytic cleavage product of a protein, wherein the agent alters the N$^\alpha$-terminal acetyl transferase activity in the cell, thereby modulating degradation of the protein.

In another aspect, the disclosure provides methods for modulating degradation of a protein by the ubiquitin-dependent N-end rule pathway in a cell, including contacting the cell with an agent that that modulates the N$^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a protein or a proteolytic cleavage product of a protein, wherein the agent alters the N$^\alpha$terminal acetyl transferase activity in the cell, thereby modulating degradation of the protein, wherein the agent increases the N$^\alpha$-terminal acetyl transferase activity or level thereof.

In another aspect, the disclosure provides methods for modulating degradation of a protein by the ubiquitin-dependent N-end rule pathway in a cell, including contacting the cell with an agent that that modulates the N$^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a protein or a proteolytic cleavage product of a protein, wherein the agent alters the N$^\alpha$-terminal acetyl transferase activity in the cell, thereby modulating degradation of the protein, wherein the agent reduces or inhibits the N$^\alpha$-terminal acetyl transferase activity or level thereof.

In another aspect, the disclosure provides methods for modulating degradation of a protein by the ubiquitin-dependent N-end rule pathway in a cell, including contacting the cell with an agent that that modulates the N$^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a protein or a proteolytic cleavage product of a protein, wherein the agent alters the N$^\alpha$-terminal acetyl transferase activity in the cell, thereby modulating degradation of the protein, which includes contacting the cell with the agent in vivo.

In another aspect, the disclosure provides methods for modulating degradation of a protein by the ubiquitin-dependent N-end rule pathway in a cell, including contacting the cell with an agent that that modulates the N$^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a protein or a proteolytic cleavage product of a protein, wherein the agent alters the N$^\alpha$-terminal acetyl transferase activity in the cell, thereby modulating degradation of the protein, wherein the cell is a plant cell or an animal cell.

In another aspect, the disclosure provides methods for modulating degradation of a protein by the ubiquitin-dependent N-end rule pathway in a cell, including contacting the cell with an agent that that modulates the N$^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a protein or a proteolytic cleavage product of a protein, wherein the agent alters the N$^\alpha$-terminal acetyl transferase activity in the cell, thereby modulating degradation of the protein, wherein the cell is a plant cell infected with a pathogen.

In another aspect, the disclosure provides methods for modulating degradation of a protein by the ubiquitin-dependent N-end rule pathway in a cell, including contacting the cell with an agent that that modulates the N$^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a protein or a proteolytic cleavage product of a protein, wherein the agent alters the N$^\alpha$-terminal acetyl transferase activity in the cell, thereby modulating degradation of the protein, wherein the agent increases the N$^\alpha$-terminal acetyl transferase activity or level thereof, which includes spraying the agent onto a plant including the plant cell infected with the pathogen.

In another aspect, the disclosure provides methods for modulating degradation of a protein by the ubiquitin-dependent N-end rule pathway in a cell, including contacting the cell with an agent that that modulates the N$^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a protein or a proteolytic cleavage product of a protein, wherein the agent alters the N$^\alpha$-terminal acetyl transferase activity in the cell, thereby modulating degradation of the protein, wherein the agent reduces or inhibits the N$^\alpha$-terminal acetyl transferase activity or level thereof, wherein the cell is a mammalian cell.

In another aspect, the disclosure provides methods for modulating degradation of a protein by the ubiquitin-dependent N-end rule pathway in a cell, including contacting the cell with an agent that that modulates the N$^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a protein or a proteolytic cleavage product of a protein, wherein the agent alters the N$^\alpha$-terminal acetyl transferase activity in the cell, thereby modulating degradation of the protein, wherein the agent reduces or inhibits the N$^\alpha$-terminal acetyl transferase activity or level thereof, wherein the cell includes a neuronal cell, a smooth muscle cell, or a cardiac muscle cell.

In another aspect, the disclosure provides methods for modulating degradation of a protein by the ubiquitin-dependent N-end rule pathway in a cell, including contacting the cell with an agent that that modulates the N$^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a protein or a proteolytic cleavage product of a protein, wherein the agent alters the N$^\alpha$-terminal acetyl transferase activity in the cell, thereby modulating degradation of the protein, wherein the agent reduces or inhibits the N$^\alpha$-terminal acetyl transferase activity or level thereof, wherein the agent is administered to a subject, whereby the agent contacts the cell.

In another aspect, the disclosure provides methods for modulating degradation of a protein by the ubiquitin-dependent N-end rule pathway in a cell, including contacting the cell with an agent that that modulates the N$^\alpha$-terminal acetyl transferase-mediated ubiquitin-dependent N-end rule pathway-mediated acetylation of an amino terminal (N-terminal) Met, Ala, Val, Ser, Thr, Cys, Gly, or Pro residue of a protein or a proteolytic cleavage product of a protein, wherein the agent alters the N$^\alpha$-terminal acetyl transferase activity in the cell, thereby modulating degradation of the protein, wherein the agent reduces or inhibits the N$^\alpha$-terminal acetyl transferase activity or level thereof, including contacting the cell with the agent in vitro.

In another embodiment, the disclosure provides methods for modulating N-terminal acetylation of a peptide having an amino terminal (N-terminal) Met, Ala, Val, Ser, Thr, Cys, Gly, or Pro residue by the ubiquitin-dependent N-end rule pathway in an organism, including administering to the organism an agent that that modulates ubiquitin-dependent N-end rule pathway-mediated N-terminal acetylation of an N-terminal Met, Ala, Val, Ser, Thr, Cys, Gly, or Pro residue of a peptide, whereby the agent alters ubiquitin-dependent N-end rule pathway activity, thereby modulating N-terminal acetylation of a peptide by the ubiquitin-dependent N-end rule pathway in the organism.

In another aspect, the disclosure provides methods for modulating N-terminal acetylation of a peptide having an amino terminal (N-terminal) Met, Ala, Val, Ser, Thr, Cys, Gly, or Pro residue by the ubiquitin-dependent N-end rule pathway in an organism, including administering to the organism an agent that that modulates ubiquitin-dependent N-end rule pathway-mediated N-terminal acetylation of an N-terminal Met, Ala, Val, Ser, Thr, Cys, Gly, or Pro residue of a peptide, whereby the agent alters ubiquitin-dependent N-end rule pathway activity, thereby modulating N-terminal acetylation of a peptide by the ubiquitin-dependent N-end rule pathway in the organism, wherein the organism is a plant or an animal.

In another aspect, the disclosure provides methods for modulating N-terminal acetylation of a peptide having an amino terminal (N-terminal) Met, Ala, Val, Ser, Thr, Cys, Gly, or Pro residue by the ubiquitin-dependent N-end rule pathway in an organism, including administering to the organism an agent that that modulates ubiquitin-dependent N-end rule pathway-mediated N-terminal acetylation of an N-terminal Met, Ala, Val, Ser, Thr, Cys, Gly, or Pro residue of a peptide, whereby the agent alters ubiquitin-dependent N-end rule pathway activity, thereby modulating N-terminal acetylation of a peptide by the ubiquitin-dependent N-end rule pathway in the organism, wherein the peptide has an amino terminal (N-terminal) Met, Ala, Val, Ser, Thr, Cys, Gly, or Pro residue, and wherein the agent reduces or inhibits $N^\alpha$-terminal acetyl transferase levels or activity.

In another aspect, the disclosure provides methods for modulating N-terminal acetylation of a peptide having an amino terminal (N-terminal) Met, Ala, Val, Ser, Thr, Cys, Gly, or Pro residue by the ubiquitin-dependent N-end rule pathway in an organism, including administering to the organism an agent that modulates ubiquitin-dependent N-end rule pathway-mediated N-terminal acetylation of an N-terminal Met, Ala, Val, Ser, Thr, Cys, Gly, or Pro residue of a peptide, whereby the agent alters ubiquitin-dependent N-end rule pathway activity, thereby modulating N-terminal acetylation of a peptide by the ubiquitin-dependent N-end rule pathway in the organism, wherein the agent includes a polynucleotide encoding a $N^\alpha$-terminal acetyl transferase, and wherein administering the agent includes introducing the polynucleotide into a cell of the subject, whereby the $N^\alpha$-terminal acetyl transferase is expressed.

In another aspect, the disclosure provides methods for modulating N-terminal acetylation of a peptide having an amino terminal (N-terminal) Met, Ala, Val, Ser, Thr, Cys, Gly, or Pro residue by the ubiquitin-dependent N-end rule pathway in an organism, including administering to the organism an agent that that modulates ubiquitin-dependent N-end rule pathway-mediated N-terminal acetylation of an N-terminal Met, Ala, Val, Ser, Thr, Cys, Gly, or Pro residue of a peptide, whereby the agent alters ubiquitin-dependent N-end rule pathway activity, thereby modulating N-terminal acetylation of a peptide by the ubiquitin-dependent N-end rule pathway in the organism, wherein the agent includes a small interfering RNA (siRNA) molecule specific for a polynucleotide encoding a $N^\alpha$-terminal acetyl transferase, and wherein administering the agent includes introducing the siRNA molecule into a cell of the subject, whereby the siRNA reduces or inhibits expression of the polynucleotide encoding the $N^\alpha$-terminal acetyl transferase.

In another aspect, the disclosure provides methods for modulating N-terminal acetylation of a peptide having an amino terminal (N-terminal) Met, Ala, Val, Ser, Thr, Cys, Gly, or Pro residue by the ubiquitin-dependent N-end rule pathway in an organism, including administering to the organism an agent that that modulates ubiquitin-dependent N-end rule pathway-mediated N-terminal acetylation of an N-terminal Met, Ala, Val, Ser, Thr, Cys, Gly, or Pro residue of a peptide, whereby the agent alters ubiquitin-dependent N-end rule pathway activity, thereby modulating N-terminal acetylation of a peptide by the ubiquitin-dependent N-end rule pathway in the organism, wherein the agent is a small molecule chemical compound.

In another aspect, the disclosure provides methods for modulating N-terminal acetylation of a peptide having an amino terminal (N-terminal) Met, Ala, Val, Ser, Thr, Cys, Gly, or Pro residue by the ubiquitin-dependent N-end rule pathway in an organism, including administering to the organism an agent that that modulates ubiquitin-dependent N-end rule pathway-mediated N-terminal acetylation of an N-terminal Met, Ala, Val, Ser, Thr, Cys, Gly, or Pro residue of a peptide, whereby the agent alters ubiquitin-dependent N-end rule pathway activity, thereby modulating N-terminal acetylation of a peptide by the ubiquitin-dependent N-end rule pathway in the organism, wherein the peptide having an amino terminal (N-terminal) Met, Ala, Val, Ser, Thr, Cys, Gly, or Pro residue includes a cellular protein, or a proteolytic cleavage product of the protein.

In another aspect, the disclosure provides methods for modulating N-terminal acetylation of a peptide having an amino terminal (N-terminal) Met, Ala, Val, Ser, Thr, Cys, Gly, or Pro residue by the ubiquitin-dependent N-end rule pathway in an organism, including administering to the organism an agent that that modulates ubiquitin-dependent N-end rule pathway-mediated N-terminal acetylation of an N-terminal Met, Ala, Val, Ser, Thr, Cys, Gly, or Pro residue of a peptide, whereby the agent alters ubiquitin-dependent N-end rule pathway activity, thereby modulating N-terminal acetylation of a peptide by the ubiquitin-dependent N-end rule pathway in the organism, wherein the peptide having an amino terminal (N-terminal) Met, Ala, Val, Ser, Thr, Cys, Gly, or Pro residue includes a cellular protein, or a proteolytic cleavage product of the protein, and wherein the cellular protein includes a caspase.

In another embodiment, the disclosure provides methods for modulating angiogenesis in a subject, including administering to the subject an agent that modulates ubiquitin-dependent N-end rule pathway-mediated acetylation of an amino terminal (N-terminal) Met, Ala, Val, Ser, Thr, Cys, Gly, or Pro residue of a peptide, thereby modulating angiogenesis in the subject.

In another aspect, the disclosure provides methods for modulating angiogenesis in a subject, including administering to the subject an agent that modulates ubiquitin-dependent N-end rule pathway-mediated acetylation of an amino terminal (N-terminal) Met, Ala, Val, Ser, Thr, Cys, Gly, or Pro residue of a peptide, thereby modulating angiogenesis in the subject, wherein the peptide has an amino terminal (N-terminal) Met, Ala, Val, Ser, Thr, Cys, Gly, or Pro residue, and wherein the agent modulates $N^\alpha$-terminal acetyl transferase activity.

In another aspect, the disclosure provides methods for modulating angiogenesis in a subject, including administering to the subject an agent that modulates ubiquitin-dependent N-end rule pathway-mediated acetylation of an amino terminal (N-terminal) Met, Ala, Val, Ser, Thr, Cys, Gly, or Pro residue of a peptide, thereby modulating angiogenesis in the subject, wherein the peptide has an amino terminal (N-terminal) Met, Ala, Val, Ser, Thr, Cys, Gly, or Pro residue, and wherein the agent modulates $N^\alpha$-terminal acetyl transferase activity, wherein the $N^\alpha$-terminal acetyl transferase includes an $N^\alpha$-terminal acetyl transferase gene product.

In another aspect, the disclosure provides methods for modulating angiogenesis in a subject, including administering to the subject an agent that modulates ubiquitin-dependent N-end rule pathway-mediated acetylation of an amino terminal (N-terminal) Met, Ala, Val, Ser, Thr, Cys, Gly, or Pro residue of a peptide, thereby modulating angiogenesis in the subject, wherein the subject is a mammal.

In another aspect, the disclosure provides methods for modulating angiogenesis in a subject, including administering to the subject an agent that modulates ubiquitin-dependent N-end rule pathway-mediated acetylation of an amino terminal (N-terminal) Met, Ala, Val, Ser, Thr, Cys, Gly, or Pro residue of a peptide, thereby modulating angiogenesis in the subject, wherein the angiogenesis is associated with a disorder.

In another aspect, the disclosure provides methods for modulating angiogenesis in a subject, including administering to the subject an agent that modulates ubiquitin-dependent N-end rule pathway-mediated acetylation of an amino terminal (N-terminal) Met, Ala, Val, Ser, Thr, Cys, Gly, or Pro residue of a peptide, thereby modulating angiogenesis in the subject, wherein the angiogenesis is associated with a disorder, wherein the disorder includes cancer, rheumatoid arthritis, psoriasis, coronary artery disease, or stroke.

In another aspect, the disclosure provides methods for modulating angiogenesis in a subject, including administering to the subject an agent that modulates ubiquitin-dependent N-end rule pathway-mediated acetylation of an amino terminal (N-terminal) Met, Ala, Val, Ser, Thr, Cys, Gly, or Pro residue of a peptide, thereby modulating angiogenesis in the subject, wherein the angiogenesis is associated with wound healing.

In another aspect, the disclosure provides methods for modulating angiogenesis in a subject, including administering to the subject an agent that modulates ubiquitin-dependent N-end rule pathway-mediated acetylation of an amino terminal (N-terminal) Met, Ala, Val, Ser, Thr, Cys, Gly, or Pro residue of a peptide, thereby modulating angiogenesis in the subject, wherein the angiogenesis is associated with a tumor.

In another embodiment, the disclosure provides methods for modulating susceptibility of a plant to infection by a pathogen, including contacting the plant with an agent that modulates ubiquitin-dependent N-end rule pathway-mediated acetylation of an amino terminal (N-terminal) Met, Ala, Val, Ser, Thr, Cys, or Pro residue of a peptide, whereby the agent alters protein degradation in cells of the plant, thereby modulating susceptibility of the plant to infection by the pathogen.

In another aspect, the disclosure provides methods for modulating susceptibility of a plant to infection by a pathogen, including contacting the plant with an agent that modulates ubiquitin-dependent N-end rule pathway-mediated acetylation of an amino terminal (N-terminal) Met, Ala, Val, Ser, Thr, Cys, or Pro residue of a peptide, whereby the agent alters protein degradation in cells of the plant, thereby modulating susceptibility of the plant to infection by the pathogen, wherein the pathogen is a bacterial pathogen or a viral pathogen.

In another aspect, the disclosure provides methods for modulating susceptibility of a plant to infection by a pathogen, including contacting the plant with an agent that modulates ubiquitin-dependent N-end rule pathway-mediated acetylation of an amino terminal (N-terminal) Met, Ala, Val, Ser, Thr, Cys, or Pro residue of a peptide, whereby the agent alters protein degradation in cells of the plant, thereby modulating susceptibility of the plant to infection by the pathogen, wherein the pathogen is a bacterial pathogen or a viral pathogen, wherein the pathogen produces a virulence factor, which induces a hypersensitivity response in the plant, and wherein the agent reduces or inhibits $N^\alpha$-terminal acetyl transferase activity in plant.

In another aspect, the disclosure provides methods for modulating susceptibility of a plant to infection by a pathogen, including contacting the plant with an agent that modulates ubiquitin-dependent N-end rule pathway-mediated acetylation of an amino terminal (N-terminal) Met, Ala, Val, Ser, Thr, Cys, or Pro residue of a peptide, whereby the agent alters protein degradation in cells of the plant, thereby modulating susceptibility of the plant to infection by the pathogen, wherein contacting the plant with the agent includes spraying a field containing the plant with the agent.

In another embodiment, the disclosure provides methods for ameliorating a disorder associated with protein degradation due to ubiquitin-dependent N-end rule pathway activity in a subject, including administering to the subject an agent that modulates the ubiquitin-dependent N-end rule pathway-mediated N-terminal acetylation of an amino terminal (N-terminal) Met, Ala, Val, Ser, Thr, Cys, Gly, or Pro residue of a peptide, whereby protein degradation is altered, thereby ameliorating the disorder in the subject.

In another aspect, the disclosure provides methods for ameliorating a disorder associated with protein degradation due to ubiquitin-dependent N-end rule pathway activity in a subject, including administering to the subject an agent that modulates the ubiquitin-dependent N-end rule pathway-mediated N-terminal acetylation of an amino terminal (N-terminal) Met, Ala, Val, Ser, Thr, Cys, Gly, or Pro residue of a peptide, whereby protein degradation is altered, thereby ameliorating the disorder in the subject, wherein the disorder includes a nervous system disorder or a muscular disorder.

In another aspect, the disclosure provides methods for ameliorating a disorder associated with protein degradation due to ubiquitin-dependent N-end rule pathway activity in a subject, including administering to the subject an agent that modulates the ubiquitin-dependent N-end rule pathway-mediated N-terminal acetylation of an amino terminal (N-terminal) Met, Ala, Val, Ser, Thr, Cys, Gly, or Pro residue of a peptide, whereby protein degradation is altered, thereby ameliorating the disorder in the subject, wherein the disorder includes schizophrenia, angina, or impotence.

In another aspect, the disclosure provides methods for ameliorating a disorder associated with protein degradation due to ubiquitin-dependent N-end rule pathway activity in a subject, including administering to the subject an agent that modulates the ubiquitin-dependent N-end rule pathway-mediated N-terminal acetylation of an amino terminal (N-terminal) Met, Ala, Val, Ser, Thr, Cys, Gly, or Pro residue of a peptide, whereby protein degradation is altered, thereby ameliorating the disorder in the subject, wherein the protein, or a proteolytic fragment of the protein, includes an amino terminal (N-terminal) Met, Ala, Val, Ser, Thr, Cys, Gly, or Pro residue, and wherein the agent modulates $N^\alpha$-terminal acetyl transferase levels or activity.

In another embodiment, the disclosure provides methods for identifying an agent that modulates N-terminal acetylation activity by the ubiquitin-dependent N-end rule pathway, including: a) contacting at least one test agent with at least a first cell that expresses a reporter protein including an amino terminal (N-terminal) Met, Ala, Val, Ser, Thr, Cys, Gly, or Pro residue, wherein the half-life of the reporter protein is affected by acetylation of the N-terminal residue of the protein; and b) measuring the level of the reporter protein expressed in the presence as compared to the absence of the test agent, wherein a change in the level of reporter protein expressed is indicative of modulation of N-terminal acetylation activity, thereby identifying an agent that modulates N-terminal acetylation activity by the ubiquitin-dependent N-end rule pathway.

In another aspect, the disclosure provides methods for identifying an agent that modulates N-terminal acetylation activity by the ubiquitin-dependent N-end rule pathway, including: a) contacting at least one test agent with at least a first cell that expresses a reporter protein including an amino terminal (N-terminal) Met, Ala, Val, Ser, Thr, Cys, Gly, or Pro residue, wherein the half-life of the reporter protein is affected by acetylation of the N-terminal residue of the protein; and b) measuring the level of the reporter protein expressed in the presence as compared to the absence of the test agent, wherein a change in the level of reporter protein expressed is indicative of modulation of N-terminal acetylation activity, thereby identifying an agent that modulates N-terminal acetylation activity by the ubiquitin-dependent N-end rule pathway, wherein the cell is a cultured mammalian cell, a yeast cell, or a bacterial cell.

In another aspect, the disclosure provides methods for identifying an agent that modulates N-terminal acetylation activity by the ubiquitin-dependent N-end rule pathway, including: a) contacting at least one test agent with at least a first cell that expresses a reporter protein including an amino terminal (N-terminal) Met, Ala, Val, Ser, Thr, Cys, Gly, or Pro residue, wherein the half-life of the reporter protein is affected by acetylation of the N-terminal residue of the protein; and b) measuring the level of the reporter protein expressed in the presence as compared to the absence of the test agent, wherein a change in the level of reporter protein expressed is indicative of modulation of N-terminal acetylation activity, thereby identifying an agent that modulates N-terminal acetylation activity by the ubiquitin-dependent N-end rule pathway, wherein the reporter protein is expressed as a cleavable fusion protein including a reporter protein and a ubiquitin domain functionally linked to the reporter protein.

In another aspect, the disclosure provides methods for identifying an agent that modulates N-terminal acetylation activity by the ubiquitin-dependent N-end rule pathway, including: a) contacting at least one test agent with at least a first cell that expresses a reporter protein including an amino terminal (N-terminal) Met, Ala, Val, Ser, Thr, Cys, Gly, or Pro residue, wherein the half-life of the reporter protein is affected by acetylation of the N-terminal residue of the protein; and b) measuring the level of the reporter protein expressed in the presence as compared to the absence of the test agent, wherein a change in the level of reporter protein expressed is indicative of modulation of N-terminal acetylation activity, thereby identifying an agent that modulates N-terminal acetylation activity by the ubiquitin-dependent N-end rule pathway, wherein the reporter protein includes a selectable marker protein, a fluorescent protein, a luminescence generating protein, or an enzyme.

In another aspect, the disclosure provides methods for identifying an agent that modulates N-terminal acetylation activity by the ubiquitin-dependent N-end rule pathway, including: a) contacting at least one test agent with at least a first cell that expresses a reporter protein including an amino terminal (N-terminal) Met, Ala, Val, Ser, Thr, Cys, Gly, or Pro residue, wherein the half-life of the reporter protein is affected by acetylation of the N-terminal residue of the protein; and b) measuring the level of the reporter protein expressed in the presence as compared to the absence of the test agent, wherein a change in the level of reporter protein expressed is indicative of modulation of N-terminal acetylation activity, thereby identifying an agent that modulates N-terminal acetylation activity by the ubiquitin-dependent N-end rule pathway, wherein the expression of the reporter protein is inducible.

In another aspect, the disclosure provides methods for identifying an agent that modulates N-terminal acetylation activity by the ubiquitin-dependent N-end rule pathway, including: a) contacting at least one test agent with at least a first cell that expresses a reporter protein including an amino terminal (N-terminal) Met, Ala, Val, Ser, Thr, Cys, Gly, or Pro residue, wherein the half-life of the reporter protein is affected by acetylation of the N-terminal residue of the protein; and b) measuring the level of the reporter protein expressed in the presence as compared to the absence of the test agent, wherein a change in the level of reporter protein expressed is indicative of modulation of N-terminal acetylation activity, thereby identifying an agent that modulates N-terminal acetylation activity by the ubiquitin-dependent N-end rule pathway, wherein the reporter protein has a half-life in the cell of less than about an hour in the absence of the test agent.

In another aspect, the disclosure provides methods for identifying an agent that modulates N-terminal acetylation activity by the ubiquitin-dependent N-end rule pathway, including: a) contacting at least one test agent with at least a first cell that expresses a reporter protein including an amino terminal (N-terminal) Met, Ala, Val, Ser, Thr, Cys, Gly, or Pro residue, wherein the half-life of the reporter protein is affected by acetylation of the N-terminal residue of the protein; and b) measuring the level of the reporter protein expressed in the presence as compared to the absence of the test agent, wherein a change in the level of reporter protein expressed is indicative of modulation of N-terminal acetylation activity, thereby identifying an agent that modulates N-terminal acetylation activity by the ubiquitin-dependent N-end rule pathway, wherein the reporter protein has a half-life in the cell of less than about 10 minutes in the absence of the test agent.

In another aspect, the disclosure provides methods for identifying an agent that modulates N-terminal acetylation activity by the ubiquitin-dependent N-end rule pathway, including: a) contacting at least one test agent with at least a first cell that expresses a reporter protein including an amino terminal (N-terminal) Met, Ala, Val, Ser, Thr, Cys, Gly, or Pro residue, wherein the half-life of the reporter protein is affected by acetylation of the N-terminal residue of the protein; and b) measuring the level of the reporter protein expressed in the presence as compared to the absence of the test agent, wherein a change in the level of reporter protein expressed is indicative of modulation of N-terminal acetylation activity, thereby identifying an agent that modulates N-terminal acetylation activity by the ubiquitin-dependent N-end rule pathway, further including: c) contacting at least a second cell that expresses a second reporter protein, wherein the half-life of the second reporter protein is affected by N-terminal acetylation of the protein, with at least one potential modulator of $N^\alpha$-terminal acetyl transferase gene product activity; and d) measuring the level of second reporter protein expressed within the second cell relative to the level of reporter protein expressed within the first cell.

In another aspect, the disclosure provides methods for identifying an agent that modulates N-terminal acetylation activity by the ubiquitin-dependent N-end rule pathway, including: a) contacting at least one test agent with at least a first cell that expresses a reporter protein including an amino terminal (N-terminal) Met, Ala, Val, Ser, Thr, Cys, Gly, or Pro residue, wherein the half-life of the reporter protein is affected by acetylation of the N-terminal residue of the protein; and b) measuring the level of the reporter protein expressed in the presence as compared to the absence of the test agent, wherein a change in the level of reporter protein expressed is indicative of modulation of N-terminal acetylation activity, thereby identifying an agent that modulates N-terminal acetylation activity by the ubiquitin-dependent N-end rule pathway, further including: c) contacting at least a second cell that expresses a second reporter protein, wherein the half-life of the second reporter protein is affected by N-terminal acetylation of the protein, with at least one potential modulator of $N^\alpha$-terminal acetyl transferase gene product activity; and d) measuring the level of second reporter protein expressed within the second cell relative to the level of reporter protein expressed within the first cell, wherein the first cell and the second cell are the same cell.

In another aspect, the disclosure provides methods for identifying an agent that modulates N-terminal acetylation activity by the ubiquitin-dependent N-end rule pathway, including: a) contacting at least one test agent with at least a first cell that expresses a reporter protein including an amino terminal (N-terminal) Met, Ala, Val, Ser, Thr, Cys, Gly, or Pro residue, wherein the half-life of the reporter protein is affected by acetylation of the N-terminal residue of the protein; and b) measuring the level of the reporter protein expressed in the presence as compared to the absence of the test agent, wherein a change in the level of reporter protein expressed is indicative of modulation of N-terminal acetylation activity, thereby identifying an agent that modulates N-terminal acetylation activity by the ubiquitin-dependent N-end rule pathway, wherein the agent that modulates N-terminal acetylation activity modulates angiogenesis.

The present disclosure provides methods of identifying agents that modulate N-terminal acetylation of a polypeptide and the Doa10 branch of the N-end rule pathway. As used herein, the term "modulate" means change or alter. As such, an agent that modulates, for example, can act to increase or to reduce or inhibit the activity of an $N^\alpha$-terminal acetyl transferase, i.e. the N-terminal acetylation of a polypeptide having an amino terminal (N-terminal) Met, Ala, Val, Ser, Thr, Cys, Gly, or Pro residue. The terms "reduce" and "inhibit" are used together because it is recognized, for example, that an agent may reduce $N^\alpha$-terminal acetyl transferase activity below a level that is detectable by a particular assay being used and, therefore, that it may not be possible to determine from the assay whether the activity is completely inhibited. Nevertheless, the ability of an agent to reduce or inhibit the activity of N-terminal acetylation of a polypeptide and the Doa10 branch of the N-end rule pathway, including at any level of the pathway, will be readily apparent upon comparison of the particular activity in the presence and absence of the agent (or test agent).

The methods of the disclosure provide screening assays useful for determining whether a test agent can modulate N-terminal acetylation of a polypeptide and the Doa10 branch of the N-end rule pathway, and therefore, the rate or amount of protein degradation that occurs in a sample (e.g., a cell). As used herein, the term "test agent" means any compound that is being examined for the ability to modulate N-terminal acetylation of a polypeptide and the Doa10 branch of the N-end rule pathway. A test agent (and an agent that modulates N-terminal acetylation) can be any type of molecule, including, for example a peptide, a polynucleotide, an antibody, a glycoprotein, a carbohydrate, a small organic molecule, or a peptidomimetic.

The term "polynucleotide" is used broadly herein to mean a sequence of two or more deoxyribonucleotides or ribonucleotides that are linked together by a phosphodiester bond. As such, the term "polynucleotide" includes RNA and DNA, which can be an isolated naturally occurring polynucleotide or portion thereof or a synthetic polynucleotide; can be single stranded or double stranded, as well as a DNA/RNA hybrid; and can encode one or more peptide(s) or can have (or encode a second polynucleotide) having an activity (e.g., an antisense molecule, a ribozyme, a small interfering RNA (siRNA), and the like). A polynucleotide agent (or test agent) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., Nucl. Acids Res. 22:5220-5234, 1994; Jellinek et al., Biochemistry 34:11363-11372, 1995; Pagratis et al., Nature Biotechnol. 15:68-73, 1997, each of which is incorporated herein by reference).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (Tam et al., Nucl. Acids Res. 22:977-986, 1994; Ecker and Crooke, BioTechnology 13:351360, 1995, each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide agent (test agent) comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

Peptides also can be useful as test agents. The term "peptide" is used broadly herein to refer to a molecule containing two or more amino acids or amino acid analogs (or modified forms thereof) linked by peptide bonds. As such, peptide test agents (or agents) can contain one or more D-amino acids and/or L-amino acids; and/or one or more amino acid analogs, for example, an amino acid that has been derivatized or otherwise modified at its reactive side chain. In addition, one or more peptide bonds in the peptide can be modified, and a reactive group at the amino terminus or the carboxy terminus or both can be modified. Peptides containing D-amino acids, or L-amino acid analogs, or the like, can have improved stability to a protease, an oxidizing agent or other reactive material the peptide may encounter in a biological environment. Further, the stability of a peptide agent (or test agent) can be improved by generating (or linking) a fusion protein comprising the peptide and a second polypeptide (e.g., an Fc domain of an antibody) that increases the half-life of the peptide agent in vivo. Peptides also can be modified to have decreased stability in a biological environment, if desired, such that the period of time the peptide is active in the environment is reduced. In this respect, it is recognized that certain screening assays of the disclosure can utilize a peptide having, for example, an amino terminal (N-terminal) Met, Ala, Val, Ser, Thr, Cys, Gly, or Pro residue. Such peptides can have any of the above-described characteristics (e.g., can contain one or more D-amino acid residues), provided the peptide maintains the ability to act as a substrate for a step in the ubiquitin-dependent N-end rule pathway being examined (e.g., as a substrate for the N-terminal acetylation of a polypeptide and the Doa10 branch of the N-end rule pathway).

Antibodies provide an example of peptides useful as test agents in a screening assay of the disclosure. As used herein, the term "antibody" is used in its broadest sense to include polyclonal and monoclonal antibodies, as well as antigen binding fragments of such antibodies. Antibodies are characterized, in part, in that they specifically bind to an antigen, particularly to one or more epitopes of an antigen. The term "binds specifically" or "specific binding activity" or the like, when used in reference to an antibody, means that an interaction of the antibody and a particular epitope has a dissociation constant of at least about $1 \times 10^{-6}$ M, generally at least about $1 \times 10^{-7}$ M, usually at least about $1 \times 10^{-8}$ M, and particularly at least about $1 \times 10^{-9}$ M or $1 \times 10^{-10}$ M or less. As such, Fab, F(ab')$_2$, Fd and Fv fragments of an antibody that retain specific binding activity are included within the definition of an antibody.

The term "antibody" as used herein includes naturally occurring antibodies as well as non-naturally occurring antibodies, including, for example, single chain antibodies, chimeric, bifunctional and humanized antibodies, as well as antigen-binding fragments thereof, such antibodies providing the advantage that they can be relatively small in size and, therefore, more conveniently made and/or used. Such non-naturally occurring antibodies can be constructed using solid phase peptide synthesis, can be produced recombinantly or can be obtained, for example, by screening combinatorial libraries consisting of variable heavy chains and variable light chains (Huse et al., Science 246:1275-1281, 1989, which is incorporated herein by reference). These and other methods of making, for example, chimeric, humanized, CDR-grafted, single chain, and bifunctional antibodies are well known (Winter and Harris, Immunol. Today 14:243-246, 1993; Ward et al., Nature 341:544-546, 1989; Harlow and Lane, Antibodies: A laboratory manual (Cold Spring Harbor Laboratory Press, 1999); Hilyard et al., Protein Engineering: A practical approach (IRL Press 1992); Borrabeck, Antibody Engineering, 2d ed. (Oxford University Press 1995); each of which is incorporated herein by reference).

A screening assay of the disclosure can be practiced by contacting a sample that contains (or to which can be added) components that are necessary and sufficient for the one or more steps involving N-terminal acetylation of a polypeptide and the Doa10 branch of the N-end rule pathway. Such conditions are exemplified herein in the Examples, and includes, for instance, appropriate buffer conditions (including pH), salt concentration (e.g., physiological), and other conditions, which can be selected based on whether the assay is performed in a cell free format or is performed in a cell based assay.

As disclosed herein, a screening assay of the disclosure can be performed in vitro (e.g., in a cell free system using purified or partially purified components) or in a cell (e.g., in a cell or tissue culture system). Where the method is performed in vitro, the components of the N-terminal acetylation of a polypeptide and the Doa10 branch of the N-end rule pathway being examined, e.g. $N^\alpha$-terminal acetyl transferase, may be obtained, for example, from an extract of a cell expressing the transferase, or can be a synthetic transferase prepared, for example, using an in vitro translation or coupled transcription/translation reaction using a polynucleotide encoding the transferase gene sequence. Where the method is performed as a cell based assay, the sample can be a cell sample, wherein the component(s) involved in the N-terminal acetylation of a polypeptide and the Doa10 branch of the N-end rule pathway is expressed in the cell. Further, the cell can be one in which the component(s) is expressed in nature in the cell (e.g., a muscle cell expressing an $N^\alpha$-terminal acetyl transferase), or can be a cell that has been genetically modified to express a polynucleotide encoding the component (e.g., a eukaryotic cell such as a yeast cell, a *Xenopus oocyte*, a mouse fibroblast, or the like).

In one aspect, the screening assays of the disclosure provide a means to identify an agent that modulates (e.g., reduces or inhibits) N-terminal acetylation of a polypeptide and the Doa10 branch of the N-end rule pathway. Such an assay can be performed using mammalian cells in culture or yeast (*S. cerevisiae*) cells in culture. In mammalian cells and yeast, $N^\alpha$-terminal acetyl transferases are responsible for N-terminal acetylation. An advantage of a yeast-based screen is the ease of handling and analyzing yeast cell cultures. However, a disadvantage of yeast is that potential inhibitors of $N^\alpha$-terminal acetyl transferase that would be able cross the plasma membrane of mammalian cells may be incapable of gaining entry into yeast cells, given substantial differences in the permeability (and transport) properties of the plasma membrane between yeast and mammals. A mammalian cell-based screen avoids such a potential problem where the agent to be identified is be used in mammals. A mammalian (mouse or human) cell line can be used that is genetically modified to express a short-lived reporter whose ubiquitin-dependent N degradation by the ubiquitin-dependent N-end rule pathway involves N-terminal acetylation. Such a reporter can be a protein, including, for example, a genetically selectable or a visually detectable reporter.

A number of classes of reporter proteins are suitable for use with the methods of the disclosure. For example, the reporter protein can be a genetically selectable marker protein, and the relative level of the reporter protein in the presence and absence of a test agent can accomplished indirectly through a selective genetic screen that requires the presence of said reporter protein for survival of the first cell. In such an example, an agent that modulates (e.g., inhibits) $N^\alpha$-terminal acetyl transferase activity, for example, would lengthen the half-life of the reporter protein. For example, the selectable marker protein can be an antibiotic resistance protein. In one such example, the reporter protein is designed to be short-lived in a cell, the cell will be relatively sensitive to the relevant antibiotic. By contrast, if the protein is made long-lived in vivo, for example through the inhibition of a proteolytic pathway (e.g., through inhibition of $N^\alpha$-terminal acetyl transferase activity) that normally destroys this protein, its steady-state level would increase, and the cell would become resistant to the same dose of antibiotic. This readout would enable a selection-based screen. A number of reporter proteins that confer antibiotic resistance are known to those skilled in the art.

Detection of the relative abundance of the reporter protein also can be accomplished by more direct means. For example, the reporter protein can be a screenable reporter protein. Such proteins include, but are not limited to, green fluorescent protein (GFP) and *E. coli* β-galactosidase (β-gal), and, when expressed in a cell, can be detected either through their fluorescence (GFP) or their enzymatic activity (βgal). The suitable reporter protein can be expressed in the cell type used for the assay and has sufficient intensity or activity to be detected within the cell at the appropriate concentrations. Making a reporter of this class short-lived in vivo can strongly diminish its steady-state level in a cell. If degradation of such a short-lived reporter is inhibited, its steady-state level will rise, enabling the detection of reporter. The level of fluorescent protein can be determined using fluorescence detection, for example, using a fluorimeter or fluorescence microscope. The relative amount of fluorescence can be compared between cells treated with a test agent and untreated cells (or cells treated with a molecule that is similar to the test agent but otherwise known to be inactive). Additional reporter proteins include, for example, a light-generating protein such as luciferase, wherein the amount of light produced can be measured and compared in cells treated with a test agent and in untreated cells, which can be the same cells as those treated with the test agent, but examined prior to addition of the test agent.

The level of reporter protein present can also be determined enzymatically. For example, enzymes capable of making a calorimetric change in a substrate, can be detected indirectly. For example, *E. coli* β-galactosidase (β-gal) can be detected through a calorimetric change it causes in the substrate X-gal (5-bromo-4-chloro-3-indolyl-β-D-galactosidase). Making a reporter of this class short-lived in vivo would strongly diminish its steady-state level in a cell. If degradation of such a short-lived reporter is inhibited, its steady-state level will rise, enabling the detection of the reporter protein (through an enzymatic reaction).

The present disclosure provides methods of identifying agents that modulate N-terminal acetylation of a polypeptide and the Doa10 branch of the N-end rule pathway. As used herein, the term "modulate" means change or alter. As such, an agent that modulates, for example, can act to increase or to reduce or inhibit the activity of an $N^\alpha$-terminal acetyl transferase, i.e. the N-terminal acetylation of a polypeptide having an amino terminal (N-terminal) Met, Ala, Val, Ser, Thr, Cys, Gly, or Pro residue, Test agents (e.g., of a library of test agents) and/or agents that are tentatively identified as having a desired modulating activity (e.g., reducing or inhibiting $N^\alpha$-terminal acetyl transferase activity) can be further examined, if desired, in control assays to confirm that they act by inhibiting N-terminal acetylation of a polypeptide having an amino terminal (N-terminal) Met, Ala, Val, Ser, Thr, Cys, Gly, or Pro residue. Confirmation of inhibition of $N^\alpha$-terminal acetyl transferase can be obtained in any of several ways. For example, confirmation can be made using an in vivo system or direct enzymatic assays.

Where a test agent is identified as having ubiquitin-dependent N-end rule pathway modulating activity, a screening assay of the disclosure can further include a step of determining an amount by which the agent increases or decreases N-terminal acetylation of a polypeptide and/or protein degradation. For example, where an agent is identified that reduces or inhibits ubiquitin-dependent N-end rule pathway-mediated acetylation activity in a cell, a method of the disclosure can further include determining an amount by which the agent decreases the activity below a desired level (e.g., below detection of the particular method used to measure the activity). Such an agent can be identified by measuring the amount of ubiquitin-dependent N-end rule pathway-mediated acetylation of a substrate peptide both before adding the test agent and after adding the test agent, or can be identified for example, using two samples, wherein one sample serves as a control (no test agent added) and the other sample includes the test agent. As such, a method of the disclosure provides a means to obtain agents or panels of agents that variously modulate ubiquitin-dependent N-end rule pathway-mediated acetylation activity, including protein degradation dependent on the pathway.

A screening assay of the disclosure also provides a means to determine an amount of a particular agent useful for effecting a desired level of activity of the N-terminal acetylation of a polypeptide and the Doa10 branch of the N-end rule pathway. Such a method can be performed by contacting aliquots of a sample with different amounts of the same or different test agents or different amounts of the same or different agents previously identified as having ubiquitin-dependent N-end rule pathway modulating activity. As such, the methods of the disclosure can be used to confirm that an agent believed to have a particular activity, in fact, has the activity, thus providing a means, for example, to standardize the activity of the agent.

The screening method of the disclosure is readily adaptable to high throughput format, thus allowing for the screening, in parallel, of one or more test agents using one or more samples, wherein the agents and/or samples independently are the same or different. As such, the method allows for testing one or more concentrations of one or more test agents to identify a concentration of an agent particularly useful for modulating the activity of N-terminal acetylation of a polypeptide and the Doa10 branch of the N-end rule pathway, including agents that act at various steps of the pathway (e.g. $N^\alpha$-terminal acetyl transferase or ubiquitinylation by Doa10 E3Ub ligase of the substrate peptide). Further, the method allows for examining several same test agents on one or a plurality of same samples, thus providing a means to obtain statistically significant results. In various aspects, the high throughput format can be used for screening one or a plurality of cell sample(s), for example, samples taken from a subject having a physiological or pathological disorder associated with the N-terminal acetylation of a polypeptide and the Doa10 branch of the N-end rule pathway (e.g., impotence, or schizophrenia), with one or a plurality of the same (e.g., different concentrations) or different test agents, to identify an agent and/or concentration of agent that is best suited for modulating the pathway and ameliorating the disorder.

When performed in a high throughput (or ultra-high throughput) format, the method can be performed on a solid support (e.g., a microtiter plate, a silicon wafer, or a glass slide), wherein samples to be contacted with a test agent are positioned such that each is delineated from each other (e.g., in wells). Any number of samples (e.g., 96, 1024, 10,000, 100,000, or more) can be examined in parallel using such a method, depending on the particular support used. Where samples are positioned in an array (i.e., a defined pattern), each sample in the array can be defined by its position (e.g., using an x-y axis), thus providing an "address" for each sample. An advantage of using an addressable array format is that the method can be automated, in whole or in part, such that reagents (e.g., test agents) can be dispensed in (or removed from) specified positions at desired times, and samples (or aliquots) can be monitored for the desired activity.

When used in a high throughput format, a method of the disclosure provides a means to conveniently screen combinatorial libraries of test agents, which can be a library of random test agents, biased test agents (see, for example, U.S. Pat. No. 5,264,563, which is incorporated herein by reference), or variegated test agents (see, for example, U.S. Pat. No. 5,571, 698, which is incorporated herein by reference), in order to identify those agents that can modulate the activity of N-terminal acetylation of a polypeptide and the Doa10 branch of the N-end rule pathway. Methods for preparing a combinatorial library of molecules that can be screened for such modulating activity are well known in the art and include, for example, methods of making a phage display library of peptides, which can be constrained peptides (see, for example, U.S. Pat. No. 5,622,699; U.S. Pat. No. 5,206,347; Scott and Smith, Science 249:386-390, 1992; Markland et al., Gene 109:13 19, 1991; each of which is incorporated herein by reference); a peptide library (see, U.S. Pat. No. 5,264,563, which is incorporated herein by reference); a library of peptide derivative compounds such as a hydroxamate compound library, reverse hydroxamate compound library, a carboxylate compound library, thiol compound library, a phosphinic peptide library, or phosphonate compound library (see, for example, Dive et al., Biochem. Soc. Trans. 28:455-460, 2000; Ye and Marshall, "Peptides: The Wave of the Future" Lebl and Houghten, ed.; American Peptide Society, 2001, each of which is incorporated herein by reference); a peptidomimetic library (see Blondelle et al., Trends Anal. Chem. 14:83 92, 1995, which is incorporated herein by reference); a nucleic acid library (see O'Connell et al., Proc. Natl. Acad. Sci., USA 93:5883-5887, 1996; Tuerk and Gold, Science 249:505-510, 1990; Gold et al., Ann. Rev. Biochem. 64:763-797, 1995; each of which is incorporated herein by reference); an oligosaccharide library (see York et al., Carb. Res. 285:99-128, 1996; Liang et al., Science 274:1520 1522, 1996; Ding et al., Adv. Expt. Med. Biol. 376:261269, 1995; each of which is incorporated herein by reference); a lipoprotein library (see de Kruif et al., FEBS Lett. 399:232 236, 1996, which is incorporated herein by reference); a glycoprotein or glycolipid library (see Karaoglu et al., J. Cell Biol. 130:567 577, 1995, which is incorporated herein by reference); or a chemical library containing, for example, drugs or other pharmaceutical agents, e.g., small organic molecules having a molecular weight of about 1000 daltons (Da) or less (see, for example, see Gordon et al., J. Med. Chem. 37:1385-1401, 1994; Ecker and Crooke, BioTechnology 13:351-360, 1995; each of which is incorporated herein by reference).

Modulation of the N-terminal acetylation of the Doa10 branch of the N-end rule pathway provides a means to manipulate the physiology of a subject and to ameliorate abnormal physiological conditions and/or pathologic conditions in the subject. Accordingly, agents that modulate N-terminal acetylation of a polypeptide and the Doa10 branch of the N-end rule pathway, including agents identified by the screening assays of the disclosure, can be useful as a medicament for treating various physiological and pathological conditions in animals, including mammals (e.g., humans). The animal subject to be treated can be any organism that has a condition that can be manipulated by modulating N-terminal acetylation of a polypeptide and the Doa10 branch of the N-end rule pathway, and generally is a mammalian organism, particularly a human. Conditions amenable to treatment using an agent that modulates N-terminal acetylation of a polypeptide and the Doa10 branch of the N-end rule pathway can include, for example, conditions in which it is desired to increase or decrease angiogenesis (e.g., cancer and other tumor growth, including metastasis of cancer cells; rheumatoid arthritis, psoriasis, rosacea; coronary artery disease; stroke; and wound healing); conditions that are treated using drugs that have the effect of increasing or decreasing nitric oxide levels in the subject (e.g., impotence, which is treated, for example, with sildenafil citrate (Viagra™); and angina, which is treated with nitroglycerin); conditions characterized by abnormal levels of apoptosis (e.g., cancer); and other conditions characterized by altered levels or activities associated with N-terminal acetylation of a polypeptide and the Doa10 branch of the N-end rule pathway including components such as $N^{\alpha}$-terminal acetyl transferase levels or activity (e.g., schizophrenia, in which increased activity of the N-terminal acetylation of the Doa10 branch of the N-end rule pathway can cause the decreased levels of RGS4 associated with the disorder).

As disclosed herein, N-terminal acetylation of a polypeptide and the Doa10 branch of the N-end rule pathway may be involved in various physiological and pathological conditions and, therefore, can be modulated in order to alter such physiological and/or pathological conditions as desired. As such, the disclosure provides methods of ameliorating a condition or disorder associated with the N-terminal acetylation of a polypeptide and the of the Doa10 branch of the N-end rule pathway, including, for example, conditions associated with abnormal levels of protein degradation. As used herein, the term "ameliorate" means that signs and/or symptoms of a pathologic condition are reduced (lessened). Such a method can be performed by administering to the subject an agent that modulates N-terminal acetylation of a polypeptide and the Doa10 branch of the N-end rule pathway.

Amelioration of a condition can be identified using any assay generally used to monitor the clinical signs or the symptoms of the particular condition. For example, amelioration of a wound can be identified by monitoring closure or healing of the wound, and amelioration of a cancer can be identified by detecting reduced angiogenesis and/or vascularization of a tumor, or by detecting a change in the level of apoptosis occurring in the cancer cells following administration of the agent. In addition, amelioration can be identified by the subject indicating that the treatment with an agent is effective, for example, in treating impotence or angina.

Where the agent is to be used for a therapeutic method, it can be formulated in a form suitable for administration to a subject, for example, as a pill or a liquid, and can be administered, for example, orally, by injection, or via inhalation. Accordingly, compositions, including medicaments, useful for treating a subject having a condition amenable to treatment using an agent that modulates the activity of N-terminal acetylation of a polypeptide and the Doa10 branch of the N-end rule pathway are provided. A composition for administration to a living subject generally includes formulating the agent in a pharmaceutically acceptable composition. Such compositions are well known in the art and include, for example, aqueous solutions such as water or physiologically buffered saline or other solvents or vehicles such as glycols, glycerol, oils such as olive oil or injectable organic esters. The composition also can contain physiologically acceptable compounds that act, for example, to stabilize or to increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients.

One skilled in the art would know that the choice of a composition, including a physiologically acceptable compound, depends, for example, on the physico-chemical characteristics of the agent to be administered, and on the route of administration of the composition, which can be, for example, orally or parenterally such as intravenously, and by injection, intubation, inhalation, or other such method known in the art. The composition also can contain one or more additional reagents, including, for example, nutrients or vitamins or, where the composition is administered for a therapeutic purpose, a diagnostic reagent or therapeutic agent relevant to the disorder being treated.

The composition can be administered to a subject by any of various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the composition can be administered by injection, intubation, orally or topically, the latter of which can be passive, for example, by direct application of an ointment, or active, for example, using a nasal spray or inhalant, in which case one component of the composition is an appropriate propellant.

Figure 5:
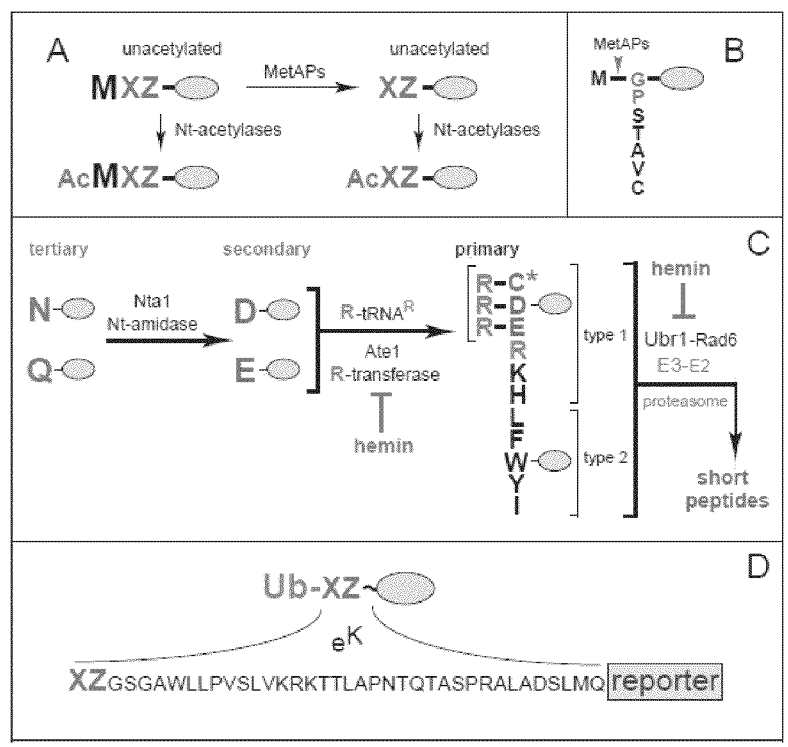
FIG. 5 illustrates the N$^α$-terminal acetylases, Met-aminopeptidases, and the Ubr1 branch of the N-end rule pathway. (A) N-terminal processing of nascent proteins by N$^α$-terminal acetylases (Nt-acetylases) and Met-aminopeptidases (MetAPs). "Ac" denotes the N$^α$-terminal acetyl moiety, M, Met, X and Z, single-letter abbreviations for any amino acid residue. Yellow ovals denote the rest of a protein. (B) MetAPs cleave off the N-terminal Met if a residue at position 2 belongs to the set of residues shown (SEQ ID NO:26). (C) The Ubr1-mediated branch of the *S. cerevisiae* N-end rule pathway (SEQ ID NO:27). See the main text for definitions of the "primary", "secondary" and "tertiary" destabilizing N-terminal residues. (D) A diagram of ubiquitin (Ub) fusions employed as reporters. X and Z, varied residues; e$^K$ is a previously described ~40-residue extension upstream of the ha-Ura3 reporter moiety (SEQ ID NO:28).

The N-end rule relates the in vivo half-life of a protein to the identity of its N-terminal residue. N-terminal degradation signals of the ubiquitin-dependent N-end rule pathway are called N-degrons. Their main determinant is a destabilizing N-terminal residue of a protein (FIG. 5C). Recognition components of the ubiquitin-dependent N-end rule pathway are called N-recognins. An N-recognin is an E3 Ub ligase that can target for polyubiquitylation at least a subset of N-degrons. The N-end rule of the yeast S. cerevisiae comprises 12 destabilizing, unacetylated N-terminal residues (out of the fundamental set of 20 amino acids). Among these residues, 8 are primary destabilizing residues: that is, recognized directly by the Ubr1 N-recognin, whereas the other 4 N-terminal residues, called secondary or tertiary destabilizing residues, must be modified through deamidation and/or arginylation before the corresponding proteins can be targeted by Ubr1 (FIG. 5C).

Figure 6:
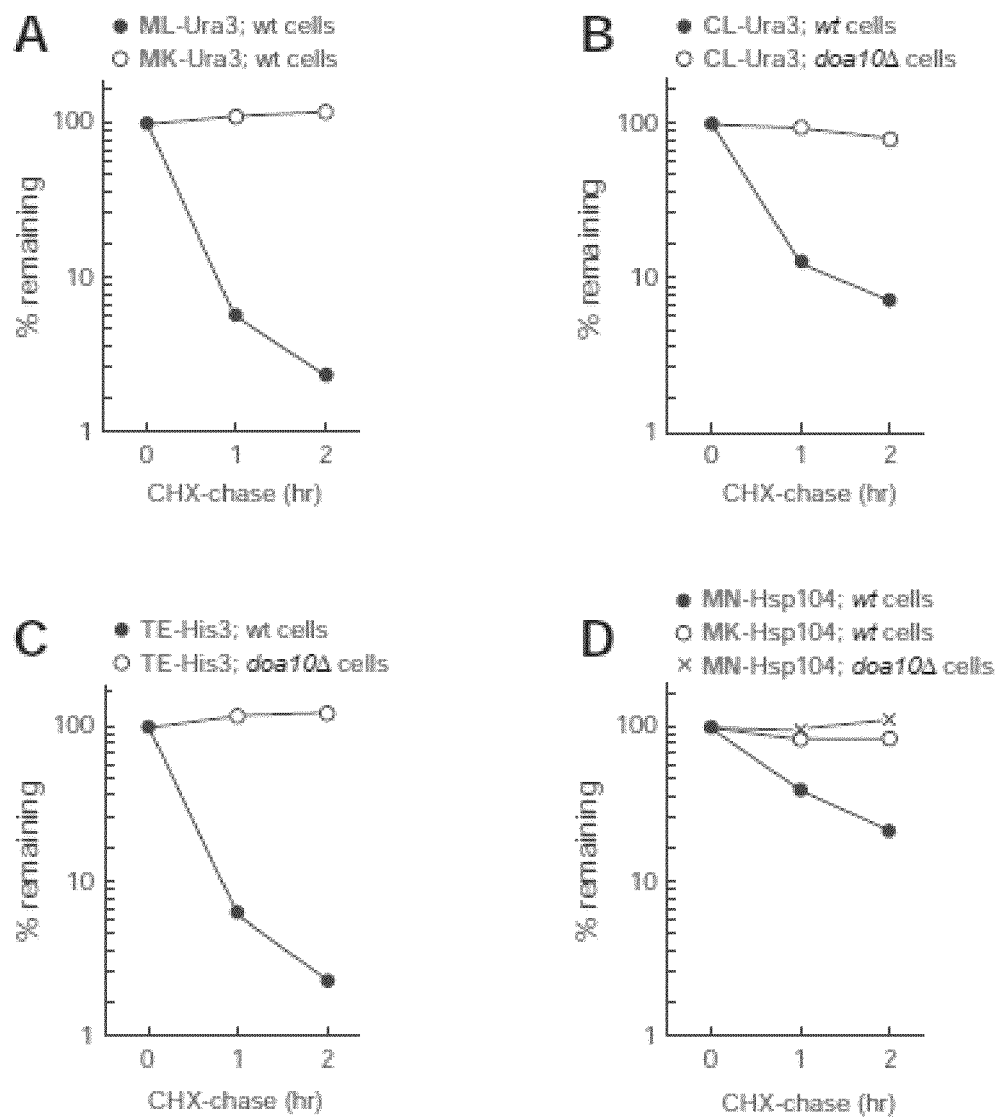
FIG. 6 illustrates the quantitation of cycloheximide-chase assays. Cycloheximide (CHX)-chase assays (FIG. 1, FIG. 3, FIG. 7, FIG. 8D-G, and FIG. 11) were carried out as described in Materials and Methods. Quantitations of the resulting immunoblots was performed using the ImageJ software (http://rsb.info.nih.gov/ij/index.html). For each time point, Image was employed to determine the ratio of a test protein's band intensity to that of tubulin loading control in the same lane. The resulting value at time zero was taken as 100%. (A) ML-Ura3 and MK-Ura3 in wild-type *S. cerevisiae* (see FIG. 1C for corresponding immunoblots). (B) CL-Ura3 in wild-type and doa10Δ *S. cerevisiae* (see FIG. 1E for corresponding immunoblots). (C) His3 (TE-His3, with the wild-type Thr-Glu N-terminal sequence) in wild-type and doa10Δ *S. cerevisiae* (see FIG. 3E for corresponding immunoblots). (D) Hsp104 (MN-Hsp104, with the wild-type Met-Asn N-terminal sequence, or MK-Hsp104, with the mutant Met-Lys N-terminal sequence) in wild-type and doa104 *S. cerevisiae* (see FIG. 3H for corresponding immunoblots).
Figure 7:
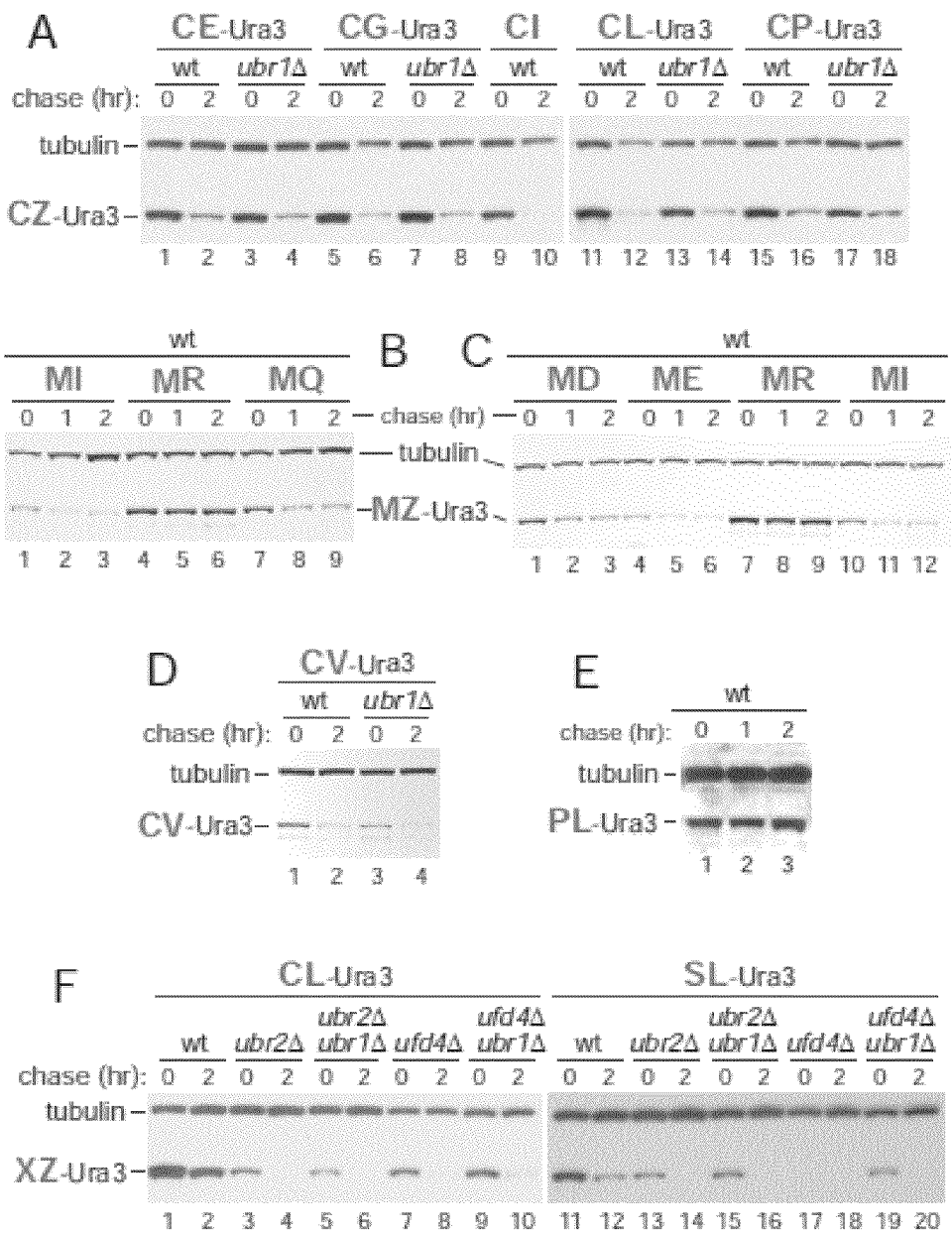
FIG. 7 illustrates the cycloheximide-chase assays with Ura3-based reporters. (A) Cycloheximide (CHX)-chases, for 0 and 2 hr, with CZ-e$^K$-Ura3 (CZ-Ura3) (Z=Glu, Gly, He, Leu, Pro), in wild-type versus ubr1Δ *S. cerevisiae*. CZ-Ura3 proteins were produced using the Ub fusion technique as described in FIG. 5D and Methods. Cell extracts were fractionated by SDS-PAGE, followed by immunoblotting with anti-ha antibody, and also with antibody to tubulin (loading controls). (B) As in A but CHX-chases for 0, 1 and 2 hr with MZ-Ura3 (Z=Ile, Arg, Gin) in wild-type S. cerevisiae. (C) As in B, with other MZ-Ura3 reporters (Z=Asp, Glu, Arg, He). (D) As in A, but with CV-Ura3. (E) As in C, but with PL-Ura3. (F) As in A, with CL-Ura3 (lanes 1-10) or SL-Ura3 (lanes 11-20), in wild-type versus ubr2Δ, ufd4, and double-mutant ubr24 ubr1Δ and ufd4Δ ubr1Δ cells, as indicated.

In mammalian cells, N-terminal Cys of N-end rule substrates can be oxidized, by nitric oxide (NO) and oxygen, and thereafter arginylated by an arginyl-transferase. The resulting N-terminal Arg is recognized by Ubr1-type N-recognins. In contrast, N-terminal Cys appeared to be a stabilizing residue in S. cerevisiae, which lacks NO synthases. That study also classified N-terminal Met, Ala, Val, Ser and Thr as stabilizing residues in S. cerevisiae. One caveat in these assignments is the possible influence of sequences downstream of the reporter's N-terminus. To determine whether N-terminal Cys can be destabilizing in yeast, we performed a screen in ura3 S. cerevisiae with Cys-Z-$e^K$-Ura3 reporters, produced by deubiquitylation of Ub-Cys-Z-$e^K$-Ura3. Z denotes a varied residue at position 2, and $e^K$ (extension (e) containing lysine (K)) denotes a ~40-residue sequence upstream of Ura3. The e extension (FIG. 5D) has a technically valuable property of lacking internal degrons while containing "ubiquitylatable" Lys residues. This screen identified Cys-Z-$e^K$-Ura3 fusions (Z=Leu, Val, Pro) with low Ura3 activity. We examined these fusions using a cycloheximide (CHX)-chase assay, in which a protein is analyzed by immunoblotting as a function of time after the inhibition of translation by CHX. The above three reporters were short-lived in vivo ($t_{1/2}$<1 hr), in contrast to GL-$e^K$-Ura3 (N-terminal Gly) and CK-$e^K$-Ura3 (Lys at position 2), which were long-lived (FIG. 1A, B, D, FIG. 6B, and FIG. 7A, D). Other non-basic residues at position 2 also yielded short-lived CZ-$e^K$-Ura3 (Z=Trp, Glu, Gly, Ile) (FIG. 1B and FIG. 7A).

Figure 8:
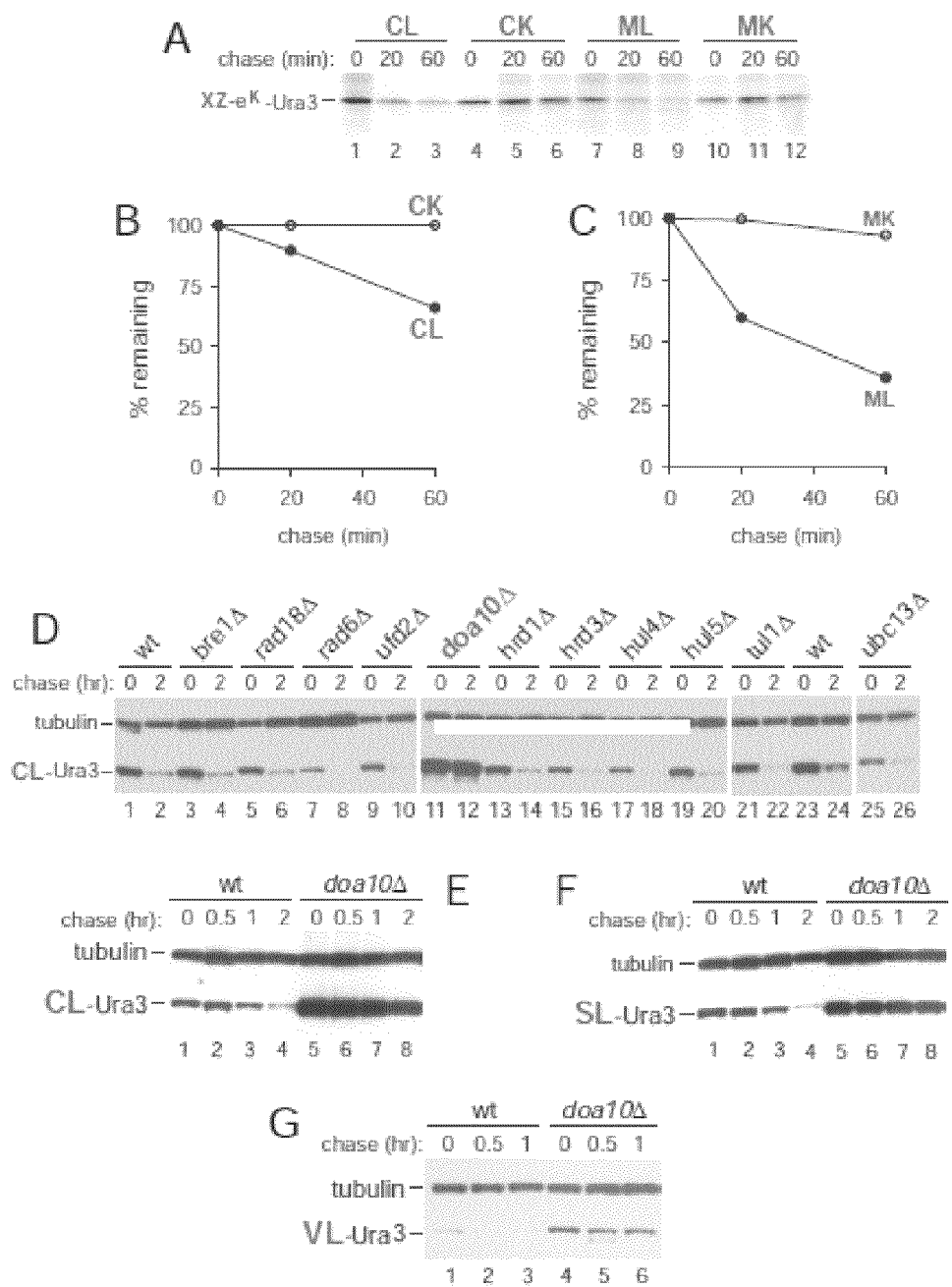
FIG. 8 illustrates the $^{35}$S-pulse-chase assays with XZ-Ura3 reporters and identification of Doa10 as the cognate Ub ligase. (A) $^{35}$S-pulse-chase assay with XZ-Ura3 (X=Cys, Met; Z=Leu, Lys). Wild-type S. cerevisiae expressing XZ-Ura3 test proteins (produced using the Ub fusion technique as described in FIG. 5D) were labeled for 5 min with [$^{35}$S] methionine/cysteine, followed by a chase for 20 and 60 min (see Methods). Lane 1-3, CL-Ura3. Lanes 4-6, CK-Ura3. Lanes 7-9, ML-Ura3. Lanes 10-12, MK-Ura3. (B) Quantitation of data in A, using PhosphorImager, for CL-Ura3 and CK-Ura3. (C) As in B, for ML-Ura3 and MK-Ura3. (D) CHX-chases for 0 and 2 hr with S. cerevisiae null mutants in the indicated E2 or E3 enzymes that expressed CL-Ura3. Note the virtually complete stabilization of CL-Ura3 in doa10Δ cells, but not in other tested mutants or wild-type cells. (E) CHX-chase for 0, 0.5, 1 and 2 hr with CL-Ura3 in wild-type (lanes 1-4) versus doa10Δ cells (lanes 5-8). (F) As in E but with SL-Ura3. (G) As in E but CIA-chase for 0, 0.5 and 1 hr with VL-Ura3 in wild-type (lanes 1-3) and doa10Δ cells (lanes 4-6).

Several other XL-$e^K$-Ura3 reporters (X=Met, Ser, Val, Ala, Thr) were also short-lived in vivo, like CL-$e^K$-Ura3 and in contrast to long-lived MK-$e^K$-Ura3 (Lys at position 2), MR-$e^K$-Ura3 (Arg at position 2), GL-$e^K$-Ura3 (N-terminal Gly) and PL-$e^K$-Ura3 (N-terminal Pro) (FIG. 1A-D, FIG. 6A, B, and FIG. 7B, C, E). We also performed $^{35}$S-pulse-chases with CL-$e^K$-Ura3 and ML-$e^K$-Ura3 versus CK-$e^K$-Ura3 and MK-e-Ura3 (FIG. 8A-C). The techniques of CHX-chases and S-pulse-chases are complementary, as the former method monitors degradation of all molecules of a specific protein, whereas the latter assay measures degradation of newly formed (pulse-labeled) molecules. $^{35}$S-pulse-chases confirmed the instability of XL-$e^K$-Ura3 (X=Cys, Met) and stability of XK-$e^K$-Ura3 (X=Cys, Met) (FIG. 1A, C, FIG. 6A, B, and FIG. 8A-C). The degradation of ML-e-Ura3 was proteasome-dependent, as the MG132 proteasome inhibitor significantly increased the level of the normally short-lived ML-$e^K$-Ura3 but not of the long-lived MK-$e^K$-Ura3, whose levels were high both in the presence and absence of MG132 (FIG. 1G).

To search for a Ub ligase or ligases that mediates the degradation of XL-$e^K$-Ura3 (X=Met, Ala, Val, Ser, Thr, Cys), we expressed CL-e-Ura3 in S. cerevisiae mutants that lacked specific E3 or E2 enzymes (FIG. 8D). Strikingly, CL-$e^K$-Ura3 became long-lived in the absence of Doa10 (FIG. 1E and FIG. 8D, E). Moreover, other short-lived XL-$e^K$-Ura3 proteins (Z=Met, Ser, Val) were also stable in doa10Δ cells (FIG. 1F and FIG. 8F, G). Doa10 is a transmembrane E3 Ub ligase that functions with the Ubc6/Ubc7 E2s and resides in the endoplasmic reticulum (ER) and inner nuclear membrane (INM). To address the above results, we focused on MATα2, a physiological substrate of Doa10.

Figure 9:
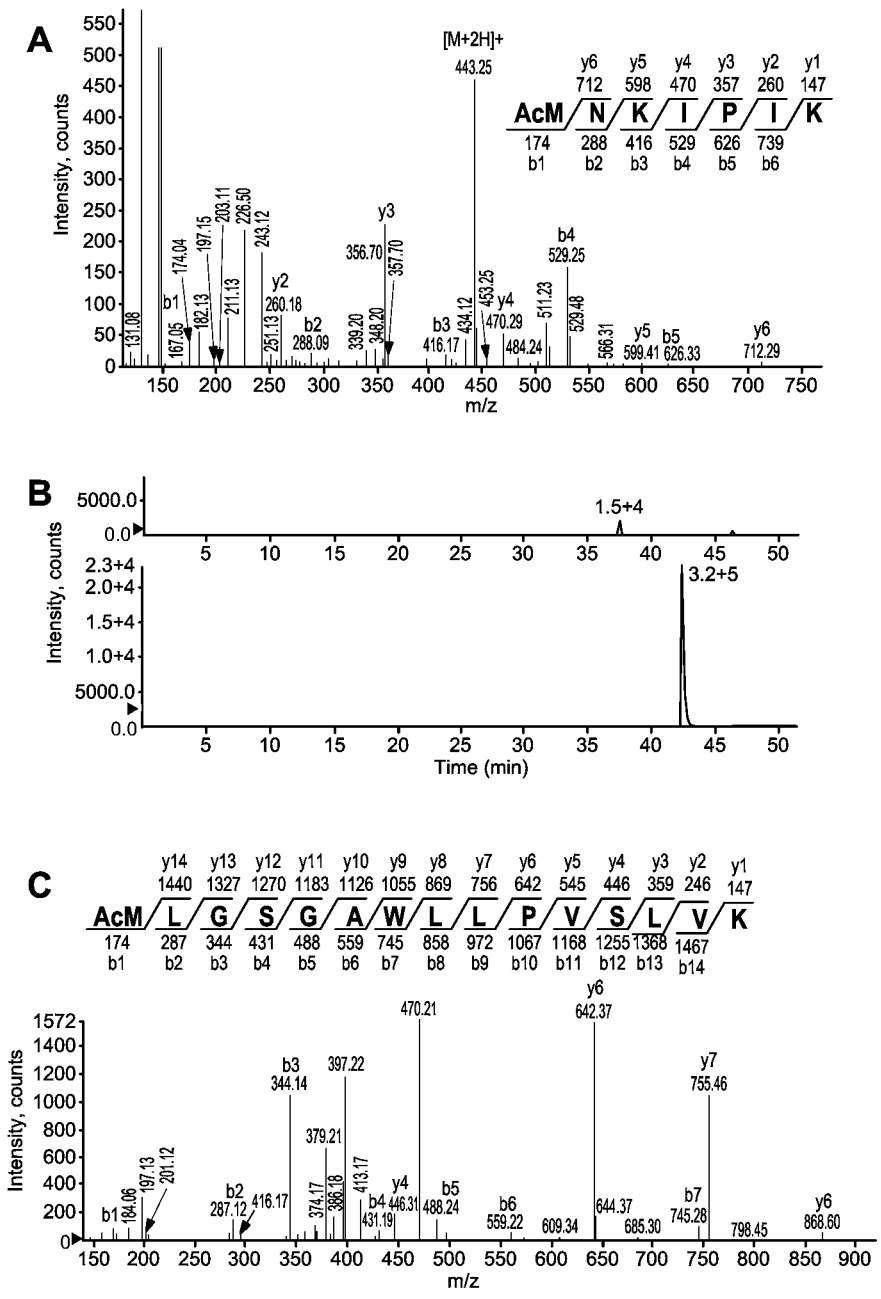
FIG. 9 illustrates the MATα2 repressor and the ML-Ura3 reporter are Nt-acetylated in vivo. (A) Full-length, C-terminally flag-tagged MATα2$_f$ was produced in doa104 ubc44 S. cerevisiae, purified, and subjected to SDS-PAGE. The band of MATα2$_f$ was excised, followed by in-gel digestion with the Asp-N protease and analysis by LC-MS/MS (see Methods). Shown here, using standard MS notations, are both the Nt-acetylated peptide of MATα2$_f$ (a doubly-charged peptide ion, at 443 m/z; molecular mass 886 Da; see the diagram) and the MS/MS-derived fragment ion spectrum of this peptide. The unacetylated counterpart of the Ac-MNKIPIK MATα2 (SEQ ID NO:4) peptide was not detected in two independent LC-MS/MS experiments. MATα2$_f$ is thus nearly completely Nt-acetylated in vivo. (B) ML-Ura3 was produced in doa10%1S. cerevisiae through the cotranslational deubiquitylation of Ub-ML-Ura3 (see FIG. 5D), purified, and subjected to SDS-PAGE. The band of ML-Ura3 was excised, followed by in-gel digestion with trypsin and analysis by LC-MS/MS (see Methods). The small (upper panel) and large (lower panel) peaks on selective ion chromatograms represent the doubly charged unacetylated MLGSGAWLLPVSLVK (SEQ ID NO:5) peptide (m/z 785.97, 2$^+$) for MLGSGAWLLPVSLVK (SEQ ID NO:5) (m/z 1571.96, 1$^+$) (upper panel), and the doubly charged acetylated Ac-MLGSGAWLLPVSLVK (SEQ ID NO:29) peptide (m/z 807.00, 2$^+$) for Ac-MLGSGAWLL-PVSLVK (SEQ ID NO:29) (m/z 1613.96, 1*) (lower panel). According to the ratio of two species (the relative ion peak areas), more than 90% of ML-Ura3 was N-acetylated in vivo. (C) ML-Ura3, produced and analyzed by LC-MS/MS as described in B. Shown here is MS/MS-produced fragment ions spectrum of the doubly charged Nt-acetylated Ac-MLGSGAWLLPVSLVK (SEQ ID NO:29) peptide (m/z 806.99, 2+) sequenced through the identification of specific fragmentation ions (bi=174.06, b$_2$=287.14, 1)$_3$=344.16, b$_4$=431.20, b$_5$=488.22, b$_6$=559.26, b$_7$=745.33, y$_2$=246.18, y$_3$=359.27, y$_4$=446.30, y$_6$=642.42, y$_7$=755.50, y$_8$=868.50).
Figure 10:
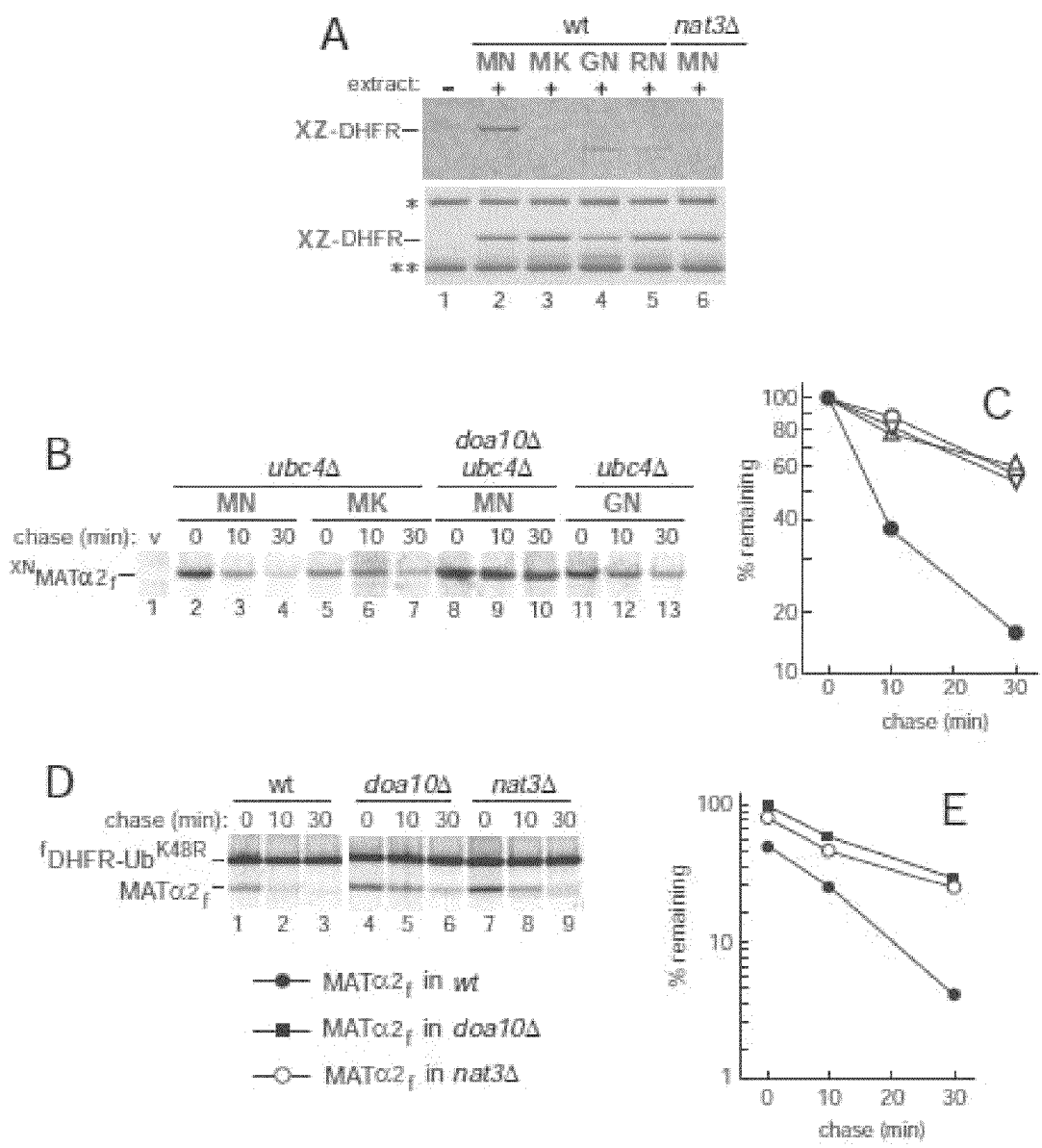
FIG. 10 illustrates the $^{Ac}$N-degron of the MATα2 repressor. (A) Upper panel: lane 1, Ub-MN-α2$^{3-67}$-e$^K$-DHFR$_{ha}$ was expressed in E. coli, purified, and deubiquitylated using a purified deubiquitylating enzyme. The resulting MN-α2$^{3-67}$-e-DHFRha derived from the N-terminal Deg1 region of MATα2 (see the main text), was bound to agarose beads containing anti-ha antibody. Immobilized MN-α2$^{3-67}$-e$^K$-DHFRh$_a$ was incubated with buffer alone (negative control) in the presence of $^{14}$C-labeled acetyl-CoA, followed by treatment of the beads with elution buffer, SDS-PAGE and autoradiography. Lane 2, same as lane 1 but incubation with extract from wild-type S. cerevisiae. Lanes 3-5, same as lane 2 but with MK-α2$^{3-67}$-e$^K$-DHFR$_{ha}$, GN-α2$^{3-67}$-e$^K$-DHFR$_{ha}$ and RN-α2$^{3-67}$-e$^K$-DHFR$_{ha}$, respectively. Note the absence of Nt-acetylation of these reporters, in contrast to MN-α2$^{3-67}$-e$^K$-DHFR$_{ha}$ (lane 2). Lane 6, same as lane 2 but with extract from nat3.61 cells, which lacked the cognate NatB Nt-acetylase. The lower panel shows a Coomassie-stained gel that yielded autoradiographic data in the upper panel. The bands of XZ-α2$^{3-67}$-e$^K$-DHFR$_{ha}$ (XZ-DHFR) reporters are indicated. Single and double asterisks denote an admixture of the light and heavy IgG chains, respectively, that partially leaked from agarose beads during the elution of reporters. (B) $^{35}$S-pulse-chase assay with full-length, C-terminally flag-tagged MATα2$_f$. Lane 1, vector alone. Lanes 2-4, ubc4Δ S. cerevisiae expressing wild-type MATα2$_f$ were labeled for 5 min at 30° C. with [$^{35}$S]methionine/cysteine, followed by a chase for 10 and 30 min. Cell extracts were precipitated with anti-flag antibody, followed by SDS-PAGE and autoradiography. Lanes 5-7, same as lanes 2-4 but with $^{MK}$MATα2$_f$, containing Lys (instead of Asn) at position 2. Lanes 8-10, same as lanes 2-4 but in ubc4Δ doa10Δ cells. Lanes 11-13, same as lanes 1-4 but with MATα2$_f$ (expressed as MATα2$_f$), containing N-terminal Gly. (C) Quantitation of the data in B, using PhosphorImager. Solid and open circles, upright and inverted triangles: $^{MN}$MATα2$_f$, $^{MK}$(MATα2$_f$, $^{GN}$MATα2$_f$ in ubc4Δ cells, and $^{MK}$MATα2$_f$ in ubc4Δ doa10Δ cells, respectively (this is the same panel as FIG. 2F). (D) $^{35}$S-pulse-chase assay with full-length, C-terminally flag-tagged MATα2$_f$ that differed from the assay in B, C by the utilization of a "built-in" reference protein. Specifically, wild-type MATα2$_f$ was expressed as a Ub fusion, $^f$DHFR-Ub$^{K48R}$-MATα2$_f$. The cotranslational cleavage of this fusion at the Ub$^{K48R}$-MATα2$_f$ junction produced the long-lived (DHFR-Ub$^{K48R}$ reference protein and the MATα2$_f$ test protein. The bands of MATα2$_f$ and $^f$DHFR-Ub$^{K48R}$ (the reference protein) are indicated on the left. Lanes 1-3, wild-type cells. Lanes 4-6, doa10Δ cells. Lanes 7-9, nat3Δ cells (lacking the cognate NatB Nt-acetylase). (E) Quantitation of data in D, using PhosphorImager. Solid circles, solid squares, and open circles, MATα2$_f$ in wild-type cells, in doa10Δ cells, and in nat3Δ cells, respectively. In the Ub-reference technique, the presence of a "built-in" reference protein (DHFR-Ub) makes it possible to detect and measure the initial degradation of pulse-labeled MATα2$_f$ (i.e., its decay during the pulse). The degradation of MATα2$_f$ involved the targeting of $^{Ac}$N-degron, as a significant part of this degradation was found to require the presence of the Doa10 Ub ligase, and of the Nat3-containing NatB Nt-acetylase as well. Specifically, the level of MATα2$_f$ at 0 min (the end of pulse) in wild-type cells was 55% of the O-min level of MATα2$_f$ in doa10Δ cells (the latter level was taken as 100%). The O-min level of MATα2$_f$ in nat34 cells was 83%, i.e., MATα2$_f$ was significantly stabilized in nat34 cells as well, though not as strongly as in doa10Δ cells. The reason for a significant residual degradation of the full-length MATα2$_f$ protein in doa10Δ cells is that MATα2$_f$ contains not only the Doa10-dependent $^{Ac}$N-degron but at least two other, Doa10-independent degrons as well (see the main text).

The 24 kDa MATα2 contains more than one degradation signal and has an in vivo half-life of 5-10 min. MATα2 represses transcription of a-specific genes in a-cells, whereas in a/α diploids the MATα2-MATα1 complex represses haploid-specific genes. The 67-residue N-terminal region of MATα2, termed Deg1, has been shown to harbor a Doa10-dependent degron. MATα2 is absent from databases of Nt-acetylated proteins, possibly because of its short in vivo half-life. We expressed full-length MATα2 in doa10Δ ubc4Δ yeast and analyzed purified MAT<α2 using mass spectrometry (LC-MS/MS). The results (FIG. 9A) indicated virtually complete Nt-acetylation of MATα2 (no MATα2 that lacked Nt-acetylation could be detected), in agreement with Nt-acetylation of other proteins containing the N-terminal Met-Asn. Similar LC-MS/MS of the Doa10-targeted, purified ML-$e^K$-Ura3 (FIG. 9B, C) indicated the Nt-acetylation of this reporter, in agreement with Nt-acetylation of other proteins containing the N-terminal Met-Leu. We also observed Nt-acetylation of a Deg1-bearing reporter that was purified from E. coli and incubated with S. cerevisiae extracts (FIG. 10A).

Figure 2:
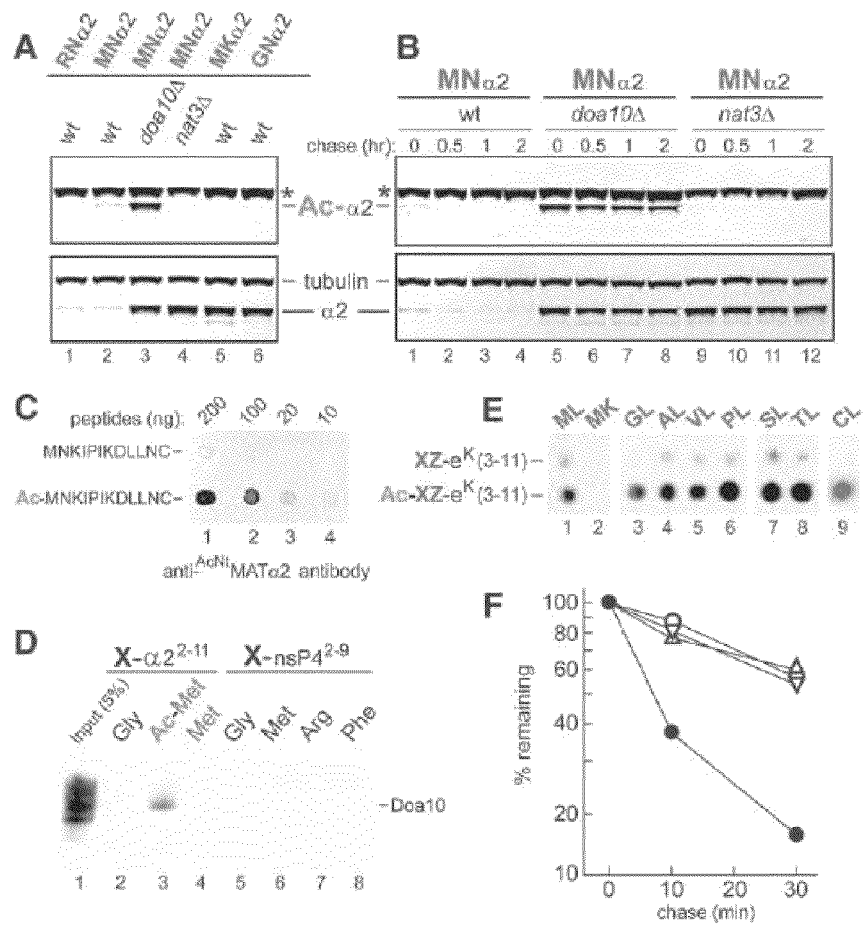
FIG. 2 illustrates Doa10 as an N-recognin. (A) Extracts from wild-type, doa10Δ and nat3Δ *S. cerevisiae* that expressed XZ-a2$^{3n67}$-e$^K$-Ura3 (XZa2) (X=Met, Arg, Gly; Z=Asn, Lys) were immunoblotted with anti-$^{AcNt}$MATα2 (which selectively recognized Nt-acetylated MNα2) or (separately) with anti-ha antibody, which recognized both Nt-acetylated and unacetylated MNα2, or with anti-tubulin antibody. XZa2 ("a2"), Nt-acetylated XZa2 ("Ac-a2"), and tubulin are indicated. Asterisks denote a protein crossreacting with anti-$^{AcNt}$ MATα2. (B) As in A but CHX-chases for 0, 0.5, 1 and 2 hr with MNα2, in wild-type, doa10Δ and nat3Δ cells. (C) Indicated amounts of the Nt-acetylated Ac-MNKIP-IKDLLNC (SEQ ID NO:1) peptide versus its unacetylated counterpart (SEQ ID NO:10) were spotted onto membrane and assayed for their binding to anti-$^{AcNt}$ MATα2 antibody. (D) X-peptide pulldown with peptides XNKIPIKDLLNC (SEQ ID NO:2) (X=Met, $^{Ac}$Met, Gly) (lanes 2-4) or XIFST-DTGPGGC (SEQ ID NO:3) (X=Gly, Met, Arg, Phe) (lanes 5-8) and extract of *S. cerevisiae* that expressed Doa10$_{myc13}$. Lane 1, input extract (5%). (E) SPOT assay with purified, flag-tagged Doa10 and spot-arrayed synthetic peptides XZ-e$^{K(3-11)}$ (X=Gly, Ala, Val, Pro, Ser, Thr, Cys; Z=Leu, Lys) and their Nt-acetylated XZ-e$^{K(3-11)}$ counterparts. XZ residues are indicated at the top of membrane. (F) Quantitation, using PhosphorImager, of $^{35}$S-pulse-chases with MATα2$_f$ and its mutant derivatives (FIG. 10B, C). Solid and open circles, upright and inverted triangles: $^{MN}$MATα2$_f$, $^{MK}$MATα2$_f$, $^{GN}$MATα2$_f$ (initially $^{MGN}$MATα2$_f$) in ubc4Δ cells, and $^{MN}$MATα2$_f$ in ubc4Δ doa10Δ cells, respectively.

In addition, we produced an antibody, termed anti-$^{AcNt}$MAT<α2, that recognized the Nt-acetylated N-terminal sequence of MATα2 (FIG. 2C) and was specific for the Nt-acetylated, hemagluttin (HA)-tagged, MATα2-derived MN-α2$^{3-6,7}$-$e^K$-Ura3 reporter, denoted as MNα2 (FIGS. 2A and B). $^{AcNt}$MATα2 and anti-Ha (the latter antibody recognized both Nt-acetylated and unacetylated MNα2) were used to immunoblot extracts of cells that expressed MN<α2. Wild-type cells contained barely detectable steady-state levels of either total or Nt-acetylated MNα2 (FIG. 2A), owing to its rapid degradation. By contrast, nat3Δ cells, which lacked the cognate NatB Nt-acetylase, contained high levels of unacetylated MNα2 (detected by anti-Ha) and almost no Nt-acetylated MNα2 (FIG. 2A). Similar patterns were observed in wild-type cells that expressed MKα2 (Lys at position 2) or GNα2 (N-terminal Gly) (FIG. 2A). As shown by proteome-scale analyses, S. cerevisiae proteins containing Lys at position 2 are virtually never Nt-acetylated, and few proteins that bear N-terminal Gly are Nt-acetylated. Most significantly, high levels of Nt-acetylated MNα2 were present in doa10Δ cells (FIG. 2A), owing to metabolic stabilization of Nt-acetylated MNα2 in the absence of Doa10. These data (FIG. 2A) were in agreement with the LC-MS/MS results that MATα2 was Nt-acetylated (FIG. 9A).

To determine whether the Doa10 Ub ligase recognizes the Nt-acetylated Met ($^{AcNt}$Met), we employed the X-peptide assay with synthetic peptides XNKIPIKDLLNC (SEQ ID NO:2) (X=Met, $^{Ac}$Met, Gly). Except for C-terminal Cys and the varied N-terminal residues, these peptides were identical to the N-terminal region of MATα2. Immobilized peptides were incubated with extract from yeast that expressed mycn-tagged Doa10, followed by elution of the bound proteins and immunoblotting with anti-myc antibody. Doa10$_{myc13}$ bound to the MATα2 peptide with N-terminal $^{AcNt}$Met but not to the otherwise identical peptides with unmodified N-terminal Met or with N-terminal Gly (FIG. 2D). Additional controls, which did not bind to Doa10$_{men}$, were peptides XIFSTDTGPGGC (SEQ ID NO:3) (X=Gly, Met, Arg, Phe) derived from the N-terminus of nsP4, a Sindbis viral protein (FIG. 2D). Thus Doa10 recognizes the $^{AcNt}$Met residue and does not have a significant affinity for downstream sequences of MATα2 or nsP4.

Doa10 specificity was also analyzed with the synthetic peptide arrays on membrane support (SPOT) technique, in which synthetic XZ-e$^{K(3-11)}$ peptides and their Nt-acetylated $^{Ac}$XZ-e$^{K(3-11)}$ counterparts were C-terminally linked to a membrane as "dots" in equal molar amounts. SPOT peptides were identical to the N-terminal region of e$^K$ (FIG. 5D), with varied residues at positions 1 and 2. A SPOT assay with C-terminally flag-tagged Doa10$_f$ indicated the recognition of $^{AcNt}$Met by Doa10, in agreement with the results of the X-peptide assay (FIG. 2D, E). SPOT also indicated a highly preferential binding of Doa10$_f$ to other Nt-acetylated (versus unacetylated) $^{Ac}$XZ-e$^{K(3-11)}$ peptides (X=Gly, Ala, Val, Pro, Ser, Thr, Cys), including Nt-acetylated Gly and Pro (FIG. 2E). Thus, Gly and Pro are (largely) stabilizing in the N-end rule (FIG. 1D and FIG. 7E) because N-terminal Gly and Pro are Nt-acetylated in relatively few proteins. Interestingly, Doa10 did not bind to N-terminal $^{AcNt}$Met if it was followed by Lys at position 2 (FIG. 2E). Thus, the metabolic stability of XK-e-Ura3 (X=Met, Cys) containing Lys at position 2 (e.g., FIG. 1A, C) stems not only from the absence of Nt-acetylation but also from the rejection, by Doa10, of Lys at position 2 (FIG. 2E).

Taking advantage of the specificity of anti-$^{AcNt}$MATα2 for Nt-acetylated MNα2, we performed CHX-chases as well, in addition to steady-state assays (FIG. 2A, B). MNα2 was short-lived in wild-type cells. Even "time-zero" samples, at the time of addition of CHX, contained barely detectable levels of either Nt-acetylated or total MNα2 (FIG. 2B). By contrast, MNα2 was a long-lived protein in doa10Δ and nat3Δ cells, but for different reasons: in doa10Δ cells, which lacked the cognate Ub ligase, MNα2 was long-lived despite its Nt-acetylation, whereas in nat3Δ cells, which lacked the cognate Nt-acetylase, the largely unacetylated MNα2 was long-lived because the targeting by Doa10 required Nt-acetylation (FIG. 2B).

MATα2 contains yet another degradation signal, targeted by an unknown E3 in conjunction with the Ubc4 and (to a minor extent) Ubc5 E2s. This degron is nearly inactive in ubc4Δ cells. By contrast, the Doa10 Ub ligase functions with the Ubc6/Ubc7 E2s and remains active in ubc4Δ cells. In $^{35}$S-pulse-chases with C-terminally flag-tagged full-length MATα2$_f$, the rapid degradation of wild-type $^{MN}$MATα2$_f$ in ubc40 cells ($t_{1/2}$~9 min) was substantially decreased in doa10Δ ubc4Δ cells ($t_{1/2}$~35 min) (FIG. 2F and FIG. 10B, C). A Lys residue at position 2 in a polypeptide chain is known to preclude Nt-acetylation in S. cerevisiae, and few proteins that bear N-terminal Gly are Nt-acetylated. The absence of Nt-acetylation in $^{MK}$MATα2$_f$ (Lys at position 2) or $^{GN}$MATα2$_f$ (Gly at position 1) decreased the rate of MATα2 degradation in wild-type cells (FIG. 2F and FIG. 10B, C). The extent of this decrease, in comparison to degradation of Nt-acetylated $^{MN}$MATα2$_f$ in wild-type cells, was indistinguishable from the decrease of $^{MN}$MATα2$_f$ degradation in doa10Δ cells, which lacked the Doa10 Ub ligase (FIG. 2F and FIG. 10B-E). In addition to indicating that the sole degron targeted by Doa10 in MATα2 is its $^{Ac}$N-degron, these results were also in agreement with technically independent evidence that utilized the anti-$^{AcNt}$MAT<α2 to prove that the Nt-acetylation of MNα2 was required for its targeting by Doa10 (FIG. 2A-C).

Figure 3:
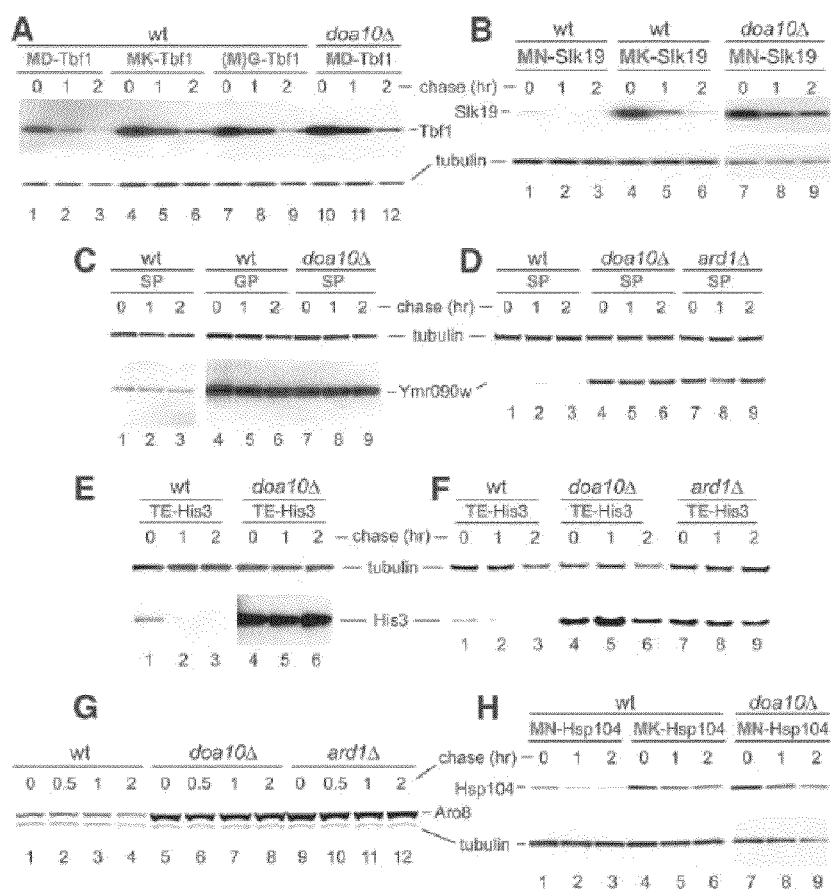
FIG. 3 illustrates the $^{Ac}$N-degrons in yeast proteins. (A) Lanes 1-3, CHX-chase for 0, 1 and 2 hr, in wild-type *S. cerevisiae* expressing TbfUa. Lanes 4-6, 7-9, 10-12: analogous patterns but in doa10Δ cells with $^{Mlc}$Tbf1$_{ha}$ (Lys at position 2), $^{G}$Tbf1$_{ha}$ (initially $^{MG}$Tbf1$_{ha}$), and wild-type Tbf1h$_a$. (B) As in A, but with wild-type Slk19ha and its mutant derivatives, in wild-type versus doa10Δ cells. (C) As in A, but with wild-type Ymr090wh$_a$ and its mutant derivatives, in wild-type versus doa10Δ cells. (D) As in C, but with wild-type Ymr090wh$_a$ in wild-type versus doa10Δ and ard1Δ cells. (E) As in A, but with wild-type His3h$_a$ in wild-type versus doa10Δ cells. (F) As in E, with wild-type His3h$_a$ in wild-type versus doa10Δ and ard1Δ cells. (G) As in A, but CHX-chases for 0, 0.5, 1 and 2 hr with wild-type Aro8h$_a$, in wild-type versus doa10Δ and ard1Δ cells. (H) As in A, but with wild-type Hsp104h$_a$ and its mutant derivatives in wild-type versus doa10Δ cells.
Figure 11:
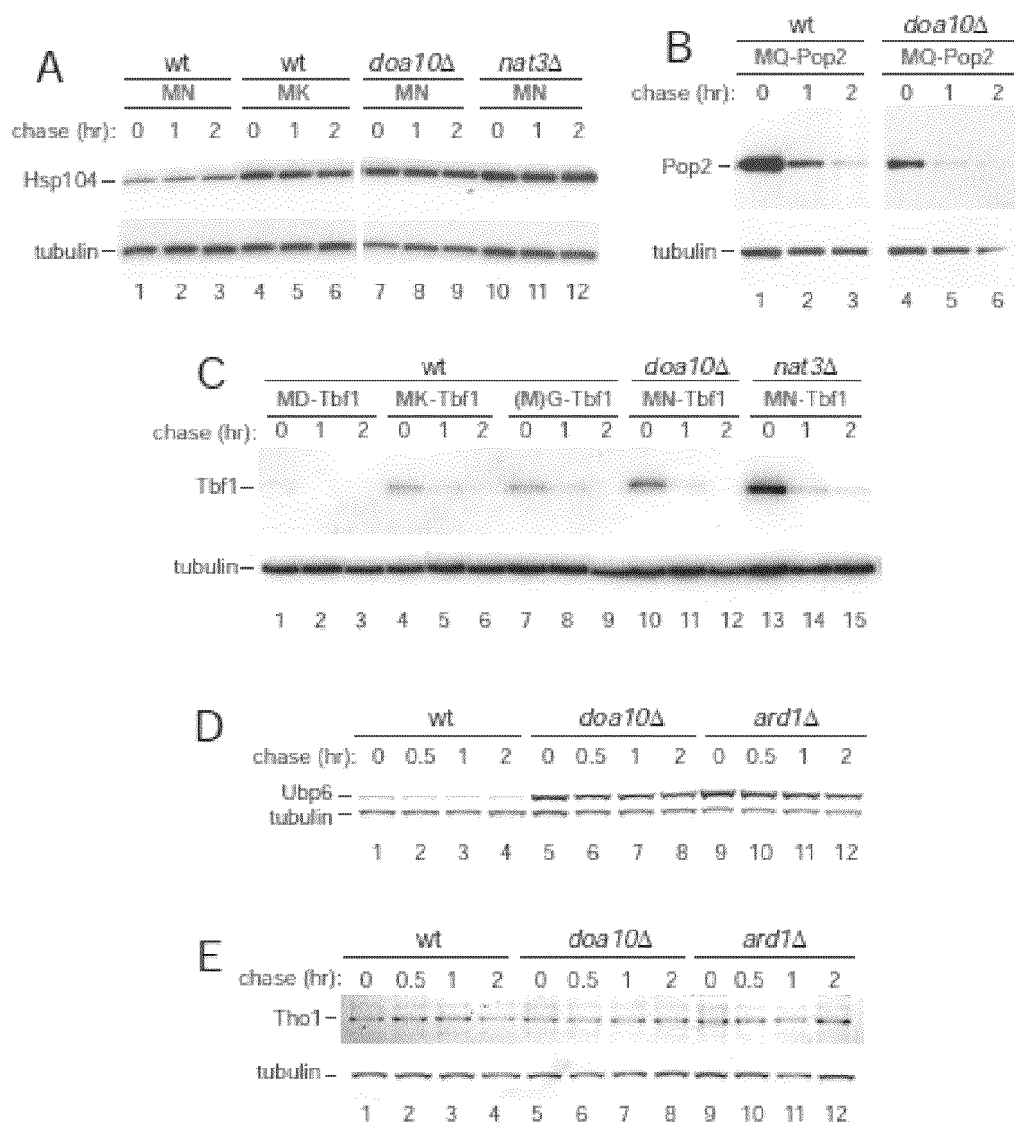
FIG. 11 illustrates the $^{Ac}$N-degrons in S. cerevisiae proteins. (A) Lanes 1-3, CHX-chase, for 0, 1 and 2 hr, in wild-type cells expressing C-terminally ha-tagged Hsp104ha (N-terminal Met-Asn). Lanes 4-6, same as lanes 1-3 but with Hsp104t$_{ha}$, containing Lys (instead of Asn) at position 2. Lanes 7-9, same as lanes 1-3 but in doa10Δ cells. Lanes 10-12, same as lanes 1-3 but in nat3Δ cells, lacking the cognate NatB Nt-acetylase. (B) Lanes 1-3, CHX-chase, for 0, 1 and 2 hr, in wild-type cells expressing C-terminally ha-tagged Pop2$_{ha}$ (N-terminal Met-Gin). Lanes 4-6, same as lanes 1-3 but in doa10Δ cells. Note that Pop2$_{ha}$ remains short-lived in the absence of Doa10. (C) CHX-assays, for 0, 1 and 2 hr, with Tbf1ha (N-terminal Met-Asp), a set of experiments independent from that in FIG. 3A. Lanes 1-3, Tbf1$_{ha}$ in wild-type cells. At this level of sensitivity, to avoid overexposures of other lanes, the band of short-lived Tbf1ha is nearly undetectable even at time 0. Lanes 4-6, same as lanes 1-3 but with $^{MK}$Tbf1$_{ha}$, containing Lys (instead of Asp) at position 2. Lanes 7-9, same as lanes 1-3 but with $^{MG}$Tbf1$_{ha}$ ($^{MG}$Tbf1$_{ha}$), containing N-terminal Gly. Lanes 10-12, same as lanes 1-3 but in doa10Δ cells. Lanes 13-15, same as lanes 1-3 but in nat34 cells. (D) As in C, but CHX-assay for 0, 0.5, 1 and 2 hr with Ubp6$_{ha}$ (N-terminal Ser-Gly) in wild-type versus doa10Δ and ard1Δ cells, the latter lacking the cognate NatA Nt-acetylase. (E) As in D, but with Tho1$_{ha}$ (N-terminal Ala-Asp) in wild-type versus doa10Δ and ard1Δ cells. Note the metabolic stability of Tho1 and its essentially equal levels in different genetic backgrounds.

As expected, given the presence of $^{Ac}$N-degron in MATα2, both full-length MATα2$_f$ and MNα2 were strongly stabilized in nat3Δ cells, which lacked the cognate NatB Nt-acetylase (FIG. 2A, B and FIG. 10D, E). Besides MATα2, our survey of S. cerevisiae proteins has encompassed, thus far, Tbf1, a regulator of telomeres; Slk19, a regulator of chromosome segregation; Ymr090w, a cytosolic protein of unknown function; His 3, an enzyme of histidine biosynthesis; Pop2, a subunit of mRNA-deadenylating complexes; Hsp104, a chaperone; Tho1, an RNA-binding regulator; Ubp6, a deubiquitylating enzyme; and Aro8, an aromatic aminotransferase (FIG. 3, FIG. 6C, D, and FIG. 11).

Figure 12:
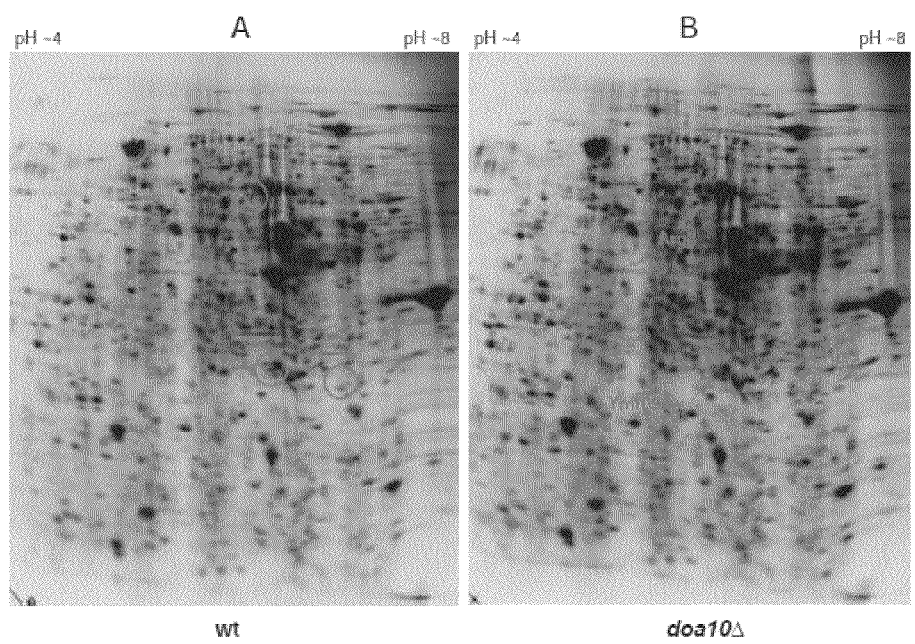
FIG. 12 illustrates the $^{35}$S-pulse-chase of S. cerevisiae proteins fractionated by 2-D electrophoresis. (A) Wild-type S. cerevisiae were pulse-labeled for 15 min at 30° C. with $^{35}$S-methionine/cysteine, followed by extraction of proteins, 2-D electrophoresis and autoradiography (see Methods). (B) Same as in A but in a doa10Δ cells. As described in the main text, these and related $^{35}$S-pulse-chase patterns (panels A, B, and data not shown) contained a number of protein spots with significantly higher relative levels of $^{35}$S in samples from doa10Δ versus wild-type cells. Three of these spots (this survey continues to expand) were examined using standard MALDI-MS fingerprinting techniques, thereby identifying His3 Aro8 and Ymr090w (see Methods and the main text) as putative substrates of the Doa10 Ub ligase. The spots of His3, Aro8 and Ymr090w are indicated by red arrows in B. Red circles in A demarcate the regions containing these S-labeled proteins in extract from wild-type S. cerevisiae, at lower levels than in doa10Δ cells (panel A and data not shown).

Wild-type Tbf1, Slk19, Pop2, Hsp104, Tho1, Ubp6 and Aro8 are known to be Nt-acetylated. In contrast, the testing of His3 and Ymr090w stemmed from our 2-D electrophoretic analyses, including $^{35}$S-pulse-chases. The resulting patterns contained a number of protein spots with significantly higher levels of $^{35}$S in samples from doa10Δ versus wild-type cells (FIG. 12). We examined three of these spots using matrix-assisted laser desorption/ionization-MS (MALDI-MS) fingerprinting techniques and identified His3, Ymr090w, and Aro8 as putative substrates of Doa10 (FIG. 12). The testing for $^{Ac}$N-degrons in Tbf1, Slk19, Ymr090w, His3, Pop2, Hsp104, Tho1, Ubp6 and Aro8 (this analysis included second-residue mutants of some of these proteins) involved CHX-chases in the presence versus absence of a cognate Nt-acetylase or the Doa10 Ub ligase. As shown in FIG. 3, FIG. 6C, D and FIG. 11, we identified $^{Ac}$N-degrons in all of these proteins (in addition to MATα2), except Pop2 and Tho1.

Figure 4:
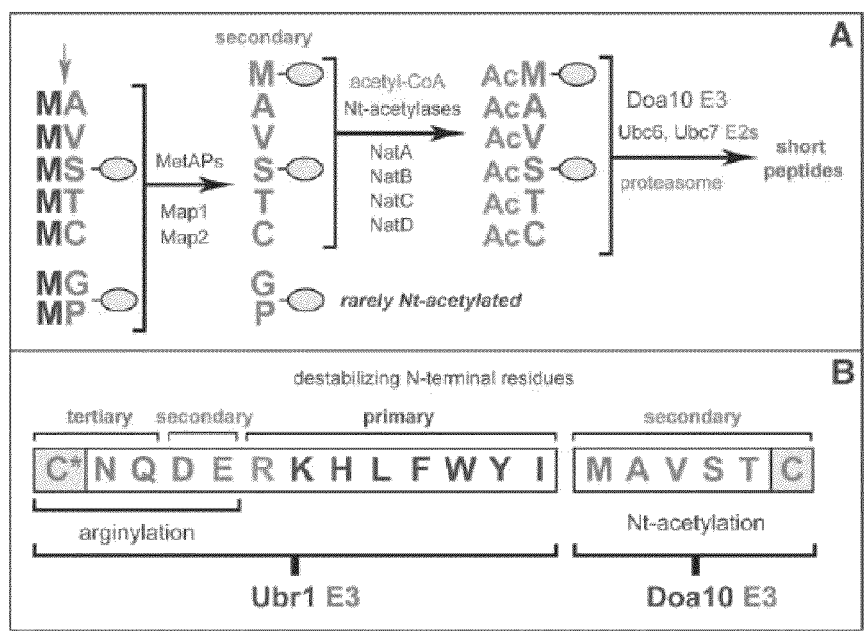
FIG. 4 illustrates the N$^α$-terminal acetylases, Met-aminopeptidases, and the Doa10 branch of the N-end rule pathway. (A) The Doa10-mediated branch of the *S. cerevisiae* N-end rule pathway (see FIG. 5C for the Ubr1-mediated branch of this pathway). Red arrow on the left indicates the MetAP-mediated removal of N-terminal Met. This Met is retained if a residue at position 2 is nonpermissive (too large) for MetAPs. If the retained N-terminal Met or N-terminal Ala, Val, Ser, Thr and Cys are followed by "acetylation-permissive" residues, the above N-terminal residues are usually Nt-acetylated. The resulting N-degrons are termed $^{Ac}$N-degrons. The term "secondary" refers to the necessity of modification (Nt-acetylation) of a destabilizing N-terminal residue before a protein can be recognized by a cognate Ub ligase (see also FIG. 5C). Proteins containing $^{Ac}$N-degrons are targeted for ubiquitylation (and proteasome-mediated degradation) by the Doa10 E3 Ub ligase. Although Gly or Pro can be made N-terminal by MetAPs, and although Doa10 can recognize Nt-acetylated Gly and Pro (FIG. 2E), few proteins with N-terminal Gly or Pro are Nt-acetylated. (B) The Ubr1Δnd Doa10 branches of the N-end rule pathway. Both branches target, through different mechanisms, the N-terminal Cys residue (yellow rectangles), with oxidized Cys marked by asterisk (SEQ ID NO'S 24 and 25, respectively).

The results, summarized in FIG. 4, revealed the function of Nt-acetylation, producing the largest increase in the scope of the ubiquitin-dependent N-end rule pathway since its discovery more than two decades ago. At present, only ~10 proteins in all eukaryotes have been identified that require, or are inferred to require, Nt-acetylation for their in vivo roles, which are unrelated to protein degradation. In contrast, the creation of degradation signals by Nt-acetylation (FIG. 4) is relevant, in principle, to all Nt-acetylated proteins. N-terminal Met, Ala, Val, Ser, Thr, and Cys are shown here to function as secondary destabilizing residues in the ubiquitin-dependent N-end rule pathway, in that they must be Nt-acetylated before their recognition by the S. cerevisiae Doa10 Ub ligase as N-degrons, termed $^{Ac}$N-degrons, that require Nt-acetylation (FIG. 4). Out of 20 amino acids in the genetic code, 18 are now known to function as destabilizing N-terminal residues in the ubiquitin-dependent N-end rule pathway (FIG. 4 and Figure SIC). More than 50% of proteins in S. cerevisiae and more than 80% of proteins in human cells are Nt-acetylated. Thus, remarkably, the majority of eukaryotic proteins harbor a specific degradation signal from the moment of their birth. Putative metazoan counterparts of the yeast Doa10 Ub ligase include human TEB4, indicating the likely relevance of our results to all eukaryotes.

The Nt-acetylation is largely cotranslational, apparently irreversible, and involves a majority of cellular proteins. Not wishing to be bound by theory, we suggest that a major role of these degradation signals involves quality control mechanisms and regulation of protein stoichiometrics in a cell. A key feature of such mechanisms would be conditionality of $^{Ac}$N-degrons. If a nascent Nt-acetylated protein can fold its N-terminal domain rapidly enough, or if this protein either interacts with a "protective" chaperone such as Hsp90 or becomes assembled into a cognate multisubunit complex, the cotranslationally created $^{Ac}$N-degron of this protein may become inaccessible to the Doa10 Ub ligase. Consequently, the degradation of this protein would be decreased or precluded. In contrast, delayed or defective folding of a protein's N-terminal domain (because of oxidative, heat or other stresses, or a conformation-perturbing mutation, or non-stoichiometric levels of cognate protein ligands) would keep an $^{Ac}$N-degron exposed (active) and thereby increase the probability of the protein's destruction.

The discovery that Nt-acetylation is a part of the ubiquitin-dependent N-end rule pathway (FIG. 4) has also revealed the physiological functions of Nt-acetylases and Met-aminopeptidases. Nt-acetylases produce $^{Ac}$N-degrons, while the upstream Met-aminopeptidases make possible these degradation signals, all of them except the one mediated by Nt-acetylated Met (FIG. 4). Nt-acetylases and Met-aminopeptidases are universally present, extensively characterized and essential enzymes whose physiological roles were largely unknown. These enzymes are now functionally understood components of the ubiquitin-dependent N-end rule pathway (FIG. 4 and FIG. 5C).

Although the bulk of Nt-acetylation is cotranslational, posttranslational Nt-acetylation is likely to be extensive as well. A number of proteases can specifically cleave a variety of intracellular proteins, resulting in C-terminal fragments that often bear destabilizing N-terminal residues of the Ubr1-mediated branch of the ubiquitin-dependent N-end rule pathway (FIG. 5C). Such fragments are often short-lived in vivo, thereby regulating specific circuits. Given the major expansion of the N-end rule in the present work (FIG. 4), most in vivo-produced C-terminal fragments of intracellular proteins should now be viewed, a priori, as putative targets of the Doa10 or Ubr1 branches of the ubiquitin-dependent N-end rule pathway. The topologically unique location of N-terminal residues, their massive involvement in proteolysis, and their extensive modifications make N-degrons a particularly striking example of the scope and subtlety of regulated protein degradation (FIG. 4 and FIG. 5C).

As an experimentally observed but formal (non-mechanistic) relation between the in vivo half-life of a protein and the identity of its N-terminal residue, the N-end rule does not place constraints on the nature of processing steps (such as proteolytic cleavages) or specific enzymes (such as Nt-acetylases, R-transferases or N-recognins) that produce N-degrons and implement the N-end rule pathway (FIG. 4 and FIG. 1C). For example, although prokaryotes employ Ub-independent N-recognins such as ClpS (instead of N-recognin Ub ligases in eukaryotes), and the leucylation of secondary destabilizing N-terminal residues (instead of arginylation in eukaryotes), the resulting prokaryotic pathways are clearly N-end rule pathways. An N-degron is classed as such if the N-terminal residue of a protein (unmodified or covalently modified) is an essential determinant of that protein's degradation signal. This function-based definition does not specify molecular devices that create, recognize or regulate N-degrons. It is also compatible with any route through which a destabilizing residue becomes N-terminal in a polypeptide. By this definition, N-terminal degradation signals whose activity requires N-terminal acetylation (Nt-acetylation) are a subset of N-degrons, termed $^{Ac}$N-degrons, in the N-end rule pathway (FIG. 4 and FIG. 5C).

Figure 13:
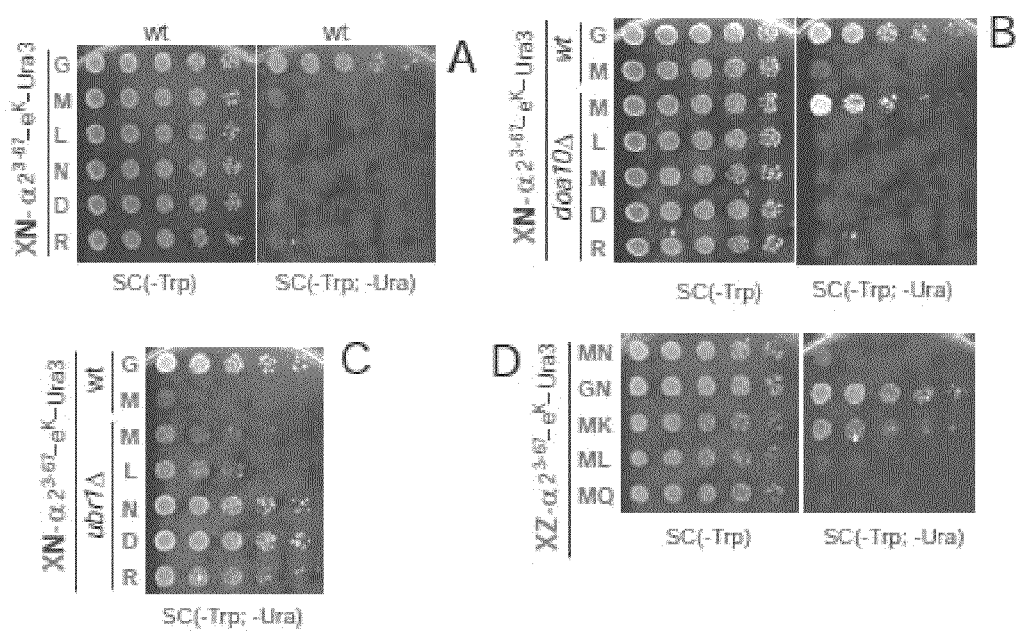
FIG. 13 illustrates the cell growth assays with XZ-α2$^{3-67}$-e$^K$-Ura3 in wild-type and mutant yeast. In vivo levels of Ura3 determine S. cerevisiae growth rates in the absence of uracil in the medium, making it possible to compare the rates of degradation of Ura3 fusions through the use of growth assays. We carried out such assays, shown here, in wild-type, doa10Δ and ubr1Δ, and also in cells lacking specific subunits of Nt-acetylases. The reporters were Deg1-bearing XZ-α2$^{3-67}$-e$^K$-Ura3 fusions (X=Met, Gly, Leu, Asn, Asp, Arg; Z=Asn, Lys, Leu, Gin), with cell growth rates compared by serial dilutions on uracil-containing (SC(-Trp) versus uracil-lacking (SC(-Trp, -Ura)) plates. The results of these assays (panels A-D) were entirely consistent with other findings, including the necessity of Nt-acetylation of N-terminal Met for the recognition of MZ-α2$^{3-67}$-e$^K$-Ura3 by Doa10. (A) XN-α2$^{3-67}$-e$^K$-Ura3 (X=Gly, Met, Leu, Asn, Asp, Arg) in wild-type (wt) cells. (B) XN-α2$^{3-67}$-e$^K$-Ura3 (X=Gly, Met) and XN-α2$^{3-67}$-e$^K$-Ura3 (X=Met, Leu, Asn, Asp, Arg) in wild-type and doa10Δ cells, respectively. (C) XN-α2$^{3-67}$-e$^K$-Ura3 (X=Gly, Met) and XN-α2$^{3-67}$-e$^K$-Ura3 (X=Met, Leu, Asn, Asp, Arg) in wild-type and ubr1Δ cells, respectively. (D) XZ-α2$^{3-67}$-e$^K$-Ura3 (XZ=Met-Asn, Gly-Asn, Met-Lys, Met-Leu, Met-Gin) in wild-type cells.

At least the bulk of degradation of CZ-e$^K$-Ura3 (Z=Leu, Trp, Val, Asp, Gly, He, Pro), SL-e$^K$-Ura3, and ML-e$^K$-Ura3 did not require Ubr1, the Ub ligase of the previously known branch of the N-end rule pathway (FIG. 1B, FIG. 5C, and FIG. 7F). In addition, CL-e$^K$-Ura3 and SL-e$^K$-Ura3 remained short-lived in S. cerevisiae strains that lacked both Ubr1 and the Ubr2 or Ufd4 Ub ligases (FIG. 7F). Results of Ura3-based growth assays with XN-α2$^{3-67}$-e$^K$-Ura3 (XNα2) (X=M, G, R) and either doa10Δ or ubr1/1 mutants (FIG. 13) were in agreement with other data in this study. The sequence of S. cerevisiae Ubr2 is similar to that of Ubr1, but Ubr2 does not function in the N-end rule pathway. Ufd4 mediates the UFD (Ub-fusion-degradation) pathway and functionally interacts with Ubr1. Interestingly, the Doa10-dependent degradation of XZ-e$^K$-Ura3 reporters such as CL-e$^K$-Ura3 and SL-e$^K$-Ura3 was accelerated in the absence of the Ufd4 Ub ligase and also in the absence of both Ufd4 and Ubr1 (FIG. 7F, lanes 7-10 and 17-20; cf lanes 11, 12). A similar effect was observed in the absence of the Ubr2 Ub ligase (FIG. 7F, lanes 3-6). These findings suggest a cross-regulation of the activities and/or levels of specific Ub ligases in a network that remains to be explored.

As described in the main text, FIG. 3, FIG. 6C, D and FIG. 11, our current survey of S. cerevisiae proteins for the presence of $^{Ac}$N-degrons has encompassed Tbf1, Slk19, Ymr090w, His3, Pop2, Hsp104, Tho1, Ubp6, and Aro8, in addition to MARC. With reporters such as XZ-e$^K$-Ura3 (FIG. 5D), the loss of an $^{Ac}$N-degron was manifested, in particular, by "time-zero" increases, i.e., by significantly augmented levels of (stabilized) test proteins before a CHX-chase (e.g., FIG. 1C, E, F). Analogous time-zero increases, upon inactivation of $^{Ac}$N-degrons, were observed with Tbf1, Slk19, Ymr090w, His3 and Hsp104 (FIG. 3 and FIG. 11). These increases were high with Tbf1 and Slk19, and even more striking with Ymr090w and His3 (FIG. 3A, B, C, E). Moreover, inactivation of $^{Ac}$N-degrons of Ymr090w, His3, and Hsp104 resulted in the nearly complete stabilization of these proteins (FIG. 3C, E, H), whereas Slk19 and Tbf1 were stabilized strongly but partially (FIG. 3 A, B and FIG. 11C), implying the presence of additional, Doa10-independent degradation signals.

Among these 10 yeast proteins, 8 of them (including MATα2) contained $^{Ac}$N-degrons, whereas 2 proteins, Pop2 and Tho1, apparently lacked them, despite being Nt-acetylated, according to databases of Nt-acetylated S. cerevisiae proteins (FIG. 3 and FIG. 11). Specifically, Pop2, a short-lived protein in wild-type cells, remained short-lived in doa10Δ cells that lacked the cognate Ub ligase that recognizes $^{Ac}$N-degrons (FIG. 11B). A detailed understanding of Pop2 and its degrons remains to be attained. A parsimonious interpretation is that Pop2, similarly to MATα2, contains strong Doa10-independent and Nt-acetylation-independent degradation signals. In contrast, Tho1 was found to be a long-lived protein in both wild-type and doa10Δ cells, and also in ard1Δ cells, which lacked the cognate NatA Nt-acetylase (FIG. 11E). The reasons for stability of Tho1, despite it being (apparently) Nt-acetylated, remain to be understood.

With XZ-e$^K$-Ura3 reporters, quantitation of the corresponding CHX-chases and $^{35}$S-pulse-chases clearly showed their degradation in the presence of active $^c$N-degrons, and the absence of significant degradation when these degrons were inactive, either because of the absence of the Doa10 Ub ligase or because the reporter's $^c$N-degron was inactivated by a missense mutation that abrogated the reporter's Nt-acetylation (FIG. 6A, B, FIG. 8A-C, and the main text). Analogous directly interpretable differences were observed with several natural *S. cerevisiae* proteins, including MARC, His3, Hsp104, Tbf1 and Slk19 (FIG. 2A-C, FIG. 3A, B, E, H, FIG. 6C, D and FIG. 10B-E). Interestingly, however, with some other *S. cerevisiae* proteins whose degradation was also dependent on the Doa10 Ub ligase and Nt-acetylation, the disposition was more complex. For example, the Ymr090w protein was identified as a putative Doa10 substrate using $^{35}$S-pulse-chase 2-D electrophoresis of yeast extracts from wild-type versus doa10Δ cells (FIG. 12). CHX-chase assays confirmed that the levels of the Ymr090w protein in wild-type cells were strikingly lower than their levels in doa10Δ cells (FIG. 3C, lanes 1-3; cf lanes 7-9, and FIG. 3D), indicating rapid Doa10-dependent degradation of Ymr090w in wild-type cells.

Tellingly, a major stabilization of Ymr090w could be attained independently of Doa10 as well, as the levels of Ymr090w were also strongly increased in ard1Δ cells, which lacked the cognate NatA Nt-acetylase (FIG. 3D). Finally and independently, a strong increase of Ymr090w could also be observed in wild-type cells, if the wild-type Ymr090w protein (Ser-Pro-Ymr090w) was mutated to contain N-terminal Gly (Gly-Pro-Ymr090w), which is rarely Nt-acetylated, in contrast to N-terminal Ser (FIG. 3C). However, unlike the rapid in vivo degradation of, for example, ML-e$^K$-Ura3 or His3 in wild-type cells that could be detected by CHX-chase assays (FIG. 6A, C), the same assay with Ymr090w showed a relatively slow decay of the initially low ("residual") levels of wild-type Ymr090w in wild-type cells (FIG. 3C; compare, for example, with FIG. 3E and FIG. 6A for His3). A plausible and parsimonious interpretation of the relative "flatness" of decay curves of the remaining (small) amount of wild-type Ymr090w that was still detectable in wild-type cells (FIG. 3C, lanes 1-3) is that this protein was only partially Nt-acetylated. Under these circumstances, the major (Nt-acetylated) subset was degraded quickly, whereas the minor, unacetylated subset was long-lived in wild-type cells, thus accounting for the above data with Ymr090w. Databases of Nt-acetylated proteins confirm a partial (significantly less than 90%) Nt-acetylation of some proteins. Moderate overexpression of a protein, as was done in the present study, may further decrease the extent of its Nt-acetylation and thereby produce a relatively long-lived subset of an otherwise short-lived Nt-acetylated protein. This explanation, which remains to be definitively verified, can account for CHX-chase patterns observed with proteins such as Ymr090w (FIG. 3C, D; cf. FIG. 3E).

Given the ubiquity of $^{Ac}$N-degrons (FIG. 4) and the long history of Nt-acetylation studies, it might be instructive to comment on reasons for missing these degrons in both our own and other earlier work. A 1984 study with fractionated reticulocyte extracts employed cyanate at pH 6 to preferentially modify the N-terminal (X—NH$_2$ group of an artificial substrate of the Ub system. The data suggested that blocking the N-terminal C1-NH$_2$ group of a substrate could inhibit its Ub-mediated degradation. One conclusion by this study was that Nt-acetylation of proteins in vivo most likely protected them from degradation, i.e., the opposite of the discovery reported in the present work. However, the absence of membranes (and thus the absence of TEB4 or other mammalian counterparts of the *S. cerevisiae* Doa10 Ub ligase) in a fractionated reticulocyte extract employed in the above study was, all by itself (in addition to other causes), a sufficient reason for not detecting $^{Ac}$N-degrons through the approach used. In other words, the findings of the above investigation are neutral vis-a-vis the results of the present work.

*S. cerevisiae* contains several Nt-acetylases, including NatA, NatB, NatC and NatD. Their substrate specificities are distinct but partially overlapping. In a screen with a Deg1-Ura3 fusion (Deg1 is the 67-residue N-terminal region of MATα2), this reporter was stabilized in the absence of Nat3, the catalytic subunit of the NatB Nt-acetylase. That previously unexplained finding can now be understood as resulting from the down-regulation of the $^{Ac}$N-degron in Deg1, since its Nt-acetylation would be decreased in the absence of NatB (FIG. 4).

The initial discovery of the N-end rule, i.e., the identification of what is now understood as the Ubr1-mediated branch of the N-end rule pathway (FIG. 5C), employed the Ub fusion technique, in vivo degradation reporters, and the ~40-residue N-terminal sequence referred to as the e$^K$ extension (see the main text and FIG. 5D). The original e$^K$ contained His, a basic residue, at position 2 and yielded long-lived reporters with N-terminal Met or Cys residues. As shown in the present work, the other basic residues (Lys or Arg) at position 2 of the eK extension also yield long-lived CK-e$^K$-Ura3, MK-e$^K$-Ura3 and MR-e$^K$-Ura3, in contrast to a non-basic residue such as Leu at position 2, which yields short-lived CL-e$^K$-Ura3 and ML-e$^K$-Ura3 (FIG. 1A-D, FIG. 7A, C, and FIG. 8A-C). Thus, the presence of a basic residue at position 2 precludes the destabilizing activity of N-terminal residues such as Met or Cys. Crucially, the Nt-acetylation of N-terminal Met, Ala, Val, Ser, Thr and Cys is required for their destabilizing activity (FIG. 4). Thus, a basic residue at position 2 is expected to either preclude or diminish the Nt-acetylation of the above N-terminal residues. In agreement with these results, the databases of Nt-acetylated *S. cerevisiae* proteins indicate that proteins with Lys at position 2 are virtually never Nt-acetylated. Nt-acetylated proteins with the other basic residues, Arg or His, at position 2 are present in databases but are significantly under-represented. Thus, although the e$^K$ extension was a key tool in the initial finding of the N-end rule pathway, the presence of His at position 2 in the original e$^K$ extension has precluded the detection of $^{Ac}$N-degrons until the present work.

$^{Ac}$N-degrons are produced either directly by Nt-acetylation of N-terminal Met or through sequential action of Met-aminopeptidases and Nt-acetylases (FIG. 4). A major role of $^{Ac}$N-degrons is likely to involve quality control mechanisms and regulation of protein stoichiometries in a cell. As briefly discussed in the main text, a key feature of such mechanisms would be conditionality of $^{Ac}$N-degrons. Errors in specific steps that underlie protein synthesis result in 5% to 20% of molecules of a 50 kDa protein containing at least one missense substitution. Premature termination of translation and frameshifts are other sources of defective polypeptides. The misfolding and aggregation of mistranslated proteins, and the resulting toxicity are significant even in the absence of environmental insults or genes that encode overtly defective proteins. The expected contribution of $^{Ac}$N-degrons to the degradation of misfolded and/or unassembled proteins remains to be addressed.

Degradation assays with C-terminally tagged S. cerevisiae proteins (FIG. 3, FIG. 6C, D, and FIG. 11) involved a moderate overexpression of these proteins, a circumstance that is likely to augment the activity of $^{Ac}$N-degrons (see above). Note, however, that the increased levels of untagged His3, Ymr090w and Aro8 in 2-D electrophoresis-based $^{35}$S-pulse-chases with wild-type versus doa10Δ cells (FIG. 12) indicated that $^{Ac}$N-degrons can be active in endogenous, non-overexpressed proteins as well.

A conditionality of $^{Ac}$N-degrons may underlie the proteolysis-mediated regulation of protein assembly into multiprotein complexes. For example, ribosomal proteins, proteasomal subunits and histones are usually short-lived until they become integrated into larger assemblies—the ribosomes, proteasomes and chromosomes, respectively. Degradation of these proteins in their unassembled states makes possible the regulation of their levels vis-a-vis the rates of their production through transcription and translation. Nearly nothing is known about specific degrons of ribosomal proteins, proteasomal subunits and histones that underlie this conditional degradation. However, it is known that most histones, ribosomal proteins, and subunits of the proteasome are Nt-acetylated. We suggest that assembly-regulated protein degradation may be mediated, at least in part, by $^{Ac}$N-degrons that form cotranslationally and are accessible to a Ub ligase such as Doa10 in "free" proteins but not in their "assembled" counterparts. In this model, a minority of proteins (e.g., some ribosomal proteins) that are not Nt-acetylated would be targeted for the assembly-regulated proteolysis through degradation signals other than $^{Ac}$N-degrons.

The regulation of in vivo protein stoichiometries through $^{Ac}$N-degrons may encompass not only the largest and most abundant protein-based assemblies such as chromosomes, ribosomes and proteasomes but other oligomeric proteins as well. Aneuploidy (a disposition in which the chromosome number in a cell is not an exact multiple of the haploid number) is a frequent property of cancer cells and a source of physiological perturbations such as in Down syndrome (a trisomy of chromosome 21). These perturbations may be caused, to a large extent, by improper initial protein stoichiometries in aneuploid cells, given their deviations from wild-type gene dosages on over-represented or under-represented chromosomes. Such cells appear to respond by selectively degrading a higher than normal load of unassembled proteins. This circumstance may account for the known hypersensitivity of aneuploid cells to proteasome inhibitors. If so, and if $^{Ac}$N-degrons play a significant role in protein assembly-regulated proteolysis, aneuploid cancer cells may prove to be hypersensitive to selective inhibition of TEB4 and other human counterparts of the yeast Doa10 Ub ligase. N-acetyl-cysteine (NAC) apparently reduces the incidence and progression of some cancers. Such effects of NAC are currently ascribed to its activity as an antioxidant. A mutually nonexclusive possibility is that NAC and other Nt-acetylated amino acids (and/or short Nt-acetylated peptides) might act as competitive inhibitors of the Doa10 Ub ligase and its mammalian counterparts.

S. cerevisiae lacking the Doa10 Ub ligase exhibit mild defects, in comparison to abnormalities of cells that lack specific Nt-acetylases. One explanation of this dichotomy is that cessation of Nt-acetylation (as distinguished from the loss of activity of $^{Ac}$N-degrons) may impinge on the functioning of some proteins in which the N$^\alpha$-terminal acetyl moiety plays non-proteolytic roles. Thus far, only ~10 proteins (a tiny minority of thousands of Nt-acetylated proteins in every eukaryote) have been identified, or inferred, as proteins that require Nt-acetylation for their in vivo roles, which are apparently unrelated to protein degradation.

Recent studies indicated that the in vivo level of acetyl-CoA, the co-substrate of protein acetylases, including Nt-acetylases, is under metabolic control and can be rate-limiting for acetylation. For example, the concentration of acetyl-CoA is ~5-fold higher in undifferentiated embryonic stem (ES) cells than in their differentiated counterparts. Because $^{Ac}$N-degrons (FIG. 4) are likely to be the most prevalent class of degradation signals in cellular proteins, a cell might be able to regulate a large fraction of protein degradation by changing the levels of acetyl-CoA. If an enzyme that produces acetyl-CoA is Nt-acetylated and thereby contains an $^{Ac}$N-degron, this enzyme may be a part of a feedback circuit that regulates the levels of acetyl-CoA in a cell. For example, an increase in acetyl-CoA would lead to a faster and/or more complete Nt-acetylation of an acetyl-CoA synthetase, and therefore would augment its Nt-acetylation-dependent degradation, resulting in a homeostatic reduction of acetyl-CoA levels. The membrane-embedded TEB4, a human counterpart of S. cerevisiae Doa10, is a metabolically unstable Ub ligase that apparently targets itself for degradation, suggesting a similar self-regulating circuit for the yeast Doa10 as well. The N-termini of TEB4 and Doa10 (Met-Asp in both proteins) are exposed to the cytosol and are conducive to Nt-acetylation. The resulting Nt-acetylation-dependent, Doa10-dependent degradation of Doa10 itself (or the TEB4-dependent degradation of TEB4) would add a specific feedback to regulatory pathways that involve $^{Ac}$N-degrons and their cognate Ub ligases.

In contrast to nucleus-encoded eukaryotic proteins, the nascent proteins in bacteria such as E. coli, and in eukaryotic organelles such as mitochondria and chloroplasts, contain the N$^\alpha$-terminally formylated Met (f-Met) residue. The f-Met is derived from the initiator f-Met-tRNA, and is deformylated to Met by a ribosome-associated deformylase. The physiological function of the N-formyl group in f-Met is unknown. Given the similarity of N-formyl and N-acetyl groups, and by analogy with eukaryotic $^{Ac}$N-degrons, we suggest that the N-terminal f-Met may function as a formyl-dependent degradation signal, despite the transiency of its N-formyl moiety. This possibility is consistent with data showing that some proteins made in a chloroplast become more unstable under conditions of diminished deformylation, although the authors of the cited study interpreted their findings as an indication that Met itself, rather than the N-formyl group, was the relevant instability determinant.

EXAMPLES

For further illustration of various aspects of the present disclosure, several specific examples will now be described. It should be understood however that these examples are for illustrative purposes only, and are not intended to limit the scope of the present disclosure.

Example 1

Yeast Strains, Media and Genetic Techniques

S. cerevisiae strains used in this study are described in Table 1. Standard techniques were employed for strain construction and transformation. The strains CHY248, CHY223, or CHY229 were produced using PCR-derived KanMX6 modules. The strains CH287 and CHY288 were constructed by disrupting UBC4 in BY4742 and BY 17299 (Table 1) through a PCR-mediated gene targeting that employed the pRS315 plasmid, similarly to a previously described procedure. E2, E3 and N-acetyltransferase (Nt-acetylase) mutant strains used in this study were from the Varshaysky laboratory's strain collection or from Open Biosystems (Huntsville, Ala.). *S. cerevisiae* media included YPD (1% yeast extract, 2% peptone, 2% glucose; only most relevant components are cited); SD medium (0.17% yeast nitrogen base, 0.5% ammonium sulfate*2% glucose); and synthetic complete (SC) medium (0.17% yeast nitrogen base, 0.5% ammonium sulfate, 2% glucose), plus a drop-out mixture of compounds required by a given auxotrophic strain.

Example 2

Test Proteins and Construction of Plasmids

The plasmids used in this study are described in Table 2. The low copy (CEN) plasmid pCH178, which expressed Ub-CK-$e^K$-Ura3 (Ub-Cys-Lys-$e^K$-ha-Ura3) from the $P_{CUP1}$ promoter was derived from the pRS314 vector. To construct pCH178, a ubiquitin (Ub)-gene fragment from the pMET416$_F$UPRCUP9$_{NSF}$ plasmid was PCR-amplified (using primers OCH201 and OCH214 (Table 3), digested with EcoJWBamHI and thereafter subcloned into EcoRI/BamHI-cut pBAM (Table 2). pCH669, pCH508 or pCH509 were constructed by subcloning relevant DNA fragments from SacI/XhoI-cut pCH504, pCH505 or pCH506 that expressed ML-$e^K$-Ura3, SL-$e^K$-Ura3 or TL-$e^K$-Ura3, respectively, into SacI/XhoI-cut pRS313 vector. To produce other plasmids that expressed XZ-e-Ura3 proteins, the corresponding EcoRI/BamHI-digested PCR-produced fragments encoding Ub-XZ-$e^K$-Ura3 (X and Z denote varied residues) were subcloned into EcoRI/BamHI-cut pBAM vector or pCH508 (Table 2).

*S. cerevisiae* Tbf1 is a 63 kDa (N-terminal Met-Asp) transcriptional activator and regulator of telomere length. The 95 kDa SIk19 (N-terminal Met-Asn) is a kinetochore-associated regulator of chromosome segregation The 25 kDa Ymr090w (N-terminal Ser-Pro) is a cytosolic protein of unknown function, with sequence similarities to DTDP-glucose 4,6-dehydratases. The 24 kDa His3 (N-terminal Thr-Glu) is imidazole glycerophosphate dehydratase (IGPD), an enzyme of histidine biosynthesis. The 50 kDa Pop2 (N-terminal Met-Gin) is a subunit of a complex that deadenylates mRNAs. The 102-kDa Hsp104 (N-terminal Met-Asn) is a chaperone and heat stress protein. The 56 kDa Aro8 (N-terminal Thr-Leu) is an aromatic aminotransferase that participates in particular, in the biosynthesis of phenylalanine. The 57 kDa Ubp6 (N-terminal Ser-Gly) is a deubiquitylating enzyme associated with the 26S proteasome. The 24 kDa Tho1 (N-terminal Ala-Asp) is a nuclear RNA-binding protein.

The open reading frame (ORF) encoding TBF1ha with a C-terminal ha tag was subcloned into the low-copy (CEN) pRS316 vector, and was expressed from the vector's $P_{CUP1}$ promoter. The TBF1$_{ha}$ ORF was produced by PCR, using *S. cerevisiae* genomic DNA and specific primers for DNA fragments encoding wild-type $^{MD}$Tbf1$_{ha}$ (with N-terminal Met-Asp), the mutant $^{MK}$Tbf1$_{ha}$ (with Lys at position 2), and the mutant $^{MG}$Tbf1$_{ha}$ (with N-terminal Gly, after removal of N-terminal Met by MetAPs). Similar procedures were used to construct and amplify DNA fragments encoding wild-type $^{MN}$Slk19$_{ha}$ (with N-terminal Met-Asn); mutant $^{MK}$Slk19$_{ha}$ (with Lys at position 2); mutant $^{Mg}$Slk19$_{ha}$ (with N-terminal Gly); wild-type $^{MS}$Ymr090w$_{ha}$ (with N-terminal Met-Ser); mutant $^{MK}$Ymr090w$_{ha}$ (with Lys at position 2); mutant $^{MG}$Ymr090w$_{ha}$ (with N-terminal Gly); wild-type $^{MT}$His3$_{ha}$ (with N-terminal Met-Thr); wild-type $^{MQ}$Pop2$_{ha}$ (with N-terminal Met-Gin); wild-type $^{MN}$Hsp104$_{ha}$ (with N-terminal Met-Asn); mutant $^{MK}$Hsp104h$_{a}$ (with Lys at position 2); and also wild-type Aro8$_{ha}$, Ubp6$_{ha}$, and Tho1$_{ha}$—These DNA fragments were digested with BamHI/NotI or EcoRI/XhoI and subcloned into BamHI/NotI-cut pRS316-CUP1 or EcoRI/XhoI-cut pCH508.

To construct a library of plasmids encoding Ub-CZ-$e^K$-Ura3 (Z=any residue except Tip, Gin, Glu, Lys), EcoRI/BamHI-digested, PCR-amplified Ub gene fragment from pBAM (Table 2) were subcloned into EcoRI/BamHI-cut pCH178 (Table 2), followed by transformation of *E. coli* DH5a. PCR primers used for the above amplification were OCH201 (GGG <u>GAATTC</u> ATG CAG ATT TTC GTC AAG ACT TTG GTC (SEQ ID NO:6), EcoRI site underlined) and OCH202 (AAA <u>GGATCC</u> RNN ACA ACC ACC TCT TAG CCT TAG CAC AAG (SEQ ID NO:7), R=A, G; N=A, C, G, T; BamHI site underlined). EcoRI/BamHI-digestion of 20 randomly retrieved plasmids from transformants suggested correct insertions in more than 90% of plasmids in this library. After pooling—1,000 *E. coli* transformants, a plasmid DNA preparation was made and thereafter used as the CZ-$e^K$-Ura3 library.

pCH535, which expressed $^{MN}$MATα2$^{3-67}$-$e^K$-Ura3, was constructed by subcloning a SacII/BamHI-digested DNA fragment (produced by PCR from *S. cerevisiae* genomic DNA and the primer pairs OCH817 and OCH833 (Table 3) into SacII/BamHI-cut pCH178. pCH641 (Table 2) was produced by inserting SacI/XhoI-cut pCH535 into SacI/XhoI-cut p416MET25. To construct pCH645, SacII/KpnI-digested pCH535 (Table 2) was subcloned into SacII/KpnI-cut pH$_{10}$UE, yielding pCH622. Thereafter BamHI/HindIII-cut pEJJ-M was subcloned into pCH622 (Table 2), yielding pCH645. To construct pCH595, a DNA fragment containing a 5'-proximal part of the *S. cerevisiae* DOA10 ORF, a SmaI site and a 3-proximal part of the DOA10$_f$ fragment was PCR-amplified using the primers OCH901 and OCH902 (Table 3). The resulting DNA fragment was subcloned into BamHI/XhoI-cut p425GAL1 vector, yielding pCH581. That plasmid was digested with SmaI and transformed into the SC295 *S. cerevisiae* strain to clone C-terminally flag-tagged DOA10 using gap repair. The resulting pCH595 plasmid (Table 2) expressed Doa10$_f$ from the $P_{GAL1}$ promoter of the high copy pRS425GAL1 plasmid.

pCH704, pCH705, or pCH706, which expressed XZ-MATα2$^{3-210}_f$ from the $P_{MET25}$ promoter on a low copy plasmid, were constructed by inserting the BamI/XhoI-digested, C-terminally flag-tagged MATα2$_f$ORF (produced by PCR from *S. cerevisiae* genomic DNA and the primer pairs OCH989/OCH819, OCH990/OCH819 or OCH991/OCH819 (Table 3) into the p416MET25 vector (Table 2). pCH719, expressing MATα2$_f$ as Ub-reference fusions (see FIG. 9D, E), were constructed by subcloning SacII/XhoI-cut MATα2$_f$ ORF (PCR-produced using the primer pairs OCH817/OCH819 (Table 3) into SacII/XhoI-cut pMET416$_F$UPRCUN$_{NSF}$ (Table 2). Construction details for other plasmids are shown in Table 2. All final constructs were verified by DNA sequencing.

Example 3

Screening a Library of CZ-$e^K$-Ura3 Fusions

CZ-$e^K$-Ura3 library plasmids were transformed into *S. cerevisiae* JD52 (Table 1) and thereafter plated on SC(-Trp; -Ura; +FOA (1 mg/ml); +CuSO$_4$ (10 uM)). Among –6,200 transformants, ~165 colonies were formed on these FOA-based plates, with selection for low levels of Ura3. After streaking and re-growing FOA-resistant transformants on the same medium for 2 days at 30° C., 80 colonies were re-isolated. Plasmids were retrieved from these colonies and initially analyzed using BamHI/EcoRI digestion and gel electrophoresis, followed by a partial sequencing of 51 plasmids. Although most CZ-e$^K$-Ura3 fusions that yielded low levels of Ura3 activity resulted from truncating mutations in the Ub or Ura3 moieties, three low-Ura3 isolates (Z=Leu, Val, Pro) encoded intact Ub and Ura3. These fusions were analyzed using degradation assays.

Example 4

Purification of Ub-XZ-MATα2$^{3-67}$-e$^K$-DHFR$_{ha}$ and In Vitro Deubiquitylation The plasmids pCH645, pCH646, pCH647, and pCH648, which encoded His$_{10}$Ub-XZ-α2$^{3-67}$-e$^K$-DHFR$_{ha}$ (X=Met, Gly, Arg; Z=Asn, Lys), were transformed into BL21(DE3) CodonPlus E. coli cells (Stratagene, La Jolla, Calif.). 50-ml overnight culture of transformed cells was inoculated into 800 ml of LB medium containing 100 µg/ml ampicilin and 34 µg/ml chloramphenicol, followed by growth at 37° C. to A$_{600}$ of ~0.6. Expression of His$_{10}$Ub-XZ-α2$^{3-67}$-e$^K$-DHFR$_{ha}$ was induced with isopropyl β-D-thiogalactoside (IPTG) at 0.2 mM for 4 hr at 30° C. His$_{10}$Ub-XZ-α2$^{3-67}$-e$^K$-DHFR$_{ha}$ fusion proteins were purified by affinity chromatography with Ni-NTA resin (Qiagen, Valencia, Calif.). Briefly, E. coli cells were harvested by centrifugation and frozen at −80° C. Cell pellets were thawed and resuspended in Ni-NTA binding buffer (10% glycerol, 20 mM imidazole, 0.3 M NaCl, 10 mM β-mercaptoethanol, 1 mM PMSF, 50 mM NaH$_2$PO$_4$/Na$_2$HPO$_4$ (pH 7.5)) containing 1× Protease Inhibitor Cocktail "for use in purification of histidine-tagged proteins" (Sigma-Aldrich, St. Louis, Mo.). Cells were disrupted by sonication, 5 times for 1 min each at 1-min intervals, followed by the addition of NP40 to the final concentration of 0.1%. After centrifugation of the extract at 11,200 g for 30 min, the supernatant was added to 2 ml of Ni-NTA resin (Qiagen, 50% slurry), and incubated for 2 hr at 4° C. The resin was transferred to a 10-ml column and washed 4 times with 50 ml of washing buffer (10% glycerol, 50 mM imidazole, 0.3 M NaCl, 10 mM β-mercaptoethanol, 50 mM NaH$_2$PO$_4$/Na$_2$HPO$_4$, pH 7.5). His$_{10}$Ub-XZ-α2$^{3-67}$-e$^K$-DHFR$_{ha}$ proteins were then stepwise eluted using 2-ml samples of the binding buffer that contained increasing concentrations of imidazole (100, 150, 200, 250, 300 mM). Pooled eluted samples were dialyzed overnight at 4° C. against storage buffer (10% glycerol, 0.15 M NaCl, 10 mM β-mercaptoethanol, 50 mM NaH$_2$PO$_4$/Na$_2$HPO$_4$, pH 7.5). Thus purified His$_{10}$Ub-XZ-α2$^{3-67}$-e$^K$-DHFR$_{ha}$ proteins (~1 mg) were digested with purified Usp2-cc deubiquitylating enzyme (0.1 mg overnight at 4° C. in 1 ml of cleavage buffer (10% glycerol, 0.3 M NaCl, 2 mM β-mercaptoethanol 50 mM NaH$_2$PO$_4$/Na$_2$HPO$_4$, pH 7.5). His$_{to}$-tagged (SEQ ID NO:8) ubiquitin and His$_6$-tagged (SEQ ID NO:9) Usp2-cc were removed by incubation with Ni-NTA (0.5 ml) for 1 h at 4° C. The unbound proteins were dialyzed against second storage buffer (10% glycerol, 0.15 M NaCl, 5 mM β-mercaptoethanol, 50 mM HEPES, pH 7.5) and frozen at −80° C.

Example 5

In Vitro Acetylation Assay

A sample of purified XZ-MATα3$^{3-67}$-e$^K$-DHFR$_{ha}$s (~15 µg) was incubated in 20 µl of anti-ha agarose (50% slurry) (Sigma-Aldrich) on ice for 30 min, was further washed in 0.25 ml of lysis buffer (10% glycerol, 0.15 M NaCl, 1 mM PMSF, 50 mM HEPES (pH 7.5)) containing 1× protease inhibitor cocktail "for use with fungal and yeast extracts" (Sigma-Aldrich). Whole-cell extracts from wild-type (BY4742; Table 1) S. cerevisiae were passed through the Protein Desalting Spin columns (Thermo Scientific, Rockford, Ill.). Samples of XZ-α3$^{3-67}$-e$^K$-DHFR$_{ha}$ bound to anti-ha-agarose beads were incubated in 0.1 ml of a reaction mixture (0.1 mg crude extract, 5 mM Na-butyrate (Sigma-Aldrich), 0.2 µCi C$^{14}$-Acetyl-Coenzyme A (Ac-CoA) (1.85 Mbq) (Perkin-Elmer, Fremont, Calif.) for 1 hr at 30° C. After washing the beads 3 times with 0.4 ml of lysis buffer, the bound proteins were eluted and fractionated by SDS-12% PAGE (Tris-glycine), followed by autoradiography with X-ray films, at −80° C. for 30 days.

Example 6

Antibody Specific for Nt-Acetylated N-Terminal Sequence of MATα2

The Nt-acetylated synthetic peptide $^{Ac}$MNKIPIKDLLNC (SEQ ID NO:1) and its unacetylated counterpart MNKIP-IKDLLNC (SEQ ID NO:10) were produced and purified by Abgent (San Diego, Calif.). Except for C-terminal Cys (used for conjugation of peptides to keyhole limpet hemocyanin), the amino acid sequence of these peptides was identical to the N-terminal region of MATα2. Standard procedures were employed by Abgent to produce rabbit antisera to $^{Ac}$MNKIP-IKDLLNC (SEQ ID NO:1). Antibodies that bound to $^{AC}$MNKIPIKDLLNC (SEQ ID NO:1) were selected from immune sera by affinity chromatography on a resin derivatized with this Nt-acetylated peptide. The resulting samples were then "negatively" selected by passing them through a resin derivatized with MNKIPIKDLLNC (SEQ ID NO:10), the unacetylated counterpart of $^{Ac}$MNKIPIKDLLNC (SEQ ID NO:1). The resulting antibody, termed anti-$^{AcNt}$MATα2, was highly specific for Nt-acetylated MATα2, and was employed to directly detect Nt-acetylated species of a Matα2-derived reporter in S. cerevisiae extracts (see Results). Immunoblotting with anti-$^{AcNt}$MATα2 (0.5 µg/ml) was carried out for 4 h at room temperature (RT) in 5% skin milk in PBST (PBS containing 0.5% Tween-20). The bound anti-$^{AcNt}$-MATα2 was detected using the Odyssey Imaging System (Li-Cor, Lincoln, Nebr.) and a goat anti-rabbit antibody (at 1:5,000 dilutions) that was conjugated to IRDye-680 (Li-Cor).

Example 7

Cycloheximide-Chase Degradation Assay

S. cerevisiae were grown to A of 0.8 to 1.0 in plasmid-maintaining (selective) liquid media at 30° C., followed by treatment with cycloheximide (CHX), at the final concentration of 0.1 mg/ml). At indicated times, cell samples (corresponding to 1 ml of cell suspension at A$_{600}$ of 1) were harvested by centrifugation for 30 sec at 11,200 g, and resuspended in 1 ml of 0.2 M NaOH, for 20 min on ice, or for 5 min at room temperature, followed by centrifugation for 30 sec at 11,200 g. Pelleted cells were resuspended in 50 ul of HU buffer (8 M urea, 5% SDS, 1 mM EDTA, 0.1 M dithiothreitol (DTT), 0.005% bromophenol blue, 0.2 M Tris-HCl, pH 6.8) containing 1× protease inhibitor cocktail "for use with fungal and yeast extracts" (Sigma-Aldrich), and heated for 10 min at 70° C. After centrifugation at 5 min at 11,200 g, 10 µl of supernatant was fractionated by SDS-4-12% NuPAGE (Invitrogen, Carlsbad, Calif.), followed by immunoblotting with anti-ha (1:2,000) and anti-tubulin (1:4,000) antibodies (Sigma-Aldrich). Quantitation of CHX-chase immunoblotting patterns (see FIG. 6) were carried out using the ImageJ software (http://rsb.info.nih.gov/iyindex.html).

Example 8

$^{35}$S-Pulse-Chase Degradation Assays $^{35}$S-pulse-chase experiments were performed essentially as described, with slight modifications. S. cerevisiae BY4742 (wild type), BY17299 (doa10Δ), BY15546 (nat3Δ), and CHY287 (ubc4Δ), or CHY288 (ubc4Δ doa10Δ) that carried either p416MET25, pCH704, pCH705, pCH706 or pCH719 were grown at 30° C. to $A_{600}$ of ~1 in 10 ml of SD medium with required amino acids for auxotrophic growth. Cells were pelleted by centrifugation and washed with 0.8 ml of SD medium with required amino acids. Cell pellets were gently resuspended in 0.4 ml of the same medium and labeled for 5 min at 30° C. with 0.16 mCi of $^{35}$S-EXPRESS (Perkin-Elmer). Cells were pelleted again and resuspended in 0.3 ml of SD medium containing cold 10 mM methionine and 5 mM cysteine and required amino acids. Samples (0.1 ml) were taken at the indicated time points, followed by preparation of extracts, immunoprecipitation with anti-flag agarose, SDS-4-12% NuPAGE, and autoradiography. In other, similar $^{35}$S-pulse-chase experiments, S. cerevisiae JD53 expressing either pCH178, pCH195, pCH504 or pCH547 were grown at 30° C. to $A_{600}$ of ~1 in 10 ml of SC(-Trp) medium containing 10 µM CuSO$_4$ and required amino acids. Pulse-chases were then preformed as described above, in SD medium with 10 µM CuSO$_4$ and required amino acids.

For $^{35}$S-pulse-chase assays that involved 2-D electrophoresis (FIG. 12 and data not shown), S. cerevisiae BY4742 (wild type) or BY17299 (doa10Δ) that carried pCH641 (Table 2) were grown at 30° C. to $A_{600}$ of ~0.8 in 200 ml of SD medium with required amino acids and 0.1 mM CuSO$_4$. Cells were pelleted by centrifugation and washed with 10 ml of SD medium with required amino acids and 0.1 mM CuSO$_4$, followed by incubation for 30 mM at 30° C. in the same medium that lacked methionine and cysteine. Cells were harvested by centrifugation. The pellets were gently resuspended in 20 ml of the same medium and labeled for 15 min at 30° C. with 2 mCi of $^{35}$S-EXPRESS (Perkin-Elmer). Cells were pelleted again and resuspended in 20 ml of SD medium containing unlabeled 10 mM methionine and 5 mM cysteine, required amino acids, and 0.1 mM CuSO$_4$. Samples (10 ml) were taken at 0 and 3-hr time points, followed by preparation of extracts, using the Sample Buffer Mailing kit (Kendrick laboratories, Madison, Wis.). 2D-electrophoretic analyses and autoradiography of our samples were carried out by Kendrick Laboratories, Inc. The first-dimension isoelectric focusing was performed using IEF tube gel containing 2% pH 4-8 mixed ampholines. The second dimension fractionation was by SDS-10% PAGE, using 22-cm long slab gels. The latter were stained with Coomassie, vacuum-dried, and subjected to autoradiography with Kodak BioMax X-ray film for 6 hr at RT. Image matching of the autoradiograms to Coomassie-stained gels was carried out manually. The relevant spots were excised from the gel, followed by their processing for in-gel digestion with trypsin and mass spectrometry (MALDI-TOF), which were performed by the Protein Analysis Facility at the Columbia University (New York, N.Y.).

Example 9

Analysis of N$^\alpha$-Terminal Acetylation by Mass Spectrometry

CHY288 (doa10Δ ubc4Δ) S. cerevisiae expressing the C-terminally flag-tagged full-length MATα2$_f$ from the $P_{GAL1}$ promoter were grown to $A_{600}$ of ~0.6 in 2 l of SC(-Ura) medium containing 0.1% glucose (instead of usual 2%), and were incubated for a further 24 hr after the addition of 30% galactose to the final concentration of 2%. Cells were harvested by centrifugation at 5,000 g for 5 min, washed in phosphate-buffered saline (PBS) and stored at -80° C. The pellets were resuspended in 10 ml of lysis buffer (10% glycerol 0.1% NP40, 0.2 M KCl, 1 mM EDTA, 5 mM β-mercaptoethanol, 1 mM PMSF, 50 mM HEPES (pH 7.5)) containing 1× protease inhibitor cocktail "for use with fungal and yeast extracts" (Sigma-Aldrich). Cells were then disrupted using a FastPrep-24 instrument (MP Biomedicals, Solon Ohio) at the speed setting of 6.5, at 20 sec/cycle, for 10 cycles. After removal of glass beads, the extracts were clarified by centrifugation at 11,2000 g for 30 min and incubated with 0.2 ml of anti-flag M2 agarose beads (50% slurry, Sigma-Aldrich) for 2 hr at 4° C. Beads were washed once in 10 ml of lysis buffer, then in 10 ml of the washing buffer (lysis buffer containing 0.5 M KCl) and finally in 10 ml of elution buffer (lysis buffer without NP40). MATα2$_f$ was eluted with 0.2 mg/ml of the flag peptide (Sigma-Aldrich) in elution buffer. The eluted Matα2$_f$ was precipitated by 20% CCl$_3$COOH (TCA) (final concentration), and washed twice with cold acetone at -20° C. Thus precipitated sample was solubilized in SDS-sample buffer, heated at 95° C. for 5 min, and fractionated by SDS-4-12% NuPAGE. Proteins were stained with Novex Colloidal Blue Staining kit (Invitrogen). The band of Matα2 (~1 µg) was excised and transferred to 0.65 ml of SafeSeal Microcentrifuge tube (Sorenson, Salt Lake City, Utah). Gel slices were incubated 2 times for 30 min at 37° C. by shaking in 0.2 ml of destaining solution (25 mM NH$_4$HCO$_3$ in 50% acetonitrile, pH 8.0). After removing destaining solution, the samples were incubated at 60° C. for 10 min in 30 µl of reducing buffer (50 mM Tris[2-carboxyethyl]phosphine (TCEP) (Thermo Scientific) in 25 mM NH$_4$HCO$_3$, pH 8.0). After cooling the sample to RT and removing the reducing buffer, gel slices were incubated in the dark at room temperature for 1 hr in 30 µl of alkylation buffer (0.1 M iodoacetamide, 25 mM NH$_4$HCO$_3$, pH 8.0). After removing the alkylation buffer, gel slices were shrank by incubating them twice for 15 min at 37° C. (with shaking) in 50 µl of acetonitrile at RT. After removing acetonitrile, gel slices were air-dried for 10 min and swelled in 25 µl of 25 mM NH$_4$HCO$_3$, pH 8.0. Thereafter Matα2 in gel slices was digested in situ with 100 ng of Asp-N endoprotease (Roche, Indianapolis, Ind.) overnight at 37° C., whereas ML-e$^K$-Ura3 (see below) was digested identically but with 100 ng of activated trypsin (Thermo Scientific). Nt-acetylated peptides in the resulting samples were analyzed by nanoscale-microcapillary reversed phase liquid chromatography and tandem mass spectrometry (cLC-MS/MS), using the QSTAR XL quadrupole time of flight mass spectrometer (Applied Biosystems, Foster City, Calif.). Acetylation sites were assigned by manual inspection of MS/MS spectra and also by using the Mascot search engine (Matrix Science, Boston, Mass.).

Similar procedures were used to analyze N$^\alpha$-terminal acetylation of the short-lived ML-e$^K$-Ura3 (ML-e$^K$-ha-Ura3) (FIG. 9B, C) and SL-e$^x$-Ura3 (SL-e$^x$-ha-Ura3). CHY223 (doa10Δ) S. cerevisiae expressing pCH504 or pCH505 (Table 1) were grown to $A_{600}$ of 3 to 4 in 1 liter of SC(-Trp) medium containing 0.1 mM CuSO$_4$. The cells were harvested by centrifugation at 5,000 g for 5 min, washed in PBS, stored at −80° C., and were processed for isolation of ML-e$^K$-Ura3 and SL-e$^K$-Ura3 identically to the steps above for MATα2$_f$, except that a cell extract was incubated with 0.4 ml of anti-ha agarose beads (50% slurry) for 2 hr at 4° C. Beads were washed in 50 ml of the lysis buffer and thereafter in 10 ml of the elution buffer (lysis buffer without NP40). ML-e$^K$-Ura3 and SL-e$^K$-Ura3 were eluted with 1 ml of the ha peptide (0.25 mg/ml; Sigma-Aldrich) in the elution buffer, and thereafter by 2 ml of 0.1 M glycine (pH 3.0). The eluted proteins were precipitated by 20% TCA. The rest of the procedure was identical to the one with MATα2$_f$, except that ML-e$^K$-Ura3 and SL-e$^K$-Ura3 were digested in situ with trypsin, without reduction/alkylation steps.

Example 10

X-Peptide Pulldown Assay with Doa10$_{myc13}$

The previously characterized X-peptide pulldown assay utilized, in the present study, a set of 12-residue synthetic peptides XNKIPIKDLLNC (SEQ ID NO:2) (X=Met, $^{Ac}$Met, Gly). Except for C-terminal Cys (added for crosslinking to beads) and the varied identity of N-terminal residue, these peptides were identical to the 11-residue N-terminal region of MATα2. We also employed 12-residue peptides XIFSTDT-GPGGC (SEQ ID NO:3) (X-Gly, Met, Arg, Phe). Except for C-terminal Gly-Gly-Cys and the varied identity of N-terminal residue, these peptides were identical to the 9-residue N-terminal region of Sindbis virus RNA polymerase (nsP4). Each peptide, synthesized by Abgent (San Diego, Calif.), was purified by HPLC to greater than 95% purity, and verified by mass spectrometry. A peptide (1 mg) was crosslinked, via its C-terminal Cys residue, to 2 ml (50% slurry) of SulfoLink Immobilization Kit for Peptides (Thermo Scientific), as described in the manufacturer's protocol. Extract from *S. cerevisiae* CHY248 cells (Table 1) containing full-length, C-terminally mycn-tagged Doa10$_{myc13}$, was diluted by lysis buffer (10% glycerol, 1% Triton X100, 0.15 M NaCl, 5 mM (3-mercaptoethanol, 1 mM PMSF, 50 mM HEPES, (pH 7.5) containing 1× protease inhibitor cocktail "for use with fungal and yeast extracts" (Sigma-Aldrich)) to 1 mg/ml of total protein. These samples also contained 50 uM bestatin (Sigma-Aldrich), an aminopeptidase inhibitor. A sample (1 ml) was transferred to a tube containing 20 µl (packed volume) of a carrier-linked 12-residue peptide, followed by gentle mixing for 2 hr at 4° C. Beads were pelleted by a brief centrifugation in a microcentrifuge, followed by three washes, for 5 min each, with lysis buffer. The beads were then suspended in 20 µl of SDS/PAGE loading buffer, and heated at 65° C. for 10 min, followed by a brief spin in a microcentrifuge, SDS-4-12% NuPAGE, and detection of Doa10$_{myc13}$ by immunoblotting with anti-myc antibody.

Example 11

Purification of Doa10$_f$ for SPOT Binding Assay

*S. cerevisiae* SC295 that carried pCH595 and expressed the C-terminally flag-tagged Doa10 (Doa10$_f$) from the P→GAM promoter and the high copy plasmid pRS425 was grown at 30° C. to A$_{600}$ of ~1 in 4 liters of SC(-Leu) medium containing 1% glucose and 2% galactose. Cells were harvested by centrifugation, washed once with ice-cold PBS, quick-frozen in liquid nitrogen, and stored at −80° C. Frozen pellets were resuspended in 50 ml of lysis buffer (0.1 M sorbitol 50 mM K-acetate, 2 mM EDTA, 1 mM DTT, 1 mM PMSF, 20 mM HEPES (pH 7.5) plus 1× protease inhibitor cocktail "for use with fungal and yeast extracts" (Sigma-Aldrich). Cells were then disrupted using a FastPrep-24 instrument (MP Biomedicals, Solon Ohio) at the speed setting of 6.5, at 20 sec/cycle, for 6 cycles. After removal of the glass beads, unbroken cells were removed by two rounds of centrifugation in the Sorvall RT-600B centrifuge at 3,000 rpm for 5 min at 4° C. The resulting supernatant was centrifuged at 11,200 g for 10 min at 4° C. The pellets, which contained membrane-embedded Doa10$_f$, were washed twice in 25 ml of buffer 88 (0.25 M sorbitol, 0.15 M K-acetate, 5 mM Mg-acetate, 20 mM HEPES (pH 6.8)) containing 1× protease inhibitor cocktail "for use with fungal and yeast extracts" (Sigma-Aldrich), using centrifugation at 11,200 g for 10 min. The resulting microsomes were resuspended and solubilized by incubating in 20 ml of extraction buffer (10% glycerol, 1% Triton X-100, 0.2 M KCl, 1 mM EDTA, 5 mM β-mercaptoethanol, 1 mM PMSF, 50 mM HEPES, (pH 7.5)) containing 1× protease inhibitor cocktail "for use with fungal and yeast extracts" (Sigma-Aldrich) for 2 hr at 4° C. The resulting suspension was centrifuged at 11,200 g for 30 min, and the supernatant was gently mixed with 2 ml of anti-flag M2 affinity beads (50% slurry) (Sigma-Aldrich) for 2 h at 4° C. The beads were then collected by centrifugation in the Sorvall RT-600B centrifuge at 1,000 rpm for 5 min at 4° C., and were washed, repeatedly, with 100 ml of extraction buffer. The anti-flag antibody-bound Doa10$_f$ was eluted with 5 ml of extraction buffer containing 0.5 mg/ml of the flag peptide (Sigma-Aldrich), followed by dialysis at 4° C. overnight against storage buffer (10% glycerol, 1% Triton X-100, 0.15 M NaCl, 5 mM β-mercaptoethanol, 50 mM HEPES, pH 7.5).

Example 12

SPOT Binding Assay

These experiments employed synthetic XZ-e$^K$($^{3-11}$) peptides and their Nt-acetylated $^{Ac}$XZ-e$^{K(3-11)}$ counterparts that were C-terminally linked to a cellulose-PEG membrane as "dots", in equal molar amounts. Except for varied residues XZ at positions 1 and 2 (including Nt-acetylated versus unacetylated residues at position 1), the sequences of the 11-residue SPOT-arrayed peptides were identical to the N-terminal sequence of e$^K$ (FIG. 5D). These PepSpot (PEG) peptides were synthesized using JPT Peptide Technology, GmbH (JPT) (Berlin, Germany). Each peptide "spot" contained approximately 5 nmoles of identical peptides covalently conjugated, C-terminally, to a cellulose-PEG-membrane. Before the binding assay, dry membranes were washed in methanol for 10 min, and 3 times for 20 min each in Tris-buffered saline (IBS) (170 mM NaCl, 6.4 mM KCl, 31 mM Tris-HCl, pH 7.6) at room temperature, and thereafter blocked by incubation in buffer A (10% glycerol, 50 uM bestatine, 0.1 M NaCl, 5 mM β-mercaptoethanol, 50 mM HEPES, pH 7.5) for 30 min at room temperature. Thereafter a SPOT membrane was incubated with 2.5 ml of the purified Doa10$_f$(0.1 mg/ml) in the storage buffer (10% glycerol, 1% Triton X-100, 0.15 M NaCl, 5 mM p-mercaptoethanol, 50 mM HEPES, pH 7.5) at room temperature for 2 hr. The membrane was then washed twice in buffer A for 15 min. The bound Doa10$_f$ was electroblotted onto polyvinylene difluoride (PVDF) membranes (Millipore) using a semi-dry blotter (Bio-Rad, Hercules, Calif.). During the transfer, PVDF membranes were sandwiched between blotting paper soaked with cathode buffer (25 mM Tris-base, 40 mM 6-aminohexane acid, 0.01% SDS, 20% MeOH) and one of the anode buffers (AI: 30 mM Tris base, 20% MeOH; AII: 300 mM Tris base, 20% MeOH). Electroblotting was performed twice for 30 min at the constant current of 0.8 mA per cm² of cellulose membrane. The transferred Doa10$_f$ were detected by immunoblotting with anti-flag antibody, using a SuperSignal West Pico Chemiluminescent Substrate (Thermo Scientific).

TABLE 1

S. cerevisiae strains used in this study.

| | |
|---|---|
| SC295 | MATα ura3-52 leu2-3, 112 regl-501 gal lpep4-3 |
| JD52 | MATα trpl-63 ura3-52 his3-200 leu2-3112. Iys2-801 |
| JD53 | MATα trpl-63 ura3-52 his3-200 Ieu2-3112. Iys2-801 |
| JD55 | ubr1Δ::HIS3 in JD52 |
| JD83-1A | ubr1Δ::HIS3 in JD53 |
| AVY105 | Ubr2Δ::HIS3 in JD52 |
| CHY49 | pdr5Δ::KanMX6 in JD52 |
| CHY134 | ubr1Δ::LEU2 ubr2Δ::HIS3 in JD52 |
| CHY194 | ufd4Δ::KanMX6 in JD52 |
| CHY195 | ubr1Δ::HIS3 ufd4Δ::KanMX6 in JD52 |
| CHY223 | doa10Δ::KanMX6 in JD53 |
| CHY229 | doa10Δ::KanMX6 ubr1Δ::HIS3 in JD53 |
| CHY248 | DOA10-13MYC:::KanMX6 in JD52 |
| CHY287 | ubc4Δ::LEU2 in BY4742 |
| CHY288 | ubc4Δ::LEU2 doa10Δ::KanMX6 in BY4742 |
| BY4742 | MATα his3-1 leu2-0 lys2-0 ura3-0 can1-100, |
| BY 10976 | ardlΔ::KanMX6 in B Y4742 |
| BY12509 | nat5Δ::KanMX6 in BY4742 |
| BY 15470 | mak3Δ::KanMX6 in BY4742 |
| BY15546 | nat3Δ::KanMX6 in BY4742 |
| BY 16202 | nat4Δ::KanMX6 in BY4742 |
| BY17299 | doa10Δ:KanMX6 in BY4742 |
| BY4741 | MATα his3-1 leu2-0 met 15-0 ura3-0 |
| BY4425 | rad6Δ:: KanMX4 in BY4741 |
| BY3771 | brelΔ:: KanMX4 in BY4741 |
| BY5787 | rad18Δ:: KanMX4 in BY4741 |
| BY4425 | ufd2Δ:: KanMX4 in BY4741 |
| BY3216 | ufd4Δ:: KanMX4 in BY4741 |
| BY3994 | hul4Δ:: KanMX4 in BY4741 |
| BY597 | hul5Δ:: KanMX4 in BY4741 |
| BY4763 | hrdlΔ:: KanMX4 in BY4741 |
| BY4156 | hrd3Δ:: KanMX4 in BY4741 |
| BY4883 | Tul1Δ: KanMX4 in BY4741 |
| BY7299 | doa10Δ::KanMX4 in BY4741 |
| BY4814 | ubr1Δ::KanMX4 in BY4741 |
| BY1579 | Ubr2Δ:: KanMX4 in BY4741 |
| BY3771 | brelΔ:: KanMX4 in BY4741 |
| BY5787 | radl8Δ;: KanMX4 in BY4741 |
| FW1808 | MATαhis4-912&R5 lys2-128δ ura3-52 rps5-1 |

TABLE 2

Plasmids used in this study.

| Plasmids | Description |
|---|---|
| pBAM | Ub-MH-e$^K$-ha-Ura3 in p314CUP1 |
| pMET416$_F$UPR CUP9$_{NSF}$ | $^f$DHFR-Ub$^{K48R}$-Cup9$_{NSF}$ in p416MET25 |
| pEJJ1-M | His$_6$Ub-Met-e$^K$-DHFR$_{ha}$ from the T7 promoter |
| pCH178 | Ub$^{K48R}$-CK-e$^K$-ha-Ura3 in p314CUP1 |
| pCH181 | Ub-CZ-e$^K$-ha-Ura3 in p314CUP1 |
| pCH183 | Ub$^{K48R}$-MK-e$^K$-ha-Ura3 in p314CUP1 |
| pCH194 | Ub-CP-e$^K$-ha-Ura3 in p314CUP1 |
| pCH195 | Ub$^{Q49R}$-CL-e$^K$-ha-Ura3 in p314CUP1 |
| pCH198 | Ub-CV-e$^K$-ha-Ura3 in p314CUP1 |
| pCH499 | Ub$^{K48R}$-CE-e$^K$-ha-Ura3 in p314CUP1 |
| pCH500 | Ub$^{K48R}$-CG-e$^K$-ha-Ura3 in p314CUP1 |
| pCH501 | Ub$^{K48R}$-CI-e$^K$-ha-Ura3 in p314CUP1 |
| pCH502 | Ub$^{K48R}$-CL-e$^K$-ha-Ura3 in p314CUP1 |
| pCH503 | Ub$^{K48R}$-CW-e$^K$-ha-Ura3 in p314CUP1 |
| pCH504 | Ub$^{K48R}$-ML-e$^K$-ha-Ura3 in p314CUP1 |
| pCH505 | Ub$^{K48R}$-SL-e$^K$-ha-Ura3 in p314CUP1 |
| pCH506 | Ub$^{K48R}$-TL-e$^K$-ha-Ura3 in p314CUP1 |
| pCH507 | Ub$^{Q49R}$-CL-e$^K$-ha-Ura3 in p313CUP1 |
| pCH508 | Ub$^{K48R}$-SL-e$^K$-ha-Ura3 in p313CUP1 |
| pCH509 | Ub$^{K48R}$-TL-e$^K$-ha-Ura3 in p314CUP1 |
| pCH535 | Ub$^{K48R}$-MN-Matα$^{3-67}$e$^K$-ha-Ura3 in p314CUP1 |

TABLE 2-continued

Plasmids used in this study.

| Plasmids | Description |
|---|---|
| pCH547 | Ub$^{K48R}$-MK-Matα$^{3-67}$e$^K$-ha-Ura3 in p314CUP1 |
| pCH548 | Ub$^{K48R}$-ML-Matα$^{3-67}$e$^K$-ha-Ura3 in p314CUP1 |
| pCH549 | Ub$^{K48R}$-MQ-Matα$^{3-67}$e$^K$-ha-Ura3 in p314CUP1 |
| pCH550 | Ub$^{K48R}$-MD-Matα$^{3-67}$e$^K$-ha-Ura3 in p314CUP1 |
| pCH551 | Ub$^{K48R}$-MA-Matα$^{3-67}$e$^K$-ha-Ura3 in p314CUP1 |
| pCH552 | Ub$^{K48R}$-MP-Matα$^{3-67}$e$^K$-ha-Ura3 in pS314CUP1 |
| pCH553 | Ub$^{K48R}$-RN-Matα$^{3-67}$e$^K$-ha-Ura3 in p314CUP1 |
| pCH554 | Ub$^{K48R}$-LN-Matα$^{3-67}$e$^K$-ha-Ura3 in p314CUP1 |
| pCH555 | Ub$^{K48R}$-NN-Matα$^{3-67}$e$^K$-ha-Ura3 in p314CUP1 |
| pCH556 | Ub$^{K48R}$-DN-Matα$^{3-67}$e$^K$-ha-Ura3 in p314CUP1 |
| pCH581 | Δdoa10 in p425GAL1 |
| pCH595 | Doa10$_f$ in p425GAL1 |
| pCH604 | Ub$^{K48R}$-MK-e$^K$-ha-Ura3-CL1 in p314CUP1 |
| pCH605 | Ub$^{K48R}$-GK-e$^K$-ha-Ura3-CL1 in p314CUP1 |
| pH$_{10}$UE | His$_{10}$-Ub in pET15b |
| pCH622 | MN-Matα$^{3-67}$-e$^K$-ha-Ura3 in pH$_{10}$UE |
| pCH623 | GN-Matα$^{3-67}$-e$^K$-ha-Ura3 in pH$_{10}$UE |
| pCH624 | MK-Matα$^{3-67}$-e$^K$-ha-Ura3 in pH$_{10}$UE |
| pCH625 | RN-Matα$^{3-67}$-e$^K$-ha-Ura3 in pH$_{10}$UE |
| pCH626 | Ub$^{K48R}$-NN-Matα$^{3-67}$e$^K$-ha-Ura3 in p314CUP1 |
| pCH641 | Ub$^{K48R}$-NN-Matα$^{3-67}$e$^K$-ha-Ura3 in p413CUP1 |
| pCH642 | Ub$^{K48R}$-GN-MATα$^{3-67}$e$^K$-ha-Ura3 in p413CUP1 |
| pCH643 | Ub$^{K48R}$-MK-MATα$^{3-67}$e$^K$-ha-Ura3 in p413CUP1 |
| pCH644 | Ub$^{K48R}$-RN-MATα$^{3-67}$e$^K$-ha-Ura3 in p413CUP1 |
| pCH645 | MN-MATα$^{3-67}$-e$^K$-DHFR$_{ha}$ in pH$_{10}$UE |
| pCH646 | GN-MATα$^{3-67}$-e$^K$-DHFR$_{ha}$ in pH$_{10}$UE |
| pCH647 | MK-MATα$^{3-67}$-e$^K$-DHFR$_{ha}$ in pH$_{10}$UE |
| pCH648 | RN-Matα$^{3-67}$-e$^K$-DHFR$_{ha}$ in pH$_{10}$UE |
| pCH666 | Ub$^{K48R}$-MK-Pca$^{3-392}$-e$^K$-ha-Ura3 in p413CUP1 |
| pCH667 | Ub$^{K48R}$-GK-Pca$^{3-392}$-e$^K$-ha-Ura3 in p413CUP1 |
| pCH668 | Ub$^{K48R}$-MK-e$^K$-ha-Ura3 in p313CUP1 |
| pCH669 | Ub$^{K48R}$-ML-e$^K$-ha-Ura3 in p313CUP1 |
| pCH685 | Ub$^{K48R}$-GL-e$^K$-ha-Ura3 in p313CUP1 |
| pCH686 | Ub$^{K48R}$-AL-e$^K$-ha-Ura3 in p313CUP1 |
| pCH687 | Ub$^{K48R}$-VL-e$^K$-ha-Ura3 in p313CUP1 |
| pCH688 | Ub$^{K48R}$-MPL-e$^K$-ha-Ura3 in p313CUP1 |
| pCH689 | Ub$^{K48R}$-CL-e$^K$-ha-Ura3 in p313CUP1 |
| pCH704 | MATα2$_{flag}$ in p416MET25 |
| pCH705 | MK-MATα2$^{3-210}{}_f$ in p416MET25 |
| pCH706 | MG-MATα2$^{3-210}{}_f$ in p416MET25 |
| pCH707 | MATα2$_f$ inp426GAL1 |
| pCH719 | $^f$DHFR-Ub$^{K48R}$-MN-MATα2$_f$ in p416MET25 |
| pCH720 | $^f$DHFR-Ub$^{K48R}$-MK-MATα2$_f$ in p416MET25 |
| pCH721 | $^f$DHFR-Ub$^{K48R}$-GN-MATα2$_f$ in p416MET25 |
| pCH731 | Ub$^{K48R}$-MD-e$^K$-ha-Ura3 in $_p$313CUP1 |
| pCH732 | Ub$^{K48R}$-ME-e$^K$-ha-Ura3 in p313CUP1 |
| pCH733 | Ub$^{K48R}$-MQ-e$^K$-ha-Ura3 in p313CUP1 |
| pCH734 | Ub$^{K48R}$-MN-e$^K$-ha-Ura3 in p313CUP1 |
| pCH735 | Ub$^{K48R}$-MF-e$^K$-ha-Ura3 in p313CUP1 |
| pCH736 | Ub$^{K48R}$-MY-e$^K$-ha-Ura3 in p313CUP1 |
| pCH737 | Ub$^{K48R}$-MW-e$^K$-ha-Ura3 in p313CUP1 |
| pCH738 | Ub$^{K48R}$-MI-e$^K$-ha-Ura3 in p313CUP1 |

TABLE 3

PCR primers used in this study.

| Name | Sequence (SEQ ID NO'S 11-23) |
|---|---|
| OCH201 | 5'-GGG GAA TTC ATG CAG ATT TTC GTC AAG ACT TTG GTC-3' |
| OCH202 | 5'-AAA GGA TCC RNN ACA ACC ACC TCT TAG CCT TAG CAC AAG-3' |
| OCH214 | 5'-AAA GGA TCC TTT ACA ACC ACC GCG GAG CCT TAG CAC AAG-3' |
| OCH817 | 5'-GCT CCG CGG TGG TAT GAA TAA AAT ACC CAT TAA AGA C-3' |
| OCH818 | 5'-GCT CCG CGG TGG TGG TAA TAA AAT ACC CAT TAA AGA C-3' |

TABLE 3-continued

PCR primers used in this study.

| Name | Sequence (SEQ ID NO'S 11-23) |
|---|---|
| OCH819 | 5'-AAC CTC GAG TTA CTT GTC ATC ATC GTC CTT GTA GTC GGA AGT ACC AGA TTC TTT CTT CTT TGC CAG AGG CTC-3' |
| OCH833 | 5'-AAT GGA TCC AAT CTT ACG GTT TTT GTT GGC CCT-3' |
| OCH837 | 5'-GCT CCG CGG TGG TAT GAA AAA AAT ACC CAT TAA AGA CCT TTT-3' |
| OCH901 | 5'-AAA GGA TCC ATG GAT GTT GAT TCT GAC GTT AAT GTC TCC AGG TTA AGA GAT GAA CCC GGG GTT TAC ACT AAG GGT AGA GCT TTA GAAAAT-3' |
| OCH902 | 5'-AAC CTC GAG TTA CTT GTC ATC ATC GTC CTT GTA GTC GGA AGT ACC AGA ACT TTC ATC TGG TAA ATT TTC TAA AGC TCT ACC CTT AGT GTA-3' |
| OCH989 | 5'-AAC GGA TCC ATG AAT AAA ATA CCC ATT AAA GAC-3' |
| OCH990 | 5'-AAC GGA TCC ATG AAA AAA ATA CCC ATT AAA GAC CTT TTA-3' |
| OCH991 | 5'-AAC GGA TCC ATG GGT AAT AAA ATA CCC ATT AAA GAC CTT TTA-3' |

While the present disclosure has been particularly shown and described with reference to several embodiments thereof, it will be understood by those of ordinary skill in the art that various changes in form and details may be made thereto without departing from the principles and spirit of the present disclosure, the proper scope of which is defined in the following claims and their equivalents.

What is claimed is:

1. A method of identifying an agent that modulates $N^\alpha$-terminal acetyl transferase-mediated N-end rule pathway-mediated acetylation of an amino terminal (N-terminal) Met, Ala, Val, Ser, Thr, Cys, Gly, or Pro residue of a peptide, comprising:
 a) contacting at least one sample comprising a peptide having an N-terminal Met, Ala, Val, Ser, Thr, Cys, Gly, or Pro residue of the peptide, wherein the peptide comprises an N-terminal portion of a fusion protein and wherein the fusion protein comprises a reporter polypeptide C-terminal to the peptide, with at least one test agent, under conditions suitable for the N-terminal Met, Ala, Val, Ser, Thr, Cys, Gly, or Pro residue of the peptide to act as a substrate for an N-end rule pathway reaction;
 b) using mass spectroscopy or capillary electrophoresis, analyzing the results to detect a change in the N-end rule pathway substrate activity of the N-terminal Met, Ala, Val, Ser, Thr, Cys, Gly, or Pro residue of the peptide of a) in the presence of the test agent as compared to the activity in the absence of the test agent;
 wherein a change identifies the test agent as an agent that modulates $N^\alpha$-terminal acetyl transferase-mediated N-end rule pathway-mediated acetylation of an amino terminal (N-terminal) Met, Ala, Val, Ser, Thr, Cys, Gly, or Pro residue of the peptide, wherein the acetylated peptide is a substrate of Doa10 E3 Ub ligase.

2. The method of claim 1, wherein the peptide comprises a regulator of G protein signaling (RGS) protein.

3. The method of claim 1, wherein the peptide comprises a synthetic peptide.

4. The method of claim 1, wherein the reporter polypeptide comprises a selectable marker protein or a detectable label.

5. The method of claim 4, wherein the selectable marker protein is an antibiotic resistance protein.

6. The method of claim 4, wherein the detectable label comprises a fluorescent protein, a luminescence generating protein, or an enzyme.

7. The method of claim 6, wherein the fluorescent protein is Aequorea green fluorescent protein, the luminescence generating protein is luciferase, or the enzyme is β-galactosidase.

8. The method of claim 1, where the fusion protein is inducible.

9. The method of claim 1, wherein the peptide having Met, Ala, Val, Ser, Thr, Cys, Gly, or Pro residue comprises an internal portion of a protein, and wherein the method further comprises contacting the protein with a protease that cleaves the protein to generate the amino terminal (N-terminal) Met, Ala, Val, Ser, Thr, Cys, Gly, or Pro residue of the peptide.

10. The method of claim 1, wherein the test agent alters N-terminal acetylation of the amino terminal (N-terminal) Met, Ala, Val, Ser, Thr, Cys, Gly, or Pro residue of the peptide.

11. The method of claim 10, wherein the test agent reduces or inhibits N-terminal acetylation of the amino terminal (N-terminal) Met, Ala, Val, Ser, Thr, Cys, Gly, or Pro residue of the peptide.

12. The method of claim 1, wherein the test agent alters the N-terminal acetylation of the amino terminal (N-terminal) Met, Ala, Val, Ser, Thr, Cys, Gly, or Pro residue of the peptide by an $N^\alpha$-terminal acetyl transferase.

13. The method of claim 12, wherein the $N^\alpha$-terminal acetyl transferase comprises a mammalian $N^\alpha$-terminal acetyl transferase.

14. The method of claim 1, wherein the sample comprises a cell-free sample.

15. The method of claim 1, wherein the sample comprises a cell, or an extract of a cell.

16. The method of claim 15, wherein the cell is a cell of a plant or a cell of an animal.

17. The method of claim 15, wherein the cell expresses an $N^\alpha$-terminal acetyl transferase.

18. The method of claim 17, wherein the $N^\alpha$-terminal acetyl transferase is endogenous to the cell.

19. The method of claim 1, wherein detecting a change in the N-end rule pathway substrate activity of the amino terminal (N-terminal) Met, Ala, Val, Ser, Thr, Cys, Gly, or Pro residues of the peptide comprises measuring the N-terminal acetylation of the amino terminal (N-terminal) Met, Ala, Val, Ser, Thr, Cys, Gly, or Pro residues of the peptide.

\* \* \* \* \*

SEQUENCE LISTING

<160> NUMBER OF SEQ ID NOS: 29

<210> SEQ ID NO 1
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 1

Met Asn Lys Ile Pro Ile Lys Asp Leu Leu Asn Cys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Met, acetylated Met (Ac-Met) or Gly

<400> SEQUENCE: 2

Xaa Asn Lys Ile Pro Ile Lys Asp Leu Leu Asn Cys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Gly, Met, Arg, or Phe

<400> SEQUENCE: 3

Xaa Ile Phe Ser Thr Asp Thr Gly Pro Gly Gly Cys
1               5                   10

```
<210> SEQ ID NO 4
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 4

Met Asn Lys Ile Pro Ile Lys
1               5

<210> SEQ ID NO 5
<211> LENGTH: 15
<212> TYPE: PRT
<213> ORGANISM: Artificial Sequence
<220> FEATURE:
<223> OTHER INFORMATION: Synthetic construct

<400> SEQUENCE: 5

Met Leu Gly Ser Gly Ala Trp Leu Leu Pro Val Ser Leu Val Lys
1               5                   10                  15

<210> SEQ ID NO 6
<211> LENGTH: 36
<212> TYPE: DNA
<213> ORGANISM: Artificial Sequence
<220> FEATURE:
<223> OTHER INFORMATION: Primer

<400> SEQUENCE: 6
ggggaattca tgcagatttt cgtcaagact ttggtc                                 36

<210> SEQ ID NO 7
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (11)..(12)
<223> OTHER INFORMATION: n is a, c, g, or t

<400> SEQUENCE: 7
aaaggatccr nnacaaccac ctcttagcct tagcacaag                              39

<210> SEQ ID NO 8
<211> LENGTH: 10
<212> TYPE: PRT
<213> ORGANISM: Artificial Sequence
<220> FEATURE:
<223> OTHER INFORMATION: Synthetic construct

<400> SEQUENCE: 8

His His His His His His His His His His
1               5                   10

<210> SEQ ID NO 9
<211> LENGTH: 6
<212> TYPE: PRT
<213> ORGANISM: Artificial Sequence
<220> FEATURE:
<223> OTHER INFORMATION: Synthetic construct
```

<400> SEQUENCE: 9

His His His His His His
1               5

<210> SEQ ID NO 10
<211> LENGTH: 12
<212> TYPE: PRT
<213> ORGANISM: Artificial Sequence
<220> FEATURE:
<223> OTHER INFORMATION: Synthetic construct

<400> SEQUENCE: 10

Met Asn Lys Ile Pro Ile Lys Asp Leu Leu Asn Cys
1               5                   10

<210> SEQ ID NO 11
<211> LENGTH: 36
<212> TYPE: DNA
<213> ORGANISM: Artificial Sequence
<220> FEATURE:
<223> OTHER INFORMATION: Primer

<400> SEQUENCE: 11
ggggaattca tgcagatttt cgtcaagact ttggtc                              36

<210> SEQ ID NO 12
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (11)..(12)
<223> OTHER INFORMATION: n is a, c, g, or t

<400> SEQUENCE: 12
aaaggatccr nnacaaccac ctcttagcct tagcacaag                           39

<210> SEQ ID NO 13
<211> LENGTH: 39
<212> TYPE: DNA
<213> ORGANISM: Artificial Sequence
<220> FEATURE:
<223> OTHER INFORMATION: Primer

<400> SEQUENCE: 13
aaaggatcct ttacaaccac cgcggagcct tagcacaag                           39

<210> SEQ ID NO 14
<211> LENGTH: 37
<212> TYPE: DNA
<213> ORGANISM: Artificial Sequence
<220> FEATURE:
<223> OTHER INFORMATION: Primer

<400> SEQUENCE: 14
gctccgcggt ggtatgaata aaatacccat taaagac                             37

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
gctccgcggt ggtggtaata aaatacccat taaagac                                    37

<210> SEQ ID NO 16
<211> LENGTH: 72
<212> TYPE: DNA
<213> ORGANISM: Artificial Sequence
<220> FEATURE:
<223> OTHER INFORMATION: Primer

<400> SEQUENCE: 16
aacctcgagt tacttgtcat catcgtcctt gtagtcggaa gtaccagatt ctttcttctt          60
tgccagaggc tc                                                               72

<210> SEQ ID NO 17
<211> LENGTH: 33
<212> TYPE: DNA
<213> ORGANISM: Artificial Sequence
<220> FEATURE:
<223> OTHER INFORMATION: Primer

<400> SEQUENCE: 17
aatggatcca atcttacggt ttttgttggc cct                                        33

<210> SEQ ID NO 18
<211> LENGTH: 42
<212> TYPE: DNA
<213> ORGANISM: Artificial Sequence
<220> FEATURE:
<223> OTHER INFORMATION: Primer

<400> SEQUENCE: 18
gctccgcggt ggtatgaaaa aaatacccat taaagacctt tt                              42

<210> SEQ ID NO 19
<211> LENGTH: 90
<212> TYPE: DNA
<213> ORGANISM: Artificial Sequence
<220> FEATURE:
<223> OTHER INFORMATION: Primer

<400> SEQUENCE: 19
aaaggatcca tggatgttga ttctgacgtt aatgtctcca ggttaagaga tgaacccggg          60
gtttacacta agggtagagc tttagaaaat                                            90

<210> SEQ ID NO 20
<211> LENGTH: 90
<212> TYPE: DNA
<213> ORGANISM: Artificial Sequence
<220> FEATURE:
<223> OTHER INFORMATION: Primer

<400> SEQUENCE: 20
aacctcgagt tacttgtcat catcgtcctt gtagtcggaa gtaccagaac tttcatctgg          60
taaattttct aaagctctac ccttagtgta                                            90

<210> SEQ ID NO 21
<211> LENGTH: 33
<212> TYPE: DNA
<213> ORGANISM: Artificial Sequence
<220> FEATURE:
<223> OTHER INFORMATION: Primer

<400> SEQUENCE: 21

```
aacggatcca tgaataaaat acccattaaa gac                                   33
```

<210> SEQ ID NO 22
<211> LENGTH: 39
<212> TYPE: DNA
<213> ORGANISM: Artificial Sequence
<220> FEATURE:
<223> OTHER INFORMATION: Primer

<400> SEQUENCE: 22

```
aacggatcca tgaaaaaaat acccattaaa gacctttta                             39
```

<210> SEQ ID NO 23
<211> LENGTH: 42
<212> TYPE: DNA
<213> ORGANISM: Artificial Sequence
<220> FEATURE:
<223> OTHER INFORMATION: Primer

<400> SEQUENCE: 23

```
aacggatcca tgggtaataa atacccatt aaagaccttt ta                          42
```

<210> SEQ ID NO 24
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Cys at residue 1 is oxidized

<400> SEQUENCE: 24

```
Cys Asn Gln Asp Glu Arg Lys His Leu Phe Trp Tyr Ile
1               5                   10
```

<210> SEQ ID NO 25
<211> LENGTH: 6
<212> TYPE: PRT
<213> ORGANISM: Artificial Sequence
<220> FEATURE:
<223> OTHER INFORMATION: Synthetic construct

<400> SEQUENCE: 25

```
Met Ala Val Ser Thr Cys
1               5
```

<210> SEQ ID NO 26
<211> LENGTH: 7
<212> TYPE: PRT
<213> ORGANISM: Artificial Sequence
<220> FEATURE:
<223> OTHER INFORMATION: Synthetic construct

<400> SEQUENCE: 26

```
Gly Pro Ser Thr Ala Val Cys
1               5
```

<210> SEQ ID NO 27
<211> LENGTH: 11
<212> TYPE: PRT
<213> ORGANISM: Artificial Sequence
<220> FEATURE:
<223> OTHER INFORMATION: Synthetic construct

<400> SEQUENCE: 27

```
Cys Asp Glu Arg Lys His Leu Phe Trp Tyr Ile
1               5                   10

<210> SEQ ID NO 28
<211> LENGTH: 38
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: Xaa can be any naturally occurring amino acid

<400> SEQUENCE: 28

Xaa Xaa Gly Ser Gly Ala Trp Leu Leu Pro Val Ser Leu Val Lys Arg
1               5                   10                  15

Lys Thr Thr Leu Ala Pro Asn Thr Gln Thr Ala Ser Pro Arg Ala Leu
            20                  25                  30

Ala Asp Ser Leu Met Gln
        35

<210> SEQ ID NO 29
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 29

Met Leu Gly Ser Gly Ala Trp Leu Leu Pro Val Ser Leu Val Lys
1               5                   10                  15
```